US009809654B2

(12) United States Patent
Robert et al.

(10) Patent No.: US 9,809,654 B2
(45) Date of Patent: Nov. 7, 2017

(54) TARGETED CD1D MOLECULES

(75) Inventors: Bruno Robert, Saint Hippolyte du Four (FR); Alena Donda, Les Cullayes (CH); Valerie Cesson, Saint Gingolph (FR); Jean-Pierre Mach, Bellevue (CH); Maurice Zauderer, Pittsford, NY (US)

(73) Assignee: Vaccinex, Inc., Rochester, NY (US)

( * ) Notice: Subject to any disclaimer, the term of this patent is extended or adjusted under 35 U.S.C. 154(b) by 1273 days.

(21) Appl. No.: 10/529,221

(22) PCT Filed: Sep. 26, 2003

(86) PCT No.: PCT/US03/30238
§ 371 (c)(1),
(2), (4) Date: Jun. 30, 2006

(87) PCT Pub. No.: WO2004/029206
PCT Pub. Date: Apr. 8, 2004

(65) Prior Publication Data
US 2006/0269540 A1    Nov. 30, 2006

(30) Foreign Application Priority Data

Sep. 27, 2002    (EP) .................................. 02405838

(51) Int. Cl.
C07K 19/00    (2006.01)
C07K 16/30    (2006.01)
C07K 14/74    (2006.01)
A61K 35/17    (2015.01)

(52) U.S. Cl.
CPC ........ C07K 16/30 (2013.01); C07K 14/70539 (2013.01); C07K 2317/54 (2013.01); C07K 2317/55 (2013.01); C07K 2319/00 (2013.01)

(58) Field of Classification Search
None
See application file for complete search history.

(56) References Cited

U.S. PATENT DOCUMENTS

| | | | |
|---|---|---|---|
| 4,690,915 A | 9/1987 | Rosenberg | |
| 5,081,029 A | 1/1992 | Zarling et al. | |
| 5,194,425 A | 3/1993 | Sharma et al. | |
| 5,264,618 A | 11/1993 | Felgner et al. | |
| 5,635,363 A | 6/1997 | Altman et al. | |
| 5,679,347 A | 10/1997 | Porcelli et al. | |
| 5,780,441 A | 7/1998 | Higa et al. | |
| 5,849,716 A | 12/1998 | Akimoto et al. | |
| 5,853,737 A | 12/1998 | Modlin et al. | |
| 5,936,076 A | 8/1999 | Higa et al. | |
| 6,015,884 A | 1/2000 | Schneck et al. | |
| 6,162,609 A | 12/2000 | Hafler et al. | |
| 6,238,676 B1 | 5/2001 | Porcelli et al. | |
| 6,248,564 B1 | 6/2001 | Walter et al. | |
| 6,531,453 B1 | 3/2003 | Taniguchi et al. | |
| 6,548,067 B1 | 4/2003 | Seeman et al. | |
| 6,682,741 B1 | 1/2004 | Ribaudo et al. | |
| 6,747,010 B2 | 6/2004 | Taniguchi et al. | |
| 6,881,828 B2 | 4/2005 | Edwards et al. | |
| 7,273,852 B2 | 9/2007 | Tsuji et al. | |
| 7,666,656 B2 | 2/2010 | Sun et al. | |
| 7,772,380 B2 | 8/2010 | Porcelli | |
| 8,022,043 B2 | 9/2011 | Porcelli | |
| 9,139,809 B2 | 9/2015 | Porcelli et al. | |
| 2002/0051783 A1 | 5/2002 | Savage | |
| 2002/0071842 A1 | 6/2002 | Gumperz et al. | |
| 2002/0155447 A1 | 10/2002 | Zauderer et al. | |
| 2003/0157135 A1 | 8/2003 | Tsuji et al. | |
| 2003/0166277 A1 | 9/2003 | Zauderer | |
| 2004/0091488 A1 | 5/2004 | Seeman et al. | |
| 2004/0096429 A1 | 5/2004 | Savage | |
| 2004/0127429 A1 | 7/2004 | Tsuji | |
| 2004/0210037 A1 | 10/2004 | Zauderer et al. | |
| 2005/0042218 A1 | 2/2005 | Zauderer | |
| 2005/0112141 A1 | 5/2005 | Terman | |
| 2005/0192248 A1 | 9/2005 | Tsuji et al. | |
| 2006/0019246 A1 | 1/2006 | Tsuji et al. | |
| 2006/0052316 A1 | 3/2006 | Porcelli | |
| 2006/0074235 A1 | 4/2006 | Annoura et al. | |
| 2006/0116331 A1 | 6/2006 | Jiang et al. | |
| 2006/0148723 A1 | 7/2006 | Yamamura et al. | |
| 2006/0211856 A1 | 9/2006 | Tsuji et al. | |

(Continued)

FOREIGN PATENT DOCUMENTS

AU    B-39005/89    2/1990
EP    0 133 988 A2    3/1985
(Continued)

OTHER PUBLICATIONS

Donda et al (Cancer Immunity Aug. 2003, 3: 11).*
Fujii et al (Nature Immunology, Sep. 2002, 3(9): 867-875).*
Pavlinkova et al (Cancer immunology and immunotherapy, 2000, 49(4-5): 267-275).*
Burdin et al (J. Immunol. 1998, 161: 3271-3281).*
Tamada et al (Journal of Immunology, 1997, 158: 4846-4854).*
Stetson et al (J. Exp. Med. Oct. 6, 2003, 198(7): 1069-1076).*
Hermans, I.F., "Dendritic Cell Function Can Be Modulated through Cooperative Action of TLR Ligands and Invariant NKT Cells," *J. Immunol.* 178:2721-2729, The American Association of Immunologists, Inc. (Mar. 2007).
Nagarajan, N.A., and Kronenberg, M., "Invariant NKT Cells Amplify the Innate Immune Response to Lipopolysaccharide," *J. Immunol.* 178:2706-2713, The American Association of Immunologists, Inc. (Mar. 2007).

(Continued)

*Primary Examiner* — Gerald R Ewoldt
*Assistant Examiner* — Marianne Dibrino
(74) *Attorney, Agent, or Firm* — Thompson Coburn LLP

(57) ABSTRACT

The invention is directed to a compound comprising one or more CD1d complexes in association with an antibody specific for a cell surface marker. The CD1d complexes comprise a CD1d, a β2-microglobulin molecule, and may further comprise an antigen bound to the CD1d binding groove. The invention is further directed to methods of inhibiting or stimulating an immune response with the CD1d-antibody compounds, in particular anti-tumor and autoimmunity responses.

29 Claims, 3 Drawing Sheets

(56) References Cited

U.S. PATENT DOCUMENTS

| | | | |
|---|---|---|---|
| 2006/0269540 | A1 | 11/2006 | Robert et al. |
| 2007/0238673 | A1 | 10/2007 | Porcelli |
| 2007/0287664 | A1 | 12/2007 | Ralston et al. |
| 2007/0292418 | A1 | 12/2007 | Fields et al. |
| 2008/0254045 | A1 | 10/2008 | Donda et al. |
| 2010/0183549 | A1 | 7/2010 | Porcelli et al. |
| 2013/0164325 | A1 | 6/2013 | Porcelli et al. |
| 2014/0227296 | A1 | 8/2014 | Porcelli et al. |

FOREIGN PATENT DOCUMENTS

| | | |
|---|---|---|
| EP | 0 352 761 A2 | 1/1990 |
| GB | 2 339 782 A | 2/2000 |
| WO | WO 93/10220 A1 | 5/1993 |
| WO | WO 94/24142 | 10/1994 |
| WO | WO 94/25610 A1 | 11/1994 |
| WO | WO 96/26962 A1 | 9/1996 |
| WO | WO 97/35991 A1 | 10/1997 |
| WO | WO 98/07441 A1 | 2/1998 |
| WO | WO 98/23627 | 6/1998 |
| WO | WO 98/44928 | 10/1998 |
| WO | WO 99/11775 A1 | 3/1999 |
| WO | WO 99/13095 A1 | 3/1999 |
| WO | WO 99/21572 A1 | 5/1999 |
| WO | WO 99/31241 A1 | 6/1999 |
| WO | WO 99/64464 A2 | 12/1999 |
| WO | WO 99/64597 A1 | 12/1999 |
| WO | WO 00/00156 A2 | 1/2000 |
| WO | WO 01/44296 A1 | 6/2001 |
| WO | WO 01/71005 A2 | 9/2001 |
| WO | WO 01/72995 A2 | 10/2001 |
| WO | WO 01/78768 A2 | 10/2001 |
| WO | WO 01/90198 A1 | 11/2001 |
| WO | WO 02/27027 A2 | 4/2002 |
| WO | WO 03/009812 A2 | 2/2003 |
| WO | WO 03/016326 | 2/2003 |
| WO | WO 2004/028475 A2 | 4/2004 |
| WO | WO 2004/029206 A2 | 4/2004 |
| WO | WO 2004/072091 A1 | 8/2004 |
| WO | WO 2005/000348 A2 | 1/2005 |
| WO | WO 2006/026389 A2 | 3/2006 |
| WO | WO 2007/007946 A1 | 1/2007 |
| WO | WO 2008/103392 A2 | 8/2008 |
| WO | WO 2008/133801 A1 | 11/2008 |
| WO | WO 2008/140598 | 11/2008 |
| WO | WO 2010/081026 A1 | 7/2010 |
| WO | WO 2012/006342 A1 | 1/2012 |
| WO | WO 2014/124245 | 8/2014 |

OTHER PUBLICATIONS

Parekh, V.V., et al., "The In Vivo Response of Invariant Natural Killer T Cells to Glycolipid Antigens," *Int. Rev. Immunol.* 26:31-48, Taylor & Francis (Jan.-Apr. 2007).

Silk, J.D., et al., "Utilizing the adjuvant properties of CD1d-dependent NK T cells in T cell-mediated immunotherapy," *J. Clin. Invest.* 114:1800-1811, American Society for Clinical Investigation (Dec. 2004).

Stirnemann, K., et al., "Sustained activation and tumor targeting of NKT cells using a CD1d-anti-HER2-scFv fusion protein induce antitumor effects in mice," *J. Clin. Invest.* 118:994-1005, American Society for Clinical Investigation (Mar. 2008).

Stronge, V.S., et al., "A closer look at CD1d molecules: new horizons in studying NKT cells," *Trends Immunol.* 28:455-462, Elsevier Science Ltd. (Oct. 2007).

Van Kaer L., "NKT cells: T lymphocytes with innate effector functions," *Curr. Opin. Immunol.* 19:354-364, Elsevier Ltd. (Jun. 2007).

Co-pending U.S. Appl. No. 12/034,737, inventors Zauderer, M., et al., filed Feb. 21, 2008.

Wilson, M.T., et al., "Immunotherapy with ligands of natural killer T cells," *Trends Mol. Med.* 8:225-231, Elsevier Science Ltd. (May 2002).

Abastado, J.-P., et al., "Dimerization of Soluble Major Histocompatibility Complex-Peptide Complexes Is Sufficient for Activation of T Cell Hybridoma and Induction of Unresponsiveness," *J. Exp. Med.* 182:439-447, The Rockefeller University Press (1995).

Abdel-Wahab, Z., et al., "Human Dendritic Cells, Pulsed with either Melanoma Tumor Cell Lysates or the gp100 Peptide$_{(280-288)}$, Induce Pairs of T-Cell Cultures with Similar Phenotype and Lytic Activity," *Cell. Immunol.* 186:63-74, Academic Press (1998).

Alexander, J., et al., "Recognition of a Novel Naturally Processed, A2 Restricted, HCV-NS4 Epitope Triggers IFN-gamma Release in Absence of Detectable Cytopathicity," *Hum. Immunol.* 59:776-782, Elsevier Science, Inc. (1998).

Alexander, M., et al., "Generation of tumor-specific cytolytic T lymphocytes from peripheral blood of cervical cancer patients by in vitro stimulation with a synthetic human papillomavirus type 16 E7 epitope," *Am. J. Obstet. Gynecol.* 175:1586-1593, Mosby-Year Book, Inc. (1996).

Altman, J.D., et al., "Phenotypic Analysis of Antigen-Specific T Lymphocytes," *Science* 274:94-96, American Association for the Advancement of Science (1996).

Battegay, M., et al., "Patients with Chronic Hepatitis C Have Circulating Cytotoxic T Cells Which Recognize Hepatitis C Virus-Encoded Peptides Binding to HLA-A2.1 Molecules," *J. Virol.* 69:2462-2470, American Society for Microbiology (1995).

Bedzyk, W.D., et al., "Immunological and Structural Characterization of a High Affinity Anti-fluorescein Single-chain Antibody," *J. Biol. Chem.* 265:18615-18620, The American Society for Biochemistry and Molecular Biology, Inc. (1990).

Bertoletti, A., et al., "Molecular Features of the Hepatitis B Virus Nucleocapsid T-Cell Epitope 18-27: Interaction with HLA and T-Cell Receptor," *Hepatology* 26:1027-1034, American Association for the Study of Liver Diseases (1997).

Bocchia, M., et al., "Specific Binding of Leukemia Oncogene Fusion Protein Peptides to HLA Class I Molecules," *Blood* 85:2680-2684, The American Society of Hematology (1995).

Bocchia, M., et al., "Specific Human Cellular Immunity to bcr-abl Oncogene-Derived Peptides," *Blood* 87:3587-3592, The American Society of Hematology (1996).

Boitel, B., et al., "Strong Similarities in Antigen Fine Specificity Among DRB1*1302-Restricted Tetanus Toxin tt830-843-Specific TCRs in Spite of Highly Heterongenous CDR3," *J. Immunol.* 154:3245-3255, The American Association of Immunologists (1995).

Boniface, J.J., et al., "Initiation of Signal Transduction through the T Cell Receptor Requires the Peptide Multivalent Engagement of MHC Ligands," *Immunity* 9:459-466, Cell Press (1998).

Brinckerhoff, L.H., et al., "Terminal Modifications Inhibit Proteolytic Degradation of an Immunogenic Mart-$_{127-35}$ Peptide: Implications for Peptide Vaccines," *Int. J. Cancer* 83:326-334, Wiley-Liss, Inc. (1999).

Brusic, V., et al., "Prediction of MHC class II-binding peptides using an evolutionary algorithm and artificial neural network," *Bioinformatics* 14:121-130, Oxford University Press (1998).

Burrows, G.G., et al., "Two-Domain MHC Class II Molecules Form Stable Complexes with Myelin Basic Protein 69-89 Peptide That Detect and Inhibit Rat Encephalitogenic T Cells and Treat Experimental Autoimmune Encephalomyelitis," *J. Immunol.* 161:5987-5996, The American Association of Immunologists (1988).

Casares, S., et al., "Antigen-specific Signaling by a Soluble, Dimeric Peptide/Major Histocompatibility Complex Class II/Fc Chimera Leading to T Helper Cell Type 2 Differentiation," *J. Exp. Med* 190:543-553, The Rockefeller University Press (1999).

Castelli, C., et al., "Novel HLA-Cw8-Restricted T Cell Epitopes Derived from Tyrosinase-Related Protein-2 and gp100 Melanoma Antigens," *J. Immunol.* 162:1739-1748, The American Association of Immunologists (1999).

Celis, E., et al., "Identification of Potential CTL Epitopes of Tumor-Associated Antigen Mage-1 for Five Common HLA-A Alleles," *Mol. Immunol.* 31:1423-1430, Elsevier Science, Ltd. (1994).

Chaux, P., et al., "Identification of Mage-3 Epitopes Presented by HLA-DR Molecules to CD4$^+$ T Lymphocytes," *J. Exp. Med.* 189:767-777, The Rockefeller University Press (1999).

(56) References Cited

OTHER PUBLICATIONS

Chikamatsu, K., et al., "Generation of Anti-p53 Cytotoxic T Lymphocytes from Human Peripheral Blood Using Autologous Dendritic Cells," *Clin. Cancer Res.* 5:1281-1288, The American Association for Cancer Research (1999).

Cochran, J.R., et al., "The Relationship of MHC-Peptide Binding and T Cell Activation Probed Using Chemically Defined MHC Class II Oligomers," *Immunity* 12:241-250, Cell Press (2000).

Cormier, J.N., et al., Heterogeneous Expression of Melanoma-Associated Antigens and HLA-A2 in Metastatic Melanoma In Vivo, *Int. J. Cancer* 75:517-524, Wiley-Liss, Inc. (1998).

Dal Porto, J., et al., "A soluble divalent class I major histocompatibility complex molecule inhibits alloreactive T cells at nanomolar concentrations," *Proc. Natl. Acad. Sci. USA* 90:6671-6675, The National Academy of Sciences (1993).

Daniel, S., et al., "Relationship Between Peptide Selectivities of Human Transporters Associated with Antigen Processing and HLA Class I Molecules," *J. Immunol.* 161:617-624, The American Association of Immunologists (1998).

De Backer, O., et al., "Characterization of the GAGE Genes That Are Expressed in Various Human Cancers and in Normal Testis," *Cancer Res.* 59:3157-3165, The American Association for Cancer Research (1999).

Diepolder, H.M., et al., "Immunodominant $CD4^+$ T-Cell Epitope within Nonstructural Protein 3 in Acute Hepatitis C Virus Infection," *J. Virol.* 71:6011-6019, American Society for Microbiology (1997).

Doolan, D.L., et al., "Degenerate Cytotoxic T Cell Epitopes from P. falciparum Restricted by Multiple HLA-A and HLA-B Supertype Alleles," *Immunity* 7:97-112, Cell Press (1997).

Esser, S., et al., "Vascular endothelial growth gactor induces VE-cadherin tyrosine phosphorylation in endothelia cells," *J. Cell Sci.* 111:1853-1865, The Company of Biologists Limited (1998).

Fleischhauer, K., et al., "Functional Heterogeneity of HLA-A*02 Subtypes Revealed by Presentation of a MAGE-3-Encoded Peptide to Cytotoxic T Cell Clones," *J. Immunol.* 159:2513-2521, The American Association of Immunologists (1997).

Gotch, F., et al., "Cytotoxic T lymphocytes recognize a fragment of influenza virus matrix protein in association with HLA-A2," *Nature* 32:881-882, Nature Publishing Group (1987).

Greten, T.F., et al., "Direct visualization of antigen-specific T cells: HTLV-1 Tax11-19-specific $CD8^+$ T Cells are activated in peripheral blood and accumulate in cerebrospinal fluid from HAM/TSP patients," *Proc. Natl. Acad. Sci. USA* 95:7568-7573, The National Academy of Sciences (1998).

Hamad, A.R.A., et al., "Potent T Cell Activation with Dimeric Peptide—Major Histocompatibility Complex Class II Ligand: The Role of CD4 Coreceptor," *J. Exp. Med.* 188: 1633-1640, The Rockefeller University Press (1998).

Harbury, P.B., et al., "A Switch Between Two-, Three-, and Four-Stranded Coiled Coils in GCN4 Leucine Zipper Mutants," *Science* 262:1401-1407, American Association for the Advancement of Science (1993).

Harvill, E.T., et al., "In Vivo Properties of an IgG3-IL-2 Fusion Protein," *J. Immunol.* 157:3165-3170, The American Association of Immunologists (1996).

Heathcote, J., et al., "A Pilot Study of the CY-1899 T-Cell Vaccine in Subjects Chronically Infected with Hepatitis B Virus," *Hepatology* 30:531-536, The American Association of the Study of Liver Diseases (1999).

Höllsberg, P., et al., "Differential activation of proliferation and cytotoxicity in human T-cell lymphotropic virus type I Tax-specific CD8 T cells by an altered peptide ligand," *Proc. Natl. Acad. Sci. USA* 92:4036-4040, National Academy of Sciences (1995).

Kawashima, I., et al., "Identification of GP100-Derived, Melanoma-Specific Cytotoxic T-Lymphocyte Epitopes Restricted by HLA-A3 Supertype Molecules by Primary In Vitro Immunization With Peptide-Pulsed Dendritic Cells," *Int. J. Cancer* 75:518-524, Wiley-Liss, Inc. (1998).

Kawashima, I., et al., "Identification of HLA-A3-restricted Cytotoxic T Lymphocyte Epitopes from Carcinoembryonic Antigen and HER-2/neu by Primary in Vitro Immunization with Peptide-pulsed Dendritic Cells," *Cancer Res.* 59:431-435, The American Association for Cancer Research (1999).

Kim, J., et al., "Determinants of T Cell Reactivity to the *Mycobacterium leprae* GroES Homologue," *J. Immunol.* 159:335-343, The American Association of Immunologists (1997).

Kono, K., et al., "Identification of HER2/neu-Derived Peptide Epitopes Recognized by Gastric Cancer-Specific Cytotoxic T Lymphocytes," *Int. J. Cancer* 78:202-208, Wiley-Liss, Inc. (1998).

Kundu, S.K., et al., "Role of Preimmunization Virus Sequences in Cellular Immunity in HIV-Infected Patients during HIV Type 1 MN Recombinant gp 160 Immunization," *Aids Res. Hum. Retroviruses* 14:1669-1678, Mary Ann Liebert, Inc. (1998).

Lachman, L.B., et al., "Cytokine-Containing Liposomes as Adjuvants for Subunit Vaccines," in *Vaccine Design: The Subunit and Adjuvant Approach*, Powell, M.F., and Newman, M.J., eds., Plenum Press, New York, NY, pp. 659-671 (1995).

Livingston, B.D., et al., "The Hepatitis B Virus-Specific CTL Responses Induced in Humans by Lipopeptide Vaccination are Comparable to Those Elicited by Acute Viral Infection," *J. Immunol.* 159:1383-1392, The American Association of Immunologists (1997).

Manici, S., et al., "Melanoma Cells Present a MAGE-3 Epitope to $CD4^+$ Cytotoxic T Cells in Association with Histocompatibility Leukocyte Antigen DR11," *J. Exp. Med.* 189:871-876, The Rockefeller University Press (1999).

Morrison, S.L., et al., "Production and Characterization of Genetically Engineered Antibody Molecules," *Clin. Chem.* 34:1668-1675, Journal of the American Association for Clinical Chemistry, Inc. (1988).

Nukaya, I., et al., "Identification of HLA-A24 Epitope Peptides of Carcinoembryonic Antigen Which Induce Tumor-Reactive Cytotoxic Lymphocyte," *Int. J. Cancer* 80:92-97, Wiley-Liss, Inc. (1999).

Pack, P., et al., "Tetravalent Miniantibodies with High Avidity Assembling in *Escherichia coli*," *J. Mol. Biol.* 246:28-34, Academic Press Limited (1995).

Parham, P., et al., "Carbohydrate Moiety of HLA Antigens," *J. Biol. Chem.* 252:7555-7567, The American Society of Biological Chemists, Inc. (1977).

Parkhurst, M.R., et al., "Identification of a Shared HLA-A*0201-restricted T-Cell Epitope from the Melanoma Antigen Tyrosinase-related Protein 2 (TRP2)," *Cancer Res.* 58:4895-4901, The American Association for Cancer Research (1998).

Peiper, M., et al., "Pancreatic Cancer Associated Ascites-Derived CTL Recognize a Nine-Amino-Acid Peptide GP2 Derived from HER2/neu," *Anticancer Res.* 19:2471-2476, International Institute Anticancer Research (1999).

Penichet, M.L., et al., "An Antibody-Avidin Fusion Protein Specific for the Transferrin Receptor Serves as a Delivery Vehicle for Effective Brain Targeting: Initial Applications in Anti-HIV Antisense Drug Delivery to the Brain," *J. Immunol.* 163:4421-4426, The American Association of Immunologists (1999).

Ramakrishna, V., et al., "Generation and Phenotypic Characterization of New Human Ovarian Cancer Cell Lines with the Identification of Antigens Potentially Recognizable by HLA-Restricted Cytotoxic T Cells," *Int. J. Cancer* 73:143-150, Wiley-Liss, Inc. (1997).

Ressing, M.E., et al., "Human CTL Epitopes Encoded by Human Papillomavirus Type 16 E6 and E7 Identified Through In Vivo and In Vitro Immunogenicity Studies of HLA-A*0201-Binding Peptides," *J. Immunol.* 154:5934-5943, The American Association of Immunologists (1995).

Rivoltini, L., et al., "A Superagonist Variant of Peptide MART1/Melan $A_{27-35}$ Elicits Anti-Melanoma $CD8^+$ T Cells with Enhanced Functional Characteristics: Implication for More Effective Immunotherapy," *Cancer Res.* 59:301-306, The American Association for Cancer Research (1999).

Robert, B., et al., "Antibody-conjugated MHC class I tetramers can target tumor cells for specific lysis by T lymphocytes," *Eur. J. Immunol.* 30:3165-3170, Wiley-VCH Verlag GmbH (2000).

(56) References Cited

OTHER PUBLICATIONS

Rongcun, Y., et al., "Identification of New HER2/neu-Derived Peptide Epitopes That Can Elicit Specific CTL Against Autologous and Allogenic Carcinomas and Melanomas," *J. Immunol.* 163:1037-1044, The American Association of Immunologists (1999).
Rötzschke, O., et al., "Conformational variants of class II MHC/peptide complexes induced by N- and C-terminal extensions of minimal peptide epitopes," *Proc. Natl. Acad. Sci. USA* 96:7445-7450, National Academy of Sciences (1999).
Rötzschke, O., et al., "Superactivation of an immune response triggered by oligomerized T cell epitopes," *Proc. Natl. Acad. Sci. USA* 94:14642-14647, National Academy of Sciences (1997).
Salazar-Onfray, F., et al., "Synthetic Peptides Derived from the Melanocyte-stimulating Hormone Receptor MC1R Can Stimulate HLA-A2-restricted Cytotoxic T Lymphocytes That Recognize Naturally Processed Peptides on Human Melanoma Cells," *Cancer Res.* 57:4348-4355, The American Association for Cancer Research (1997).
Schmitt, L., et al., "Catalysis of peptide dissociation from Class II MHC-peptide complexes," *Proc. Natl. Acad. Sci. USA* 96:6581-6586, The National Academy of Sciences (1999).
Schnell, S., et al., "Retrovirally Transduced Mouse Dendritic Cells Require $CD4^+$ T Cell Help to Elicit Antitumor Immunity: Implications for the Clinical Use of Dendritic Cells," *J. Immunol.* 164:1243-1250, The American Association of Immunologists (2000).
Shin, S.-U. and Morrison, S.L., "Production and Properties of Chimeric Antibody Molecules," in *Methods in Enzymology*, Langone, J.J., ed., Academic Press, Inc., New York, pp. 459-477 (1989).
Shin, S.-U., et al., "Functional and Pharmacokinetic Properties of Antibody-Avidin Fusion Proteins," *J. Immunol.* 158:4797-4804, The American Association of Immunologists (1997).
Springer, T.A. and Strominger, J.L., "Detergent-soluble HLA antigens contain a hydrophilic region at the COOH-terminus and a penultimate hydrophobic region," *Proc. Natl. Acad. Sci. USA* 73:2481-2485, The National Academy of Sciences (1976).
Steller, M.A., et al., "Cell-mediated Immunological Responses in Cervical and Vaginal Cancer Patients Immunized with a Lipidated Epitope of Human Papillomavirus Type 16 E7," *Clin. Cancer Res.* 4:2103-2109, The American Association for Cancer Research (1998).
Takahashi, T., et al., "707-AP Peptide Recognized by Human Antibody Induces Human Leukocyte Antigen A2-restricted Cytotoxic T Lymphocyte Killing of Melanoma," *Clin. Cancer Res.* 3:1363-1730, The American Association for Cancer Research (1997).
Takahashi, T., et al., "Cytotoxic T lymphocytes that recognize decameric peptide sequences of retinoblastoma binding protein 1 (RBP-1) associated with human breast Cancer," *British J. Cancer* 81:342-349, Cancer Research Campaign (1999).
Tanzarella, S., et al., "Identification of a Promiscuous T-Cell Epitope Encoded by Multiple Members of the MAGE Family," *Cancer Res.* 59:2668-2674, The American Association for Cancer Research (1999).
Turkewitz, A.P., et al., "Large-Scale Purification of Murine $I-A^k$ and $I-E^k$ Antigens and Characterization of the Purified Proteins," *Mol. Immunol.* 20:1139-1147, Pergamon Press Ltd. (1983).
Turner, M.J., et al., "Purification of Papain-solubilized Histocompatibility Antigens from a Cultured Human Lymphoblastoid Line, RPMI 4265*," *J. Biol. Chem.* 250:4512-4519, The American Society of Biological Chemists, Inc. (1975).
Valmori, D., et al., "Analysis of MAGE-3-specific Cytolytic T Lymphocytes in Human Leukocyte Antigen-A2 Melanoma Patients," *Cancer Res.* 57:735-741, The American Association for Cancer Research (1997).
Valmori, D., et al., "Analysis of the Cytolytic T Lymphocyte Response of Melanoma Patients to the Naturally HLA-A*0201-associated Tyrosinase Peptide 368-376," *Cancer Res.* 59:4050-4055, The American Association for Cancer Research (1999).

Valmori, D., et al., "Diversity of the Fine Specificity Displayed by HLA-A*0201-Restricted CTL Specific for the Immunodominant Melan-A/MART-1 Antigenic Peptide," *J. Immunol.* 161:6956-6962, The American Association of Immunologists (1998).
Wang, R.-F., et al., "Recognition of an Antigenic Peptide Derived from Tyrosinase-Related Protein-2 by CTL in the Context of HLA-A31 and -A33," *J. Immunol.* 160:890-897, The American Association of Immunologists (1998).
Wizel, B., et al., "HLA-A2-Restricted Cytotoxic T Lymphocyte Responses to Multiple *Plasmodium falciparum* Sporozoite Surface Protein 2 Epitopes in Sporozoite-Immunized Volunteers," *J. Immunol.* 155:766-775, The American Association of Immunologists (1995).
Wizel, B., et al., "Human Infection with *Trypanosoma cruzi* Induces Parasite Antigen-Specific Cytotocxic T Lymphocyte Responses," *J. Clin. Invest.* 102:1062-1071, The American Society for Clinical Investigation, Inc. (1998).
Zarour, H.M., et al., "Melan-A/MART-$1_{51-73}$ represents an immunogenic HLA-DR4-restricted epitope recognized by melanoma-reactive $CD4^+$ T Cells," *Proc. Natl. Acad. Sci. USA* 97:400-405, The National Academy of Sciences (2000).
Zarutskie, J.A., et al., "A Conformational Change in the Human Major Histocompatibility Complex Protein HLA-DR1 Induced by Peptide Binding," *Biochemistry* 38:5878-5887, American Chemical Society (1999).
Zhang, H.-f., et al., "Targeting of functional antibody-CD59 fusion proteins to a cell surface," *J. Clin. Invest.* 103:55-61, The American Society for Clinical Investigation (1999).
Zhu, X., et al., "A recombinant single-chain human class II MHC molecule (HLA-DR1) as a covalently linked heterotrimer of α chain, β chain, and antigenic peptide, with immunogenicity in vitro and reduced affinity for bacterial superantigens," *Eur. J. Immunol* 27:1933-1941, Verlagsgesellschaft (1997).
Fayen, J., et al., "Class I MHC Alpha 3 Domain Can Function as an Independent Structural Unit to Bind CD8α," *Mol. Immunol.* 32:267-275, Elsevier Science Ltd. (1995).
Glick, M., et al., "Novel $CD8^+$ T Cell Antagonists Based on $\beta_2$-Microglobulin," *J. Biol. Chem.* 277:20840-20846, The American Society for Biochemistry and Molecular Biology, Inc. (Jun. 2002).
Hebert, A.M., et al., "Kinetics and Thermodynamics of β2-Microglobulin Binding to the α3 Domain of Major Histocompatibility Complex Class I Heavy Chain," *Biochem.* 40:5233-5242, American Chemical Society (published online Mar. 2001).
Hochman, J.H., et al., "Specific Associations of Fluorescent β-2-Microglobulin with Cell Surfaces. The Affinity of Different H-2 and HLA Antigens for β-2-Microglobulin," *J. Immunol.* 140:2322-2329, The American Association of Immunologists (1988).
Mottez, E., et al., "Cells Expressing a Major Histocompatibility Complex Class I Molecule with a Single Covalently Bound Peptide Are Highly Immunogenic," *J. Exp. Med.* 181:493-502, Rockefeller University Press (1995).
Parker, K.C., and Strominger, J.L., "Subunit Interactions of Class I Histocompatibility Antigens," *Biochem.* 24:5543-5550, American Chemical Society (1985).
Salter, R.D., et al., "A binding site for the T-cell co-receptor CD8 on the $\alpha_3$ domain of HLA-A2," *Nature* 345:41-46, Nature Publishing Group (1990).
Sidney, J., et al., "Practical, biochemical and evolutionary implications of the discovery of HLA class I supermotifs," *Immunol. Today* 17:261-266, Elsevier Science Ltd. (1996).
Sidney, J., et al., "Majority of Peptides Binding HLA-A*0201 With High Affinity Crossreact With Other A2-Supertype Molecules," *Hum. Immunol.* 62:1200-1216, Elsevier Science Inc. (Nov. 2001).
Whitman, M.C., et al., "The isolated major histocompatibility complex class I α3 domain binds β2m and CD8αα dimers," *Mol. Immunol.* 37:141-149, Elsevier Science Ltd. (2000).
Hoffman, P., et al., "Large-scale in vitro expansion of polyclonal human $CD4^+CD25^{high}$ regulatory T cells," *Blood* 104:895-903, The American Society of Hematology (Aug. 2004).
Ogg, G.S., et al., "Sensitization of tumour cells to lysis by virus-specific CTL using antibody-targeted MHC class I/peptide complexes," *Br. J. Cancer* 82:1058-1062, Cancer Research Campaign (2000).

(56) References Cited

OTHER PUBLICATIONS

Timmerman, J.M., and Levy, R., "Dendritic Cell Vaccines for Cancer Immunotherapy," *Annu. Rev. Med.* 50:507-529, Annual Reviews (1999).

Zemon, H., "An artificial solution for adoptive immunotherapy," *Trends Biotechnol.* 21:418-420, Elsevier Science Publishers (Oct. 2003).

Balk, S., "Isolation and characterization of cDNA and gene coding for a fourth CD1 molecule," *Proc. Natl. Acad. Sci. USA*, 1989, vol. 86, pp. 252-256.

Beaudoin, L., et al., "NKT Cells Inhibit the Onset of Diabetes by Impairing the Development of Pathogenic T Cells Specific for Pancreatic β Cells," *Immunity*, 2002, vol. 17, pp. 725-736.

Bendelac, A., et al., "CD1 Recognition by Mouse NK1$^+$ T Lymphocytes," *Science*, 1995, vol. 268, pp. 863-865.

Benlagha, K., et al., "In Vivo Identification of Glycolipid Antigen-specific T Cells Using Fluorescent CD1d Tetramers," *J. Exp. Med.*, 2000, vol. 191(11), pp. 1895-1903.

Bonish, B., et al., "Overexpression of CD1d by Keratinocytes in Psoriasis and CD1d-Dependent IFN-γ Production by NK-T Cells," *The Journal of Immunology*, 2000, vol. 165, pp. 4076-4085.

Carnaud, C., et al., "Cutting Edge: Cross-Talk Between Cells of the Innate Immune System: NKT Cells Rapidly Activate NK Cells," *The Journal of Immunology*, 1999, vol. 163, pp. 4647-4650.

Chen, H., et al., "Cultured NK1.1$^+$CD4$^+$ T Cells Produce Large Amounts of IL-4 and IFN-γ Upon Activation by Anti-CD3 or CD1," *The Journal of Immunology*, 1997, vol. 159, pp. 2240-2249.

Cui, J., et al., "Requirement for V$_α$14 NKT Cells in IL-12-Mediated Rejection of Tumors," *Science*, 1997, vol. 278, pp. 1623-1626.

Dutronc, Y., et al., "The CD1 family and T cell recognition of lipid antigens," *Tissue Antigens*, 2002, vol. 60, pp. 337-353.

Eberl, G., et al., "Selective induction of NK cell proliferation and cytotoxicity by activated NKT cells," *Eur. J. Immunol.*, 2000, vol. 30, pp. 985-992.

Exley, M., et al., "Requirements for CD1d Recognition by Human Invarient Vα24$^+$ CD4$^-$ CD8$^-$ T Cells," *J. Exp. Med.*, 1997, vol. 186(1), pp. 109-120.

Gonzalez-Aseguinolaza, G., et al., "α-Galactosylceramide-activated Vα14 natural killer T cells mediate protection against murine malaria," *PNAS*, 2000, vol. 97(15), pp. 8461-8466.

Gumperz, J., et al., "Functionally Distinct Subsets of CD1d-restricted Natural Killer T Cells Revealed by CD1d Tetramer Staining," *J. Exp. Med.*, 2002, vol. 195(5), pp. 625-636.

Hemmi, H., et al., "Small anti-viral compounds activate immune cells via the TLR7 MyD88-dependent signaling pathway," *Nature Immunology*, 2002, vol. 3(2), pp. 196-200.

Hermans, I., et al., "NKT Cells Enhance CD4$^+$ and CD8$^+$ T Cell Responses to Soluble Antigen In Vivo through Direct Interaction with Dendritic Cells," *The Journal of Immunology*, 2003, vol. 171, pp. 5140-5147.

Illés, Z., et al., "Differential Expression of NK T Cell Vα24JαQ Invariant TCR Chain in the Lesions of Multiple Sclerosis and Chronic Inflammatory Demyelinating Polyneuropathy," *The Journal of Immunology*, 2000, vol. 164, pp. 4375-4381.

Jahng, A., et al., "Activation of Natural Killer T Cells Potentiates or Prevents Experimental Autoimmune Encephalomyelitis," *J. Exp. Med.*, 2001, vol. 194(12), pp. 1789-1799.

Karadimitris, A., et al., "Human CD1d-glycolipid tetramers generated by in vitro oxidative refolding chromatography," *PNAS*, 2001, vol. 98(6), pp. 3294-3298.

Kawano, T., et al., "CD1d-Restricted and TCR-Mediated Activation of V$_α$14 NKT Cells by Glycosylceramides," *Science*, 1997, vol. 278, pp. 1626-1629.

Kita, H., et al., "Quantitation and Phenotypic Analysis of Natural Killer T Cells in Primary Biliary Cirrhosis Using a Human CD1d Tetramer," *Gastroenterology*, 2002, vol. 123, pp. 1031-1043.

Kobayashi, E., et al., "KRN7000, A Novel Immunomodulator, and Its Antitumor Activities," *Oncology Research*, 1995, vol. 7(10/11), pp. 529-534.

Kojo, S., et al., "Alternative Splicing Forms of the Human CD1D Gene in Mononuclear Cells," *Biochemical and Biophysical Research Communications*, 2000, vol. 276, pp. 107-111.

Kojo, S., et al., "Low Expression Levels of Soluble CD1d Gene in Patients with Rheumatoid Arthritis," *The Journal of Rheumatology*, 2003, vol. 30(12), pp. 2524-2528.

Lee, A., et al., "Novel synthesis of α-galactosyl-ceramides and confirmation of their powerful NKT cell agonist activity," *Carbohydrate Research*, 2006, vol. 341, pp. 2785-2798.

Lee, P., et al., "Distinct Functional Lineages of Human Vα24 Natural Killer T Cells," *J. Exp. Med.*, 2002, vol. 195(5), pp. 637-641.

Matsuda, J., et al., "Tracking the Response of Natural Killer T Cells to a Glycolipid Antigen Using CD1d Tetramers," *J. Exp. Med.*, 2000, vol. 192(5), pp. 741-753.

Naumov, Y., et al., "Activation of CD1d-restricted T Cells protects NOD mice from developing diabetes by regulating dendritic cell subsets," *PNAS*, 2001, vol. 98(24), pp. 13838-13843.

Nishimura, T., et al., "The interface between innate and acquired immunity: glycolipid antigen presentation by CD1d-expressing dendritic cells to NKT cells induces the differentiation of antigen-specific cytotoxic T lymphocytes," *International Immunology*, 2000, vol. 12(7), pp. 987-994.

Reinhardt, C., et al., "Elevated frequencies of natural killer T lymphocytes in myasthenia gravis," *Neurology*, 1999, vol. 52, pp. 1485-1487.

Robert, B., et al., Redirecting anti-viral CTL against cancer cells by surface targeting of monomeric MHC class I-viral peptide conjugated to antibody fragments, *Cancer Immunity*, 2001, vol. 1, p. 2.

Saubermann, L., et al., "Activation of Natural KillerT Cells by α-galactosylceramide in the Presence of CD1d Provides Protection Against Colitis in Mice," *Gastroenterology* 2000, vol. 119, pp. 119-128.

Sege, K., et al., "Role of β$_2$-Microglobulin in the Intracellular Processing of HLA Antigens," *Biochemistry*, 1981, vol. 20, p. 4523-4530.

Sharif, S., et al., "Activation of natural killer cells by α-galactosylceramide treatment prevents the onset and recurrence of autoimmune Type 1 diabetes," *Nature Medicine*, 2001, vol. 7(9), pp. 1057-1062.

Sharif, S., et al., "Regulation of autoimmune disease by natural killer T Cells," *J Mol Med*, vol. 80, pp. 290-300.

Shi, F., et al., "Germ line deletion of the CD1 locus exacerbates diabetes in the NOD mouse," *PNAS*, 2001, vol. 98(12), pp. 6777-6782.

Singh, A., et al., "Natural Killer T Cell Activation Protects Mice Against Experimental Autoimmune Encephalomyelitis," *J. Exp. Med.*, 2001, vol. 194(12), pp. 1801-1811.

Smyth, M., et al., "NKT cells—conductors of tumor immunity?," *Curr Opin Immunol*, 2002, vol. 14, pp. 165-171.

Smyth, M., et al., "Sequential production of interferon-γ by NK1.1$^+$ T Cells and natural killer cells is essential for the antimetastatic effect of α-galactosylceramide," *Blood*, 2002, vol. 99(4), pp. 1259-1266.

Stober, D., et al., "NKT Cells Provide Help for Dendritic Cell-Dependent Priming of MHC Class I-Restricted CD8$^+$ T Cells In Vivo," *The Journal of Immunology*, 2003, vol. 170, pp. 2540-2548.

Sumida, T., et al., "Selective Reduction of T Cells Bearing Invariant Vα24JαQ Antigen Receptor in Patients with Systemic Sclerosis," *J. Exp. Med.*, 1995, vol. 182, pp. 1163-1168.

Tahir, S., et al., "Loss of IFN-γ Production by Invariant NK T Cells in Advanced Cancer," *The Journal of Immunology*, 2001, vol. 167, pp. 4046-4050.

Takeda, K., et al., "Relative contribution of NK and NKT cells to the anti-metastatic activities of IL-12," *International Immunology*, 2000, vol. 12(6), pp. 909-914.

Van Der Vliet, H., et al., "Circulating Vα24$^+$ Vβ11$^+$ NLT Cell Numbers Are Decreased in a Wide Variety of Diseases That Are Characterized by Autoreactive Tissue Damage," *Clinical Immunology*, 2001, vol. 100(2), pp. 144-148.

Wang, B., et al., "CD1-restricted NK T Cells Protect Nonobese Diabetic Mice from Developing Diabetes," *J. Exp. Med.*, 2001, vol. 194(3), pp. 313-319.

(56) References Cited

OTHER PUBLICATIONS

Zeng, Z., et al., "Crystal Structure of Mouse CD1: An MHC-Like Fold with a Large Hydrophobic Binding Groove," *Science*, 1997, vol. 277, pp. 339-345.

Bendle, G. M., et al., "A Study of T Cell Tolerance to the Tumor-Associated Antigen MDM2: Cytokines Can Resotre Antigen Responsiveness, but Not High Avidity T Cell Function," *PLoS ONE* 2(4): e353-e353 (9 pages), Public Library of Science, United States (Apr. 2007).

De St. Groth, B. F., et al., "T cell activation: in vivo veritas," *Immunol. Cell Biol.*, 82(3): 260-268, Australasian Society for Immunology Inc., Australia (Jun. 2004).

Hong, S., et al., "The natural killer T-cell ligand α-galactosylceramide prevents autoimmune diabetes in non-obese diabetic mice," *Nat. Med.*7(9): 1052-1056, Nature Publishing Group, United States (Sep. 2001).

Kakimi, K., et al., "Natural Killer T Cell Activation Inhibits Hepatits B Virus Replication In Vivo," *J. Exp. Med.* 192(7): 921-930, Rockefeller University Press, United States (Oct. 2000).

Kawakami, K., et al., "Activation of Vα14+ Natural Killer T Cells by α-Galactosylceramide Results in Development of Th1 Response and Local Host Resistance in Mice Infected with *Cryptococcus neoformans*," *Infect. Immun.* 69(1): 213-220, American Society for Microbiology, United States (Jan. 2001).

Mallevaey, T., et al., "Invariant and Noninvariant Natural Killer T Cells Exert Opposite Regulatory Funiction on the Immune Response during Murine Schistosomiasis," *Infect. Immun.* 75(5): 2171-2180, American Society for Microbiology, United States (May 2007).

Porubsky, S. et al., "Normal development and function of invariant natural killer T cells in mice with isoglobotrihexosylceramide (iGb3) deficiency," *Proc Natl Acad Sci U.S.A.* 104(14): 5977-5982, National Academy of Science, United States (Apr. 2007).

Schwartz, M., and Kipnis, J., "Multiple Sclerosis as a By-Product of the Failure to Sustain protective Autoimmunity: A Paradigm Shift," *Neuroscientist* 8(5): 405-413, Sage Publications, United States (Oct. 2002).

Singh, A. K., et al., "The natural killer T cell ligand α-galactosylceramide prevents or promotes pristane-induced lupus in mice," *Eur. J. Immunol.* 35(4):1143-1154, Weinheim : Wiley-VCH, Germany (Apr. 2005).

Taniguchi, M., et al., "The NKT cell system: bridging innate and acquired immunity," *Nat. Immunol.* 4(12): 1164-1165, Nature Publishing Group., United States (Dec. 2003).

Tisch, R., and McDevitt, H.O., "Antigen-specific immunotherapy: Is it a real possibility to combat T-cell-mediated autoimmunity?" *Proc. Natl. Acad. Sci. USA* 91: 437-438, National Academy of Sciences, United States (Jan. 1994).

Office Action dated Sep. 14, 2010, in U.S. Appl. No. 12/034,737, Donda, A., et al., filed Feb. 21, 2008.

Office Action dated Apr. 4, 2011, in U.S. Appl. No. 12/034,737, Donda, A., et al., filed Feb. 21, 2008.

Supplementary European Search Report with the European Search Opinion for European Patent Application No. EP 08 72 5849, European Patent Office, Germany, dated Oct. 27, 2011.

Naidenko, O., et al., "Binding and Antigen Presentation of Ceramide-containing Glycolipids by Soluble Mouse and Human CD1d Molecules," *J. Exp. Med.*, 1999, vol. 190(8), pp. 1069-1079.

Behar, S. M., et al., "Susceptibility of Mice Deficient in CD1D or TAP1 to Infection with *Mycobacterium tuberculosis*," *J. Exp. Med.*, 1999, vol. 189, No. 12, pp. 1973-1980.

Bendelac, A. & Medzhitov, R., "Adjuvants of Immunity: Harnessing Innate Immunity to Promote Adaptive Immunity," *J. Exp. Med.*, 2002, vol. 195, No. 5, pp. F19-F23.

Bendelac, A., "Mouse NK1+ T cells," *Curr. Opinion in Immunol.*, 1995, vol. 7, pp. 367-374.

Bendelac, A., et al., "Mouse CD-1 Specific NK1 T Cells: Development, Specificity, and Function," *Annu. Rev. Immunol.*, 1997, vol. 15, pp. 535-562.

Bhat, S., et al., "Galactosyl ceramide or a derivative is an essential component of the neural receptor for human immunodeficiency virus type 1 envelope glycoprotein gp120," *Proc. Natl. Acad. Sci. USA*, 1991, vol. 88, pp. 7131-7134.

Brossay, L., et al., "CD1d-mediated Recognition of an α-Galactosylceramide by Natural Killer T Cells Is Highly Conserved through Mammalian Evolution," *J. Exp. Med.*, 1998, vol. 188, pp. 1521-1528.

Brossay, L., et al., "Cutting Edge: Structural Requirements for Galactosylceramide Recognition by CD1-Restricted NK T Cells," *J. Immunol.*, 1998, vol. 161, pp. 5124-5128.

Brutkiewicz, R. R. and Sriram, V., "Natural killer T (NKT) cells and their role in antitumor immunity," *Crit. Rev. Oncol. Hematol.*, 2002, vol. 41, pp. 287-298.

Burdin, N., et al., "Immunization with α-galactosylceramide polarizes CD1-reactive NK T cells toward Th2 cytokine synthesis," *Eur. J. Immunol.*, 1999, vol. 29, pp. 2014-2025.

Bynoe, M., et al., "Estrogen up-regulates Bcl-2 and blocks tolerance induction of naïve B cells," *Proc. Natl. Acad. Sci.*, 2000, vol. 97, No. 6, pp. 2703-2708.

Bynoe, M., et al., "Characterization of anti-DNA B cells that escape negative selection," *Eur. J. Immunol.*, 1999, vol. 29, pp. 1304-1313.

Chackerian, A., et al., "Activation of NKT Cells Protects Mice from Tuberculosis," *Infection and Immunity*, 2002, vol. 70, No. 11, pp. 6302-6309.

Chambers, B. J., et al., "Triggering of Natural Killer Cells by the Costimulatory Molecule CD80 (B7-1)," *Immunity*, 1996, vol. 5, pp. 311-317.

Chang, Y-T., et al., "The Synthesis and Biological Characterization of a Ceramide Library," *J. Am. Chem. Soc.*, 2002, vol. 124, No. 9, pp. 1856-1857.

Chen, H., et al., NK1.1+CD4+ T Cells Lose NK1.1 Expression Upon In Vitro Activation, *J. Immunol.*, 1997, vol. 158, pp. 5112-5119.

Davodeau, F., et al., "Close Phenotypic and Functional Similarities Between Human and Murine αβ T Cells Expressing Invariant TCR α-Chains," *J. Immunol.*, 1997, vol. 158, pp. 5603-5611.

Eberl, G. and MacDonald, R., "Rapid Death and Regeneration of NKT Cells in Anti-CD3ε- or IL-12-Treated Mice: A Major Role for Bone Marrow in NKT Cell Homeostasis," *Immunity*, 1998, vol. 9, pp. 345-353.

Eberl, G., et al., "Tissue-Specific Segregation of CD1d-Dependent and CD1d-Independent NK T Cells," *J. Immunol.*, 1999, vol. 162, pp. 6410-6419.

Emoto, M., et al., "Induction of IFN-γ-producing CD4+ natural killer T cells by *Mycobacterium bovis* bacillus Calmette Guérin," *Eur. J. Immunol.*, 1999, vol. 29, pp. 650-659.

Godfrey, D., et al., "NKT cells: facts, functions and fallacies," *Immunol. Today*, 2000, vol. 21, No. 11, pp. 573-583.

Gonzalez-Aseguinolaza, G., et al., "Natural Killer T Cell Ligand α-Galactosylceramide Enhances Protective Immunity Induced by Malaria Vaccines," *J. Exp. Med.*, vol. 195, No. 5, pp. 617-624.

Gumperz, J. E., et al., "Murine CD1d-Restricted T Cell Recognition of Cellular Lipids," *Immunity*, 2000, vol. 12, pp. 211-221.

Hammond, K., et al., "α/β-T Cell Receptor (TCR)+CD4−CD8− (NKT) Thymocytes Prevent Insulin-dependent Diabetes Mellitus in Nonobese Diabetic (NOD)/Lt Mice by the Influence of Interleukin (IL)-4 and/or IL-10," *J. Exp. Med.*, 1998, vol. 187, No. 7, pp. 1047-1056.

Hayakawa, Y., et al., "Critical contribution of IFN-γ and NK cells, but not perforin-mediated cytotoxicity, to anti-metastatic effect of α-galactosylceramide," *Eur. J. Immunol.*, 2001, vol. 31, pp. 1720-1727.

Hong, S. and Van Kaer, L., "Immune Privilege: Keeping an Eye on Natural Killer T Cells," *J. Exp. Med.*, 1999, vol. 190, No. 9, pp. 1197-1200.

Iijima, H., et al., "Structure-Activity Relationship and Conformational Analysis of Monoglycosylceramides on the Syngeneic Mixed Leukocyte Reaction," *Bioorg. Med. Chem.*, 1998, vol. 6, pp. 1905-1910.

Ikarashi, Y., et al., "Dendritic Cell Maturation Overrules H-2D-mediated Natural Killer T (NKT) Cell Inhibition: Critical Role for B7 in CD1d-dependent NKT Cell Interferon γ Production," *J. Exp. Med.*, 2001, vol. 194, No. 8, pp. 1179-1186.

(56) References Cited

OTHER PUBLICATIONS

Inoue, H., et al., "α-Galactosylceramide (AGL-517) treatment protects mice from lethal irradiation," *Experimental Hematology*, 1997, vol. 25, pp. 935-944.
Ishikawa, H., et al., "CD4+ V$_\alpha$14 NKT cells play a crucial role in an early stage of protective immunity against infection with *Leishmania major*," *Int. Immunol.*, 2000, vol. 12, No. 9, pp. 1267-1274.
Jackman, R.M., et al., "Mechanisms of lipid antigen presentation by CD1," *Critical Reviews in Immunology*, 1999, vol. 19(1), pp. 49-63.
Joyce, S., et al., "Natural Ligand of Mouse CD1d1: Cellular Glycosylphosphatidylinositol," *Science*, 1998, vol. 279, pp. 1541-1544.
Kitamura, H., et al., "The Natural Killer T (NKT) Cell Ligand α-Galactosylceramide Demonstrates Its Immunopotentiating Effect by Inducing Interleukin (IL)-12 Production by Dendritic Cells and IL-12 Receptor Expression on NKT Cells," *J. Exp. Med.*, 1999, vol. 189, No. 7, pp. 1121-1127.
Kobayashi, E., et al., "Enhancing Effects of Agelasphin-11 on Natural Killer Cell Activities of Normal and Tumor-Bearing Mice," *Biol. Pharm. Bull.*, 1996, vol. 19, No. 3, pp. 350-353.
Kobayashi, E., et al., "Enhancing Effects of α-, β-Monoglycosylceramides on Natural Killer Cell Activity," *Bioorg. Med. Chem.*, 1996, vol. 4, No. 4, pp. 615-619.
Kojo, S., et al., "Dysfunction of T Cell Receptor AV24AJ18+, BV11+ Double-Negative Regulatory Natural Killer T Cells in Autoimmune Diseases," *Arthritis & Rheumatism*, 2001, vol. 44, No. 5, pp. 1127-1138.
Koseki, H., et al., "Dominant expression of a distinctive V14+ T-cell antigen receptor α chain in mice," *Proc. Natl. Acad. Sci. USA*, 1991, vol. 88, pp. 7518-7522.
Kronenberg, M. and Gapin, L., "The Unconventional Lifestyle of NKT Cells," *Nature Reviews Immunol.*, 2002, vol. 2, pp. 557-568.
Laloux, V., et al., "NK T Cell-Induced Protection Against Diabetes in Vα14-Jα281 Transgenic Nonobese Diabetic Mice Is Associated with a Th2 Shift Circumscribed Regionally to the Islets and Functionally to Islet Autoantigen," *J. Immunol.*, 2001, vol. 166, pp. 3749-3756.
Livingston, P., et al., "Improved Survival in Stage III Melanoma Patients with GM2 Antibodies: A Randomized trial of Adjuvant Vaccination With GM2 Ganglioside," *Journal of Clinical Oncology*, May 1994, vol. 12(5), pp. 1036-1044.
MacDonald, H., "Development and selection of NKT cells," *Current Opinion in Immunology*, 2002, vol. 14, pp. 250-254.
Matsuda, J. & Kronenberg, M. "Presentation of self and microbial lipids by CD1 molecules," *Current Opinion in Immunology*, 2001, vol. 13, pp. 19-25.
Mieza, M. A., et al., "Selective Reductioni of Vα14+ NK T Cells Associated with Disease Development in Autoimmune-Prone Mice," *J. Immunol.*, 1996, vol. 156, pp. 4035-4040.
Moody, D., et al., "The molecular basis of CD1-mediated presentation of lipid antigens," *Immunol. Rev.*, 1999, vol. 172, pp. 285-296.
Morita, M., et al., "Structure-Activity Relationship of α-Galactosylceramides against B16-Bearing Mice," *J. Med. Chem.*, 1995, vol. 38, pp. 2176-2187.
Motoki, K., et al., "Effects of α-Galactosylceramides on Bone Marrow Cells in Vitro and Hematopoiesis in Vivo," *Biol. Pharm. Bull.*, 1996, vol. 19, No. 7, pp. 952-955.
Motoki, K., et al., "Immunostimulatory and Antitumor Activities of Monoglycosylceramides Having Various Sugar Moieties," *Biol. Pharm. Bull.*, 1995, vol. 18, No. 11, pp. 1487-1491.
Nagle, D., et al., "New Glycosphingolipids From the Marine Sponge *Halichondria panicea*," *Journal of Natural Products*, 1992, vol. 55, No. 7, pp. 1013-1017.
Nakagawa, R., et al., "Antitumor Activity of α-Galactosylceramide, KRN7000, in Mice With EL-4 Hepatic Metastasis and its Cytokine Production," *Oncology Research*, 1998, vol. 10, pp. 561-568.
Nakagawa, R., et al., "Antitumor Activity of α-Galactosylceramide, KRN7000, in Mice With the Melanoma B16 Hepatic Metastasis and Immunohistological Study of Tumor Infiltrating Cells," *Oncology Research*, 2000, vol. 12, pp. 51-58.
NCBI Entrez, GenBank Report, Accession No. NP 001009066 (Entry Date 2005), 2 pages.
NCBI Entrez, GenBank Report, Accession No. NP 001009284 (Entry Date 2005), 2 pages.
NCBI Entrez, GenBank Report, Accession No. NP 001065272 (Entry Date 2006), 2 pages.
NCBI Entrez, GenBank Report, Accession No. NP 001757 (Entry Date 1999), 4 pages.
NCBI Entrez, GenBank Report, Accession No. NP 004039 (Entry Date 1999), 3 pages.
NCBI Entrez, GenBank Report, Accession No. NP 031665 (Entry Date 2000), 3 pages.
NCBI Entrez, GenBank Report, Accession No. NP 033865 (Entry Date 2000), 3 pages.
NCBI Entrez, GenBank Report, Accession No. NP 036644 (Entry Date 2000), 3 pages.
NCBI Entrez, GenBank Report, Accession No. NP 058775 (Entry Date 2000), 2 pages.
NCBI Entrez, GenBank Report, Accession No. NP 999143 (Entry Date 2004), 2 pages.
NCBI Entrez, GenBank Report, Accession No. O62848 (Entry Date 2001), 3 pages.
NCBI Entrez, GenBank Report, Accession No. P01885 (Entry Date 1993), 3 pages.
NCBI Entrez, GenBank Report, Accession No. P23043 (Entry Date 1993), 3 pages.
NCBI Entrez, GenBank Report, Accession No. Q29422 (Entry Date 2001), 3 pages.
Oishi, Y., et al., "Selective Reduction and Recovery of Invariant Vα24JαQ T Cell Receptor T Cells in Correlation with Disease Activity in Patients with Systemic Lupus Erythematosus," *J. Rheumatol.*, 2001, vol. 28, No. 2, pp. 275-283.
Park, S-H and Bendelac, A., "CD1-restricted T-cell responses and microbial infection," *Nature*, 2000, vol. 406, pp. 788-792.
Peterson, P. A., et al., "β$_2$-Microglobulin and the Major Histocompatibility Complex," *Adv. Cancer Res.*, 1977, vol. 24, pp. 115-163.
Porcelli, S. and Modlin, R., "The CD1 System: Antigen-Presenting Molecules for T Cell Recognition of Lipids and Glycolipids," *Annu. Rev. Immunol.*, 1999, vol. 17, pp. 297-329.
Porcelli, S., "The CD1 Family: A Third Lineage of Antigen-Presenting Molecules," *Advances in Immunology*, 1995, vol. 59, pp. 1-98.
Porcelli, S., et al., "Analysis of T Cell Antigen Receptor (TCR) Expression by Human Peripheral Blood CD4$^-$8$^-$ α/β T Cells Demonstrates Preferential Use of Several Vβ Genes and an Invariant TCR α Chain," *J. Exp. Med.*, 1993, vol. 178, pp. 1-16.
Porcelli, S., et al., "The CD1 family of lipid antigen-presenting molecules," *Review Immunology Today*, 1998, vol. 19, No. 8, pp. 362-368.
Schmieg, J., et al., "Superior Protection against Malaria and Melanoma Metastases by a C-glycoside Analogue of the Natural Killer T Cell Ligand α-Galactosylceramide," *The Journal of Experimental Medicine*, Dec. 1, 2003, vol. 198, pp. 1631-1641.
Seino, K-i., et al., "Requirement for natural killer T (NKT) cells in the induction of allograft tolerance," *Proc. Natl. Acad. Sci.*, 2001, vol. 98, No. 5, pp. 2577-2581.
Shamshiev, A., et al., "Self glycolipids as T-cell autoantigens," *Eur. J. Immunol.*, 1999, vol. 29, pp. 1667-1675.
Sidobre, S. and Kronenberg, M., "CD1 tetramers: a powerful tool for the analysis of glycolipid-reactive T cells," *Journal of Immunological Methods*, 2002, vol. 268, pp. 107-121.
Sidobre, S., et al., The Vα14 NKT Cell TCR Exhibits High-Affinity Binding to a Glycolipid/CD1d Complex[1], *The Journal of Immunology*, 2002, vol. 169, pp. 1340-1348.
Sieling, P. A., et al., "Human Double-Negative T Cells in Systematic Lupus Erythematosus Provide Help for IgG and Are Restricted by CD1c," *J. Immunol.*, 2000, vol. 165, pp. 5338-5344.
Smyth, M. and Godfrey, D. I., "NKT cells and tumor immunity—a double-edged sword," *Nature Immunology*, 2000, vol. 1, No. 6, pp. 459-460.

(56) References Cited

OTHER PUBLICATIONS

Sonoda, K-H, et al., "CD1-reactive Natural Killer T Cells Are Required for Development of Systemic Tolerance through an Immune-Privileged Site," *J. Exp. Med.*, 1999, vol. 190, No. 9, pp. 1215-1225.

Spada, F. M., et al., "CD1d-restricted Recognition of Synthetic Glycolipid Antigens by Human Natural Killer T Cells," *J. Exp. Med.*, 1998, vol. 188, No. 8, pp. 1529-1534.

Takeda, K. and Dennert, G., "The Development of Autoimmunity in C57BL/6 lpr Mice Correlates with the Disappearance of Natural Killer Type 1-positive Cells: Evidence for Their Suppressive Action on Bone Marrow Stem Cell Proliferation, B Cell Immunoglobulin Secretion, and Autoimmune Symptoms," *J. Exp. Med.*, 1993, vol. 177, pp. 155-164.

Uchimura, A., et al., "Immunostimulatory Activities of Mono- or Diglycosylated α-Galactosylceramides," *Bioorg. Med. Chem.*, 1997, vol. 5, No. 7, pp. 1447-1452.

Uchimura, A., et al., "Immunostimulatory Activities of Monoglycosylated α-D-Pyranosylceramides," *Bioorg. Med. Chem.*, 1997, vol. 5, No. 12, pp. 2245-2249.

Vincent, M. S., et al., "CD1-dependent dendritic cell instruction," *Nature Immunol.*, 2002, vol. 3, No. 12, pp. 1163-1168.

Wang, B., et al., "CD1-restricted NK T Cells Protect Nonobese Diabetic Mice from Developing Diabetes," *J. Exp. Med.*, 2001, vol. 194, No. 3, pp. 313-319.

Wilson, S. & Delovitch, T., Janus-Like Role of Regulatory iNKT Cells in Autoimmune Disease and Tumour Immunity, *Nature Review Immunology*, 2003, vol. 3, pp. 211-222.

Yamaguchi, Y., et al., "Enhancing Effects of (2S,3S,4R)-1-O-(α-D-galactopyranosyl)-2-(N-Hexacosanoylamino)-1,3,4-Octadecanetriol (KRN7000) on Antigen-Presenting Function of Antigen-Presenting Cells and Antimetastatic Activity of KRN7000-Pretreated Antigen-Presenting Cells," *Oncology Research*, 1996, vol. 8, Nos. 10/11, pp. 399-407.

Yoshimoto, T. and Paul W. E., "$CD4^{pos}$, $NK1.1^{pos}$ T Cells Promptly Produce Interleukin 4 in Response to In Vivo Challenge with Anti-CD3," *J. Exp. Med.*, 1994, vol. 179, pp. 1285-1295.

Yoshimoto, T., et al., "Defective IgE production by SJL mice is linked to the absence of $CD4^+$, $NK1.1^+$ T cells that promptly produce interleukin 4," *Proc. Natl. Acad. Sci. USA*, 1995, vol. 92, pp. 11931-11934.

Yoshimoto, T., et al., "Role of $NK1.1^+$ T Cells in a $T_H2$ Response and in Immunoglobulin E Production," *Science*, 1995, vol. 270, Issue 5243, pp. 1845-1847.

Zeng, D., et al., "Bone Marrow $NK1.1^-$ and $NK1.1^+$T Cells Reciprocally Regulate Acute Graft versus Host Disease," *J. Exp. Med.*, 1999, vol. 189, No. 7, pp. 1073-1081.

Zeng, D., et al., "Cutting Edge: A Role for CD1 in the Pathogenesis of Lupus in NZB/NZW Mice," *J. Immunol.*, 2000, vol. 164, pp. 5000-5004.

Balasubramanian, V., et al., "Mycobacterial Infection in Guinea Pigs," *Immunobiology*, 1994, vol. 191(4-5), pp. 395-401.

Barclay, W., et al., "Aerosol-Induced Tuberculosis in Subhuman Primates and the Course of the Disease After Intravenous BCG Vaccination," *Infect. Immun.*, 1970, vol. 2(5), pp. 574-582.

Crowe, N., et al., "Glycolipid Antigen Drives Rapid Expansion and Sustained Cytokine Production by NK T Cells," *J. Immunol.*, 2003, vol. 171, pp. 4020-4027.

Dunbar, P.R., et al., "Direct isolation, phenotyping and cloning of low-frequency antigen-specific cytotoxic T lymphocytes from peripheral blood," *Curr Biol*, 1998, vol. 8, No. 7, pp. 413-416.

Fischer, K., et al., "Mycobacterial phosphatidylinositol mannoside is a natural antigen for CD1d-restricted T Cells," *Proc Natl Acad Sci USA*, 2004, vol. 101(29), pp. 10685-10690.

Flynn, J., et al., "Major histocompatibility complex class I-restricted T cells are required for resistance to *Mycobacterium tuberculosis* infection," *Proc. Natl. Acad. Sci. USA*, 1992, vol. 89, pp. 12013-12017.

Freidag, B., et al., "CpG Oligodeoxynucleotides and Interleukin-12 Improve the Efficacy of *Mycobacterium bovis* BCG Vaccination in Mice Challenged with *M. tuberculosis*," *Infect. Immun.*, 2000, vol. 68(5), pp. 2948-2953.

Fujii, S., et al., "Activation of Natural Killer T Cells by α-Galactosylceramide Rapidly Induces the Full Maturation of Dendritic Cells In Vivo and Thereby Acts as an Adjuvant for Combined CD4 and CD8 T Cell Immunity to a Coadministered Protein," *J Exp. Med.*, 2003, vol. 198(2), pp. 267-279.

Gaynor, B., et al., "Peptide inhibition of glomerular deposition of an anti-DNA antibody," *Proc. Natl. Acad. Sci. USA*, 1997, vol. 94, pp. 1955-1960.

Hahn, B., "Antibodies to DNA," New England Journal of Medicine, 1998, vol. 338(19), pp. 1359-1368.

Hashimoto, M., et al., "Versatile Synthesis of Phenoxydiazirine-Based Fatty Acid Analogues and Photoreactive Galactosylceramide," *Bioorganic & Medicinal Chemistry Letters*, 2002, vol. 12, pp. 89-91.

Horwitz, M., et al., "Recombinant bacillus Calmette-Guérin (BCG) vaccines expressing the *Mycobacterium tuberculosis* 30-kDa major secretory protein induce greater protective immunity against tuberculosis than conventional BCG vaccines in a highly susceptible animal model," *Proc Natl Acad Sci USA*, 2000, vol. 97(25), pp. 13853-13858.

Hu, V. W. and Wisnieski, B. J., "Photoreactive labeling of M13 coat protein in model membranes by use of a glycolipid probe," *Proc. Natl. Acad. Sci. USA*, 1979, vol. 76, No. 11, pp. 5460-5464.

Im, J. S., et al., "Direct Measurement of Antigen Binding Properties of CD1 Proteins Using Florescent Lipid Probes," *J Biol Chem*, 2004, vol. 279, pp. 299-310.

Janeway, C.A., et al., "The structure of a typical antibody molecule," Immunobiology: The Immune System in Health and Disease, 5th ed., New York: Garland Science, 2011, pp. 1-9.

Kang, S., et al., "Saposins facilitate CD1d-restricted presentation of an exogenous lipid antigen to T cells," *Nature Immunology*, 2004, vol. 5, No. 2, pp. 175-181.

Kotzin, B., "Systemic Lupus Erythematosus," Cell, 1996, vol. 85, pp. 303-306.

Kuo, P., et al., "Bcl-2 leads to expression of anti-DNA B cells but no nephritis: a model for a clinical subset," *Eur. J. Immunol.*, 1999, vol. 29, pp. 3168-3178.

Lutz, M., et al., "An advanced culture method for generating large quantities of highly pure dendritic cells from mouse bone marrow," *J. Immunol. Methods*, 1999, vol. 223, pp. 77-92.

Matsumoto, S., et al., "Recombinant *Mycobacterium bovis* Bacillus Calmette-Guérin Secreting Merozoite Surface Protein 1 (MSP1) Induces Protection against Rodent Malaria Parasite Infection Depending on MSP1-stimulated Interferon γ and Parasite-specific Antibodies," *J. Exp. Med.*, 1998, vol. 188(5), pp. 845-854.

Minamino, M., et al., "Bacterial ceramides and sphingophospholipids induce apoptosis of human leukaemic cells," *Microbiology*, 2003, vol. 149, pp. 2071-2081.

Miyamoto, K., et al., "A synthetic glycolipid prevents autoimmune encephalomyelitis by inducing $T_H2$ bias of natural killer T cells," *Nature*, 2001, vol. 413, pp. 531-534.

Mogues, T., et al., "The Relative Importance of T Cell Subsets in Immunity and Immunopathology of Airborne *Mycobacterium tuberculosis* Infection in Mice," *J. Exp. Med.*, 2001, vol. 193(3), pp. 271-280.

Parekh, V., et al., "Quantitative and Qualitative Differences in the In Vivo Response of NKT Cells to Distinct α- and β-Anomeric Glycolipids", *J Immunol*, 2004, vol. 173, pp. 3693-3706.

Pisetsky, D., et al., "Systemic Lupus Erythematosus Diagnosis and Treatment," The Medical Clinics of North America Advances in Rheumatology, 1997, vol. 81(1), pp. 113-128.

Putterman, C., et al., "Immunization with a Peptide Surrogate for Double-stranded DNA (dsDNA) Induces Autoantibody Production and Renal Immunoglobulin Deposition," *J. Exp. Med.*, 1998, vol. 188(1), pp. 29-38.

Putterman, C., et al., "Molecular Analysis of the Autoantibody Response in Peptide-Induced Autoimmunity," *J Immunol*, 2000, vol. 164, pp. 2542-2549.

(56) References Cited

OTHER PUBLICATIONS

Sonnino, S., et al., "A Photoreactive Derivative of Radiolabeled GM1 Ganglioside: Preparation and Use to Establish the Involvement of Specific Proteins in GM1 Uptake by Human Fibroblasts in Culture," Biochemistry, 1989, vol. 28, pp. 77-84.
Spatz, L., et al., "Light Chain Usage in Anti-double-stranded DNA B Cell Subsets: Role in Cell Fate Determination," J. Exp. Med., 1997, vol. 185(7), pp. 1317-1326.
Tomioka, H., "Adjunctive Immunotherapy of Mycobacterial Infections," Current Pharmaceutical Design, 2004, vol. 10, pp. 3297-3312.
Wheeler, C.J., et al., "A novel cationic lipid greatly enhances plasmid DNA delivery and expression in mouse lung," Proc. Natl. Acad. Sci. U.S.A., 1996, vol. 93, pp. 11454-11459.
Wilson, S., et al., "Extreme Th1 bias of invariant Vα24JαQ T cells in type 1 diabetes," Nature, 1998, vol. 391, pp. 177-181.
Wu, D., et al., "Cross-presentation of Disialoganglioside GD3 to Natural Killer T Cells," J. Exp. Med., 2003, vol. 198(1), pp. 173-181.
Zegers, M. M. P., et al., "Use of photoactivatable sphingolipid analogues to monitor lipid transport in mammalian cells," Biochem. J., 1997, vol. 328, pp. 489-498.
Zuidam, N.J., et al., "Electrostatic parameters of cationic liposomes commonly used for gene delivery as determined by 4-heptadecyl-7-hydroxycoumarin," Biochem Biophys Acta, 1997, vol. 1329, No. 2, pp. 211-222.
Fujii, S-i., et al., "Glycolipid α-C-galactosylceramide is a distinct inducer of dendritic cell function during innate and adaptive immune responses of mice," PNAS, 2006, vol. 103, No. 30, pp. 11252-11257.
Kronenberg, M., "Toward an Understanding of NKT Cell Biology: Progress and Paradoxes," Annu. Rev. Immunol., 2005, vol. 26, pp. 877-900.
Mattner, J., et al., "Exogenous and endogenous glycolipid antigens activate NKT cells during microbial infections," Nature, 2005, vol. 434, pp. 525-529.
Parekh, V. V., et al., "Glycolipid antigen induces long-term natural killer T cell anergy in mice," The Journal of Clinical Investigation, 2005, vol. 115, pp. 2572-2583.
Ranson, T., et al., "Invariant Vα14$^+$ NKT Cells Participate in the Early Response to Enteric Listeria monocytogenes Infection," J. Immunol., 2005, vol. 175, pp. 1137-1144.
Rao, V., et al., "Mycobacterium tuberculosis controls host innate immune activation through cyclopropane modification of a glycolipid effector molecule," J. Exp. Med., 2005, vol. 201(4), pp. 535-543.
Rao, V., et al., "Trans-cyclopropanation of mycolic acids on trehalose dimycolate suppresses Mycobacterium tuberculosis-induced inflammation and virulence," J. Clin. Invest., 2006, vol. 116(6), pp. 1660-1667.
Smyth, M., et al., "Sequential activation of NKT cells and NK cells provides effective innate immunotherapy of cancer," The Journal of Experimental Medicine, 2005, vol. 201, No. 12, pp. 1973-1985.
Sullivan et al., "Activation or anergy: NKT cells are stunned by α-galactosylceramide," J. Clin. Invest., 2005, 115:2328-2329.
Tsuji, M., "Glycolipids and phospholipids as natural CD1d-binding NKT cell ligands," Cell Mol. Life Sci., 2006, vol. 63, pp. 1889-1898.
Uldrich et al., "NKT Cell Stimulation with Glycolipid Antigen In Vivo: Costimulation-Dependent Expansion, Bim-Dependent Contraction, and Hyporesponsiveness to Further Antigenic Challenge," J. Immunol., 2005, 175:3092-3101.
Yu, K. O. A., et al., "Modulation of CD1d-restricted NKT cell responses by using N-acyl variants of α-galactosylceramides," PNAS, 2005, vol. 102, No. 9, pp. 3383-3388.

\* cited by examiner

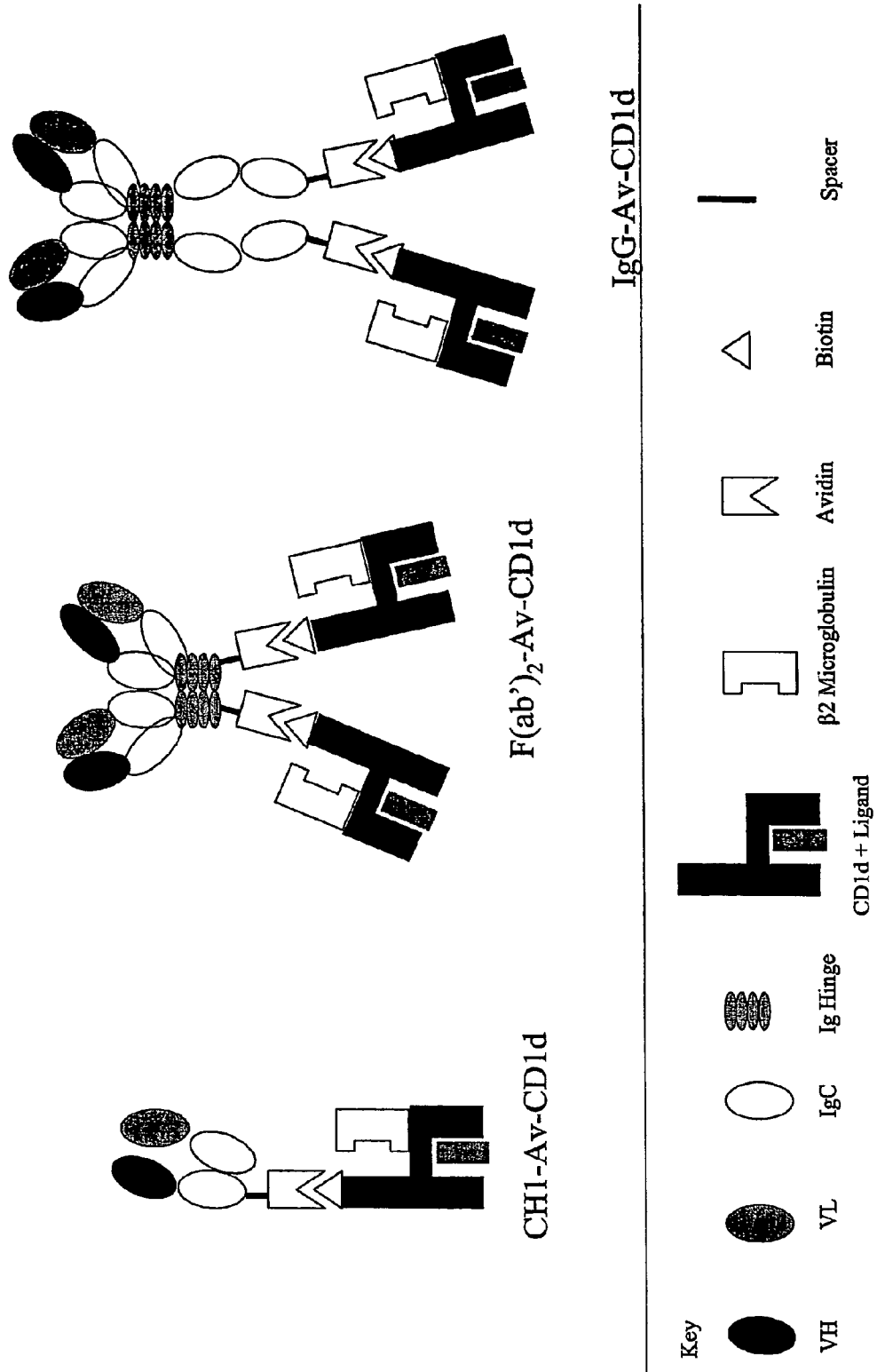

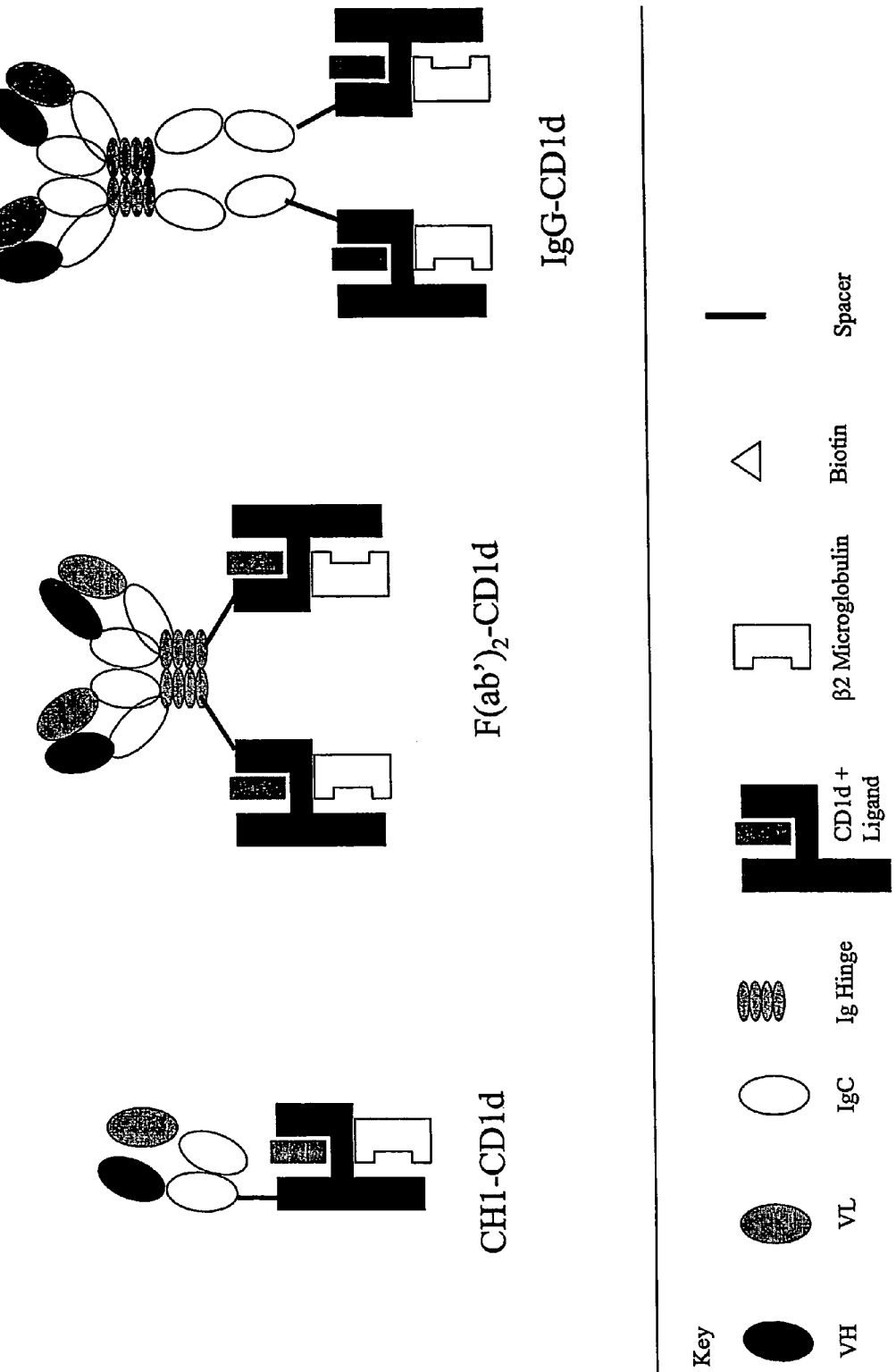
Figure 2. Antibody-CD1d fusion protein

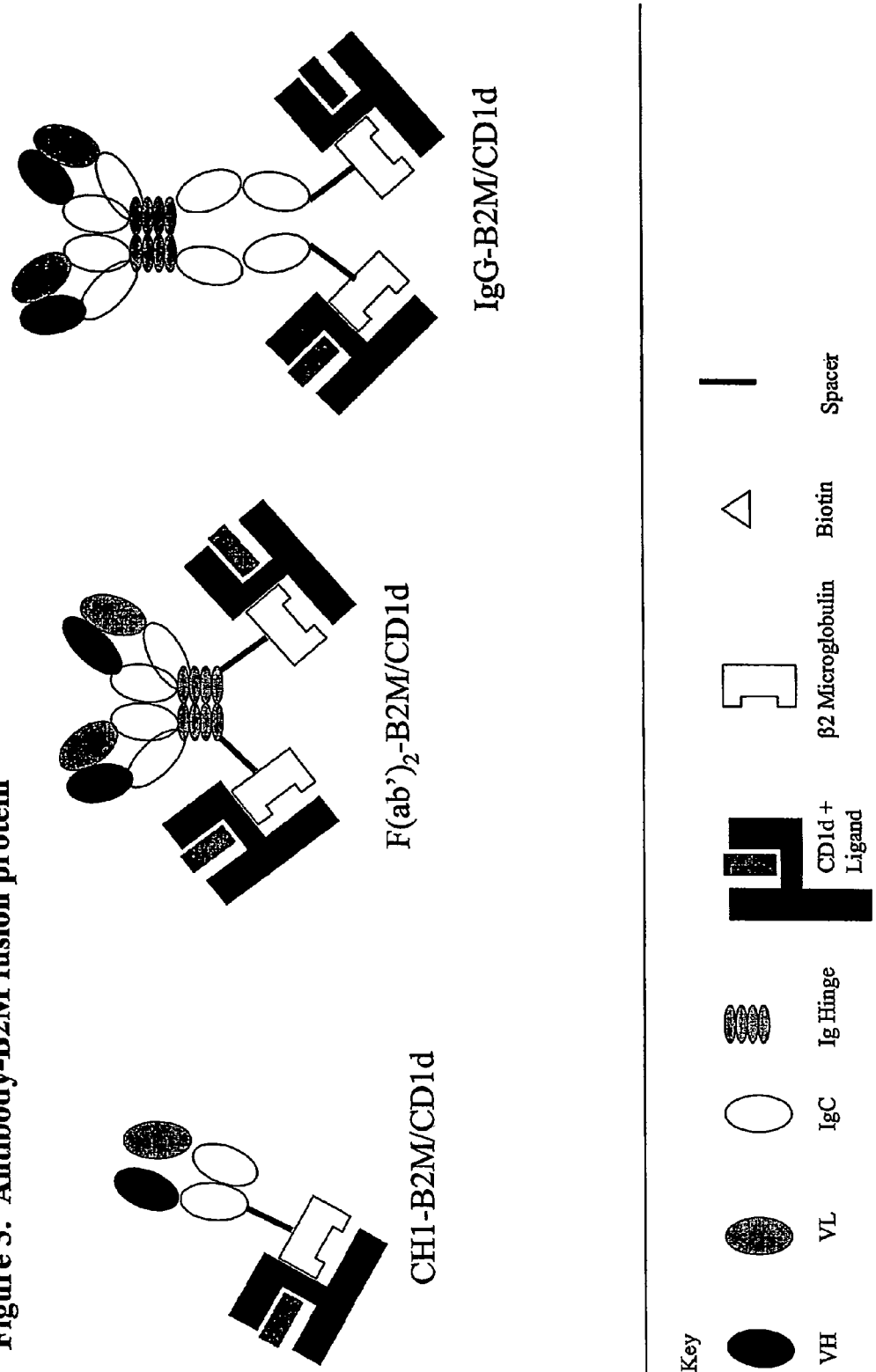

TARGETED CD1D MOLECULES

CROSS-REFERENCE TO RELATED APPLICATIONS

Not applicable.

BACKGROUND OF THE INVENTION

Field of the Invention

The invention generally relates to the field of immunology.

Background Art

The natural immune system strikes a complex balance between highly aggressive, protective immune responses to foreign pathogens and the need to maintain tolerance to normal tissues. In recent years there has been increasing recognition that interactions among many different cell types contribute to maintaining this balance. Such interactions can, for example, result in polarized responses with either production of pro-inflammatory cytokines by TH1 type T cells or production of interleukin-4 (IL4) by TH2 type T cells that suppress TH1 activity. In a number of different animal models, T cell polarization to TH1 has been shown to favor protective immunity to tumors or infectious pathogens whereas T cell polarization to TH2 can be a critical factor in preventing development of cell-mediated autoimmune disease. The conditions that determine whether immune stimulation will result in aggressive cell-mediated immunity or in down regulation of such responses are highly localized in the sense that each tissue is comprised of a distinctive set of antigen presenting cells (APC) and lymphocyte lineages that interact to favor different immune responses. For example, under optimal conditions, the dendritic cells (DC) localized in a normal tissue may represent predominantly a lineage and stage of maturation that favors tolerogenic interactions and serves as a barrier to cell-mediated autoimmunity whereas a tumor or site of infection will attract mature myeloid dendritic cells that stimulate potent cell-mediated immune responses.

CD1d-restricted NKT cells are a unique class of non-conventional T cells that appear to play an important role in defining the outcome of immune stimulation in the local environment. They share with the larger class of NKT cells the expression of markers of both the T cell and natural killer (NK) cell lineages although several studies suggest that expression of NK markers such as CD161 and NKG2d by NKT cells is a function of both stage of maturation and state of activation (Chen et al., J Immunol 1997; 158: 5112-9). As such, NKT cells are considered as part of innate immunity like NK cells and in humans their frequency in normal individuals can be as high as 2.0% of total T lymphocytes (Gumperz et al., 2002. J Exp Med 195:625; Lee et al., 2002. J Exp Med 195:637).

CD1d-restricted NKT cells are distinguished from other NKT cells by their specificity for lipid and glycolipid antigens presented by the monomorphic MHC class Ib molecule, CD1d (Kawano et al., Science 278 (1997), pp. 1626-16292). CD1d is a non-MHC encoded molecule that associates with $\beta$2-microglobulin and is structurally related to classical MHC class I molecules. In contrast to MHC class I and class II molecules that sample peptides from the cytosol and endocytic compartments and transport them to the cell surface where they can be recognized by T cells, CD1d has a hydrophobic antigen-binding pocket that is specialized for binding the hydrocarbon chains of lipid tails or hydrophobic peptides (Zeng et al., Science 277 (1997), pp. 339-345). CD1d is known to bind a marine sponge derived $\alpha$-glycosylated sphingolipid, $\alpha$-galactosylceramide ($\alpha$-GalCer), and related molecules such as sphingolipids with $\alpha$-linked galactose or glucose but not mannose (Kawano et al., Science 278 (1997), pp. 1626-1629; and Zeng et al., Science 277 (1997), pp. 339-345). As discussed below, the ability to activate many CD1d-restriced NKT cells by stimulation with $\alpha$-GalCer or related molecules bound to CD1d of antigen presenting cells has greatly facilitated functional analysis of this non-conventional T cell subset. In the absence of inflammation, CD1d-restricted NKT cells have been shown to localize preferentially in certain tissues like thymus, liver and bone marrow (Wilson et al., 2002. Trends Mol Med 8:225) and antitumor activity of NKT cells has been mainly investigated in mouse liver metastasis.

NKT cells have an unusual ability of secreting both TH1 and TH2 cytolines and potent cytotoxic as well as regulatory functions have been documented in inflammation, autoimmunity and tumor immunity (Bendelac et al., 1995 Science 268:863; Chen and Paul. 1997. J Immunol 159:2240; and Exley et al., 1997. J Exp Med 186:109). Distinct functional subsets of NKT cells have been characterized as regards their cytolines profiles, expression of several NK receptors, tissue segregation and CD1d dependance (Gumperz et al., 2002. J Exp Med 195:625; Lee et al., 2002. J Exp Med 195:637; Eberl et al., 1999. J Immunol 162:6410; and MacDonald, 2002, Curr Opin Immunol 14:250).

Among the CD1d-restricted NKT cells is a subset that expresses a highly conserved $\alpha\beta$T cell receptor (TCR). In man this invariant TCR is comprised of V$\alpha$24J$\alpha$15 in association with V$\beta$11 whereas in mice the receptor comprises the highly homologous V$\alpha$14J$\alpha$18 and V$\beta$8.2. Other CD1d-restricted NKT cells express more variable TCR Both TCR invariant and TCR variant classes of CD1d-restricted T cells can be detected by binding of CD1d-tetramers loaded with $\alpha$-GalCer (Benlagha et al., J Exp Med 191 (2000), pp. 1895-1903; Matsuda et al., J Exp Med 192 (2000), pp. 741-754; and Karadimitris et al., Proc Natl Acad Sci USA 98 (2001), pp. 3294-3298). CD1d-restricted NKT cells, as defined in this application (CD1d-NKT), include cells that express either invariant or variant TCR and that bind or are activated by CD1d loaded with either $\alpha$-GalCer or with related sphingolipids that have $\alpha$-linked galactose or glucose including molecules such as OCH, which differs from $\alpha$-GalCer by having a shortened long-chain sphingosine base (C5 vs. C14) and acyl chain (C24 vs. C26) (Miyamoto et al., Nature 2001 413:531-4). A common feature of CD1d-NKT cells is that, in contrast to conventional T cells, these lymphocytes often have a surface phenotype (CD44hiCD62L-CD69+) that is characteristic of recently activated or memory T cells. This striking phenotype has been explained by an in vivo autoreactivity of these T cells to still unknown autologous ligands presented by CD1d (Kronenberg and Gapin. 2002 Nat Rev Immunol 2:557).

CD1d-NKT have been shown to have direct cytotoxic activity against targets that express CD1d. It is likely, however, that the effect of CD1d-NKT on immune responses is amplified through recruitment of other lymphocytes either by direct interaction or, perhaps even more importantly, by indirect recruitment through interaction with DC. CD1d-NKT have the unique ability to secrete large quantities of IL-4 and IFN-$\gamma$ early in an immune response. Secretion of IFN-$\gamma$ induces activation of DC which produce interleukin-12 (IL-12). IL-12 stimulates further IFN-$\gamma$ secretion by NKT cells and also leads to activation of NK cells which secrete more IFN-$\gamma$.

Since CD1d-NKT are able to rapidly secrete large amounts of both IL-4 and IFN-γ, the polarization of immune responses will depend on whether the effect of pro-inflammatory IFN-γ or anti-inflammatory IL-4 cytokines predominate. This has been reported to be, in part, a function of the relative frequency of different subsets of CD1d-NKT. These subsets include (i) an invariant CD1d-NKT population that is negative for both CD4 and CD8 and that gives rise to predominantly a TH1 type response including secretion of pro-inflammatory IFN-γ and TNF-α and (ii) a separate population of CD1d-NKT that is CD4+ and that gives rise to both a TH1 type and TH2 type response including secretion of the anti-inflammatory Th2-type cytokines IL-4, IL-5, IL-10 and IL-13 (Lee et al., J Exp Med 2002; 195: 637-41; and Gumperz et al., J Exp Med 2002; 195: 625-36). Local factors that influence activation of CD1d-NKT subsets include the cytokine environment and, importantly, the DC that are recruited to that environment.

The availability of a defined antigen, αC-GalCer, that can be employed to specifically activate the CD1d-NKT cell subset has made it possible to examine the role of these non-conventional T cells in a variety of immune responses. Administration of the α-GalCer lipid antigen has a dramatic effect on a number of different microbial infections, including protective effects in murine malaria, fungal and hepatitis B virus infections (Kakimi et al, J Exp Med 192 (2000), pp. 921-930; Gonzalez-Aseguinolaza et al., Proc Natl Acad Sci USA 97 (2000), pp. 8461-8466; and Kawakami et al., Infect Immun 69 (2001), pp. 213-220). Dramatic effects of administration of α-GalCer have also been observed in animal models of tumor immunity. Stimulation with α-GalCer or with cytokines like IL-12 suppresses lung and liver metastases in an NKT dependent manner as shown by loss of protection in mice that do not develop CD1d-NKT because they are deficient in CD1d or in the NKT TCRα chain that is dominantly expressed in CD1d-NKT (Smyth et al., 2002. Blood 99:1259; Hayakawa et al., Eur J Immunol 31:1720; Takeda et al., Int Immunol 12:909). One study (Cui et al., Science 278 (1997), pp. 1623-1626) demonstrated that the antitumor response to melanomas observed in tumor-bearing mice treated with IL-12 is solely due to NKT cells. In contrast to normal mice with CD1d-NKT cells, IL-12 treated tumor-bearing mice deficient in the Jα15 gene (which are deficient in NKT cells, since most mouse CD1d-NKT cells express Jα15 positive invariant TCR) could not control B16 melanoma growth and metastases.

A number of indirect mechanisms contribute to the protective effect of CD1d-NKT cells. Activation of NKT cells by administration of α-GalCer in vivo results in concomitant activation of NK cells (Eberl and MacDonald, Eur. J. Immunol. 30 (2000), pp. 985-992; and Carnaud et al., J. Immunol. 163 (1999), pp. 4647-4650). In mice deficient in NKT cells, α-GalCer is unable to induce cytotoxic activity by NK cells. NKT cells also enhance the induction of classical MHC class I restricted cytotoxic T cells (Nishimura et al., Int Immunol 2000; 12: 987-94; and Stober et al., J Immunol 2003; 170:2540-8).

The participation of NKT cells at the earliest stages of the protective immune response to many pathogens (infections (Kakimi et al, J Exp Med 192 (2000), pp. 921-930; Gonzalez-Aseguinolaza et al., Proc Natl Acad Sci USA 97 (2000), pp. 8461-8466; Kawakami et al., Infect Immun 69 (2001), pp. 213-220; and Bendelac and Medzhitov, J Exp Med 2002; 195: F19-23) and tumors (Kobayashi et al., Oncol Res 1995; 7: 529-34; and Smyth et al., Curr Opin Immunol 2002; 14:165-71) is a reflection of their direct cytotoxic activity as well as their important contribution to general mobilization of an aggressive cell-mediated immune response. Extensive evidence suggests, however, that NKT cells also function to suppress autoimmunity (Hong et al., Nature Med 2001; 7: 1052-6; Beaudoin et al., Immunity 2002; 17: 725-36; Wilson et al., Trends Mol Med 2002; 8: 225-31; Shi et al., Proc Natl Acad Sci USA 2001; 98: 6777-82; Naumov et al., Proc Natl Acad Sci USA 2001; 98: 13838-43; Sharif et al., Nature Med 2001; 7: 1057-62; Wang et al., J Exp Med 2001; 194: 313-20; Jahng et al., J Exp Med 2001; 194: 1789-99; Singh et al., J Exp Med 2001; 194:1801-11), maintain immune privilege (Sonoda et al., J Exp Med 1999; 190: 1215-26; Hong and Van Kaer, J Exp Med 1999; 190: 1197-1200), and support engraftment of transplanted tissues (Seino et al., Proc Natl Acad Sci USA 2001; 98: 2577-81; Zeng et al., J Exp Med 1999; 189: 1073-81). These include experiments in which administration of α-GalCer has been shown to protect against autoimmune diabetes in non-obese diabetic (NOD) mice (Hong et al., Nature Med 2001; 7: 1052-6; Wilson et al., Trends Mol Med 2002; 8: 225-31; Sharif et al., Nature Med 2001; 7: 1057-62) and against experimental autoimmune encephalomyelitis (EAE), a murine model of demyelinating disease (Jahng et al., J Exp Med 2001; 194: 1789-99; and Singh et al., J Exp Med 2001; 194: 1801-11). Conversely, deletion of NKT cells results in exacerbation or potentiation of disease in these models (Shi et al., Proc Natl Acad Sci USA 2001; 98: 6777-82). Parallel studies of the frequency of CD1d-NKT cells in human cancer and certain autoimmune diseases have demonstrated that a deficiency in such T cells is associated with progressive disease (Tahir et al. J. Immunol. 167:4046-50,2001; Sharif et al. J. Mol. Med. 80:290-300,2002; Sumidha et al. J. Exp. Med. 182:1163-68,1995; Mes et al. J. Immunol. 164:4375-81,2000; van der Vliet et al. Clin. Immunol. 100:144-148,2001). In contrast, some autoimmune diseases, including myasthenia gravis (Reinhardt et al. Neurology 52:1485-87,1999), psoriasis (Bonish, J. Immunol. 165:4076-85,2000), ulcerative colitis (Saubermann et al. Gastroenterology 119:119-128, 2000), and primary biliary cirrhosis (Kita et al. Gastroenterology 123:1031-43,2002) may have an etiology that reflects excessive IL-4 and IFN-γ production by CD1d-NKT cells. In the case of psoriasis this appears to be related to overexpression of CD1d in keratinocytes of chronic, active psoriatic plaques.

The divergent pro-inflammatory and anti-inflammatory effects of CD1d-NKT cells in different circumstances have been attributed to different functional subsets of CD1d-NKT and dendritic cells and to differences in the representation of these subsets in the local tissue environment. An interesting example is a study demonstrating that transfer of myeloid DC derived from pancreatic lymph nodes, but not from inguinal lymph nodes, of mice treated systemically with α-GalCer completely protects NOD female mice from diabetes [30]. As a result of this potential for divergent effects, systemic activation of CD1d-NKT, for example by administration of α-GalCer, may have an undesirable outcome in the treatment of specific disease. There is a need, therefore, for a means of targeted activation of CD1d-NKT in a specific local environment and/or by targeted interaction with a defined subset of dendritic cells.

SUMMARY OF THE INVENTION

The present invention provides compounds useful for modulating, i.e., either inhibiting or stimulating, an immune response. The compounds of the invention comprise one or more CD1d complexes linked to an antibody or fragment thereof specific for a cell surface marker. The CD1d complexes comprise a CD1d molecule or fragment thereof, a β2-microglobulin molecule or fragment thereof, and may further comprise a lipid, glycolipid, or hydrophobic peptide linked to the CD1d molecule. In certain embodiments, the compounds of the invention further comprise a costimulatory molecule.

The CD1d complexes may be directly linked or fused to the antibody, either directly or through a linker sequence or molecule. In certain embodiments, the CD1d molecules are linked to the antibody or fragment thereof through a multivalent compound.

In certain embodiments, the antibody is specific for a cell surface marker of a tumor cell. In other embodiments, the antibody is specific for a cell surface marker of a target of autoimmunity. In other embodiments, the antibody is specific for a cell surface marker of infected cells. This marker may be either directly encoded by the pathogen or induced by infection of the host cell as taught by WO 0227027, published 4 Apr. 2002, the disclosure of which is incorporated by reference herein. In still other embodiments, the antibody is specific for a cell surface marker of a dendritic cell.

Also provided are methods of modulating, i.e., either stimulating or inhibiting, an immune response, comprising administering to an animal an effective amount of a compound or composition of the invention. In certain embodiments, an immune response against tumor cells is stimulated by administering a compound of the invention to an animal. In other embodiments, an autoimmune response is inhibited by administering a compound of the invention to an animal.

It is to be understood that both the foregoing summary and the following detailed description are exemplary and explanatory and are intended to provide further explanation of the invention as claimed.

BRIEF DESCRIPTION OF THE DRAWINGS/FIGURES

The present invention will be described with reference to the accompanying drawings, wherein like reference numbers indicate identical or functionally similar elements. Also, the leftmost digit(s) of the reference numbers identify the drawings in which the associated elements are first introduced.

FIG. 1: Schematic representation of Antibody-avidin fusion protein/biotinylated CD1d. In three separate embodiments, CD1d with bound ligand is biotinylated at the CD1d carboxyl terminus and binds to a fusion protein of Fab-avidin, F(ab')2-avidin, or IgG-avidin. All 3 fusion proteins are represented with avidin bound at the carboxyl terminus of the immunoglobulin heavy chain or fragment thereof. As described below, alternatives include avidin fusion to the carboxyl terminus of the immunoglobulin light chain.

FIG. 2: Schematic representation of Antibody-CD1d fusion protein. In three separate embodiments, CD1d with bound ligand is fused directly to Fab, F(ab')2, or full IgG. All 3 fusion proteins are represented with the amino terminus of CD1d fused to the carboxyl terminus of the immunoglobulin heavy chain or fragment thereof. As described below, alternatives include CD1d fusion to the carboxyl terminus of the immunoglobulin light chain or to amino terminus of either the immunoglobulin light chain or immunoglobulin heavy chain or fragment thereof.

FIG. 3: Schematic representation of Antibody-B2M fusion protein associated with CD1d. In three separate embodiments, β2-microglobulin is fused to the carboxyl terminus of Fab, F(ab')2, or full IgG. All 3 fusion proteins are represented with the amino terminus of β2-microglobulin fused to the carboxyl terminus of the immunoglobulin heavy chain or fragment thereof. As described below, alternatives include β2-microglobulin fusion to the carboxyl terminus of the immunoglobulin light chain or to amino terminus of either the immunoglobulin light chain or immunoglobulin heavy chain or fragment thereof. In all cases, the heavy chain of CD1d associates with the antibody-β2-microglobulin fusion protein and binds ligand. As taught by WO 9964597 published 16 Dec. 1999 and incorporated herein by reference, it is possible to introduce mutations into β2-microglobulin that increase affinity for the class I heavy chain so as to facilitate assembly and increase stability of the CD1d complex.

DETAILED DESCRIPTION OF THE INVENTION

The present invention provides compounds which are useful for modulating, i.e., either inhibiting or stimulating, an immune response. The compounds comprise one or more CD1d complexes linked to an antibody or fragment thereof specific for a cell surface marker. The compounds are useful for stimulating desirable immune responses, for example, immune responses against infectious agents or cancer; or for inhibiting undesirable immune responses, such as allergic responses, allograft rejections, and autoimmune diseases. The present invention targets a CD1d molecule to particular cells by linking one or more CD1d complexes to an antibody or fragment thereof specific for a surface antigen of the targeted cell type. Depending on the targeted cell type, this will lead to either very efficient stimulation or inhibition of antigen specific T cell activity.

Previously, antibodies coupled to classical MHC class I molecules have been employed to target these MHC class I:peptide complexes to tumors for the purpose of activating classical MHC class I restricted cytotoxic T cells. (Robert et al., 2000, Eur. J. Immunol. 30: 3165-3170; Robert et al., 2001, Cancer Immunity, 1:2-15; and Donda et al., 2003, Cancer Immunity 3:11). A significant limitation of that method is that it does not lead to activation of the important class of non-conventional CD1d-NKT cells with their unique regulatory functions. In addition, because of the extensive polymorphism of classical MHC class I, such a strategy would require coupling of antibodies to many different MHC molecules in order to be suitable for application to a large and heterogeneous population. In marked contrast, the monomorphic CD1d molecule is suitable for activation of a broad spectrum of CD1d-NKT in an entire species. Moreover, targeted CD1d has application as a diagnostic or therapeutic agent not only for cancer and infectious diseases but also for a large class of autoimmune and inflammatory diseases that result from a failure to down modulate cell-mediated immune responses.

The present invention provides a means of targeting an activation or inhibitory signal for CD1d-NKT to a specific tissue or dendritic cell subset by coupling CD1d loaded with α-GalCer or related lipid molecules to an antibody specific for a tissue antigen or for a dendritic cell marker. This strategy allows regulated expression and/or expansion of CD1d-NKT at the site of a tumor or of an infection, or in a tissue that is the target of an organ-specific autoimmune response. The combination of the powerful regulatory and effector activities of CD1d-NKT together with tissue or tumor targeting properties of specific monoclonal antibodies affords a unique means of inducing a response appropriate to a specific tissue and disease.

The CD1d complexes (both the CD1d and β2-microglobulin portions) useful in the present invention may be autologous to any mammalian or avian species, for example, primates (esp. humans), rodents, rabbits, equines, bovines, canines, felines, etc. β2-microglobulin is typically not inflammatory in vivo. However, it is preferable to employ β2-microglobulin derived from the same species as is to be vaccinated so as to reduce the risk of a xenogeneic immune response.

In one embodiment, the CD1d complexes comprise a CD1d molecule or fragment thereof, a β2-microglobulin molecule or fragment thereof, and an antigen. The antigen is a lipid, glycolipid, or hydrophobic peptide bound in the antigen binding groove of the CD1d molecule.

In certain embodiments, the compound further comprises another protein with immunological activity. Preferably, the protein with immunological activity is a costimulatory molecule, such as B7.1 or B7.2. "B7" is used herein to generically refer to either B7.1 or B7.2. Particularly preferred is the extracellular domain of B7-1 (CD80) or B7-2 (CD86) that interacts with CD28 on T- and NK-cells, for example, as an amino terminal fusion to β2-microglobulin incorporated into the structure of the assembled CD1d molecule (WO 9964597, published 16 Dec. 1999) or, alternatively, as an amino-terminal fusion to the CD1d heavy chain. CD28 acts as a costimulatory molecule on T lymphocytes, which is absolutely required in order to mediate the so-called second signal during primary T cell activation through antigen specific TCR-engagement (the complementary so-called first signal). On NK cells CD28 contributes to the induction of cytotoxicity against target cells expressing CD28 ligands (Chambers (1996) Immunity 5: 311). Like NK cells, CD1d-NKT are subject to inhibitory signals delivered by classical MHC class I molecules on the surface of interacting cells. Ikarashi et al. (J. Exp. Med. 194:1179-86,2001) have reported that in the interaction of CD28 positive NKT cells with B7 positive DC, the B7/CD28 interaction plays a critical role in overcoming the inhibitory signal otherwise delivered to NKT cells by classical MHC class I molecule expressed on the target cell surface. In this embodiment of the invention, incorporation of a B7 signaling molecule in the conjugate of the invention allows more effective and prolonged activation of CD1d-NKT cells.

Additionally, the protein with immunological activity may be a lymphokine or cytoline that modulates immune cell activation such as interleukins IL-1, IL-2, IL-3, IL-4, IL-5, IL-6, IL-10, IL-12, IL-15, IL-18; granulocyte-macrophage colony stimulating factor (GM-CSF); transforming growth factor (TGF, e.g., TGFα and TGFβ); a interferons (e.g. IFNα); β interferons (e.g. IFNβ); γ interferons (e.g. IFNγ) or lymphocyte function-associated protein, such as LFA-1 or LFA-3; or an intercellular adhesion molecule, such as ICAM-1 or ICAM-2.

The CD1d complexes are linked to the antibody through either the CD1d molecule or fragment thereof or the β2 microglobulin molecule or fragment thereof. The CD1d complexes may be linked to either the light chain or the heavy chain of the antibody. As taught by WO 9964597, published 16 Dec. 1999 and incorporated herein by reference, it is possible to introduce mutations into β2-microglobulin that increase affinity for the class I heavy chain so as to facilitate assembly and increase stability of the CD1d complex in the fusion protein.

The CD1d complexes may be linked to either the carboxyl or amino terminus of the antibody, or they may be linked to the antibody at a site other than the carboxyl or amino termini. Preferably, the CD1d complexes are linked to the carboxyl terminus of the antibody.

The attachment of the CD1d complexes to the antibody chains may be direct, i.e., without any intermediate sequence, or through a linker amino acid sequence, a linker molecule, or a chemical bond. For example, the coupling may be of a physical and/or chemical type. The antibody and CD1d complex may be coupled physically utilizing a carrier for example a Sepharose carrier (available from Pharmacia, Uppsala, Sweden) or recently developed microsphere technology. (Southern Research Institute).

Alternatively, the CD1d complexes domain and the antibodies may be linked together directly. A number of reagents capable of cross-linking proteins are known in the art, illustrative entities include: azidobenzoyl hydrazide, N-[4-(p-azidosalicylamino)butyl]-3'-[2'-pyridyldithio]propionamide), bis-sulfosuccinimidyl suberate, dimethyladipimidate, disuccinimidyltartrate, N-γ-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl]aminobenzoate, glutaraldehyde, formaldehyde and succinimidyl 4-[N-maleimidomethyl]cyclohexane-1-carboxylate.

In certain embodiments, the CD1d complexes domain may be linked in a fusion protein with the antibody. Fusion antibodies can be made using conventional recombinant nucleic acid techniques. The fusion may be direct or may contain spacers. A short linker amino acid sequence may be inserted between the CD1d complex and the antibody. The length of the linker sequence will vary depending upon the desired flexibility to regulate the degree of antigen binding and cross-linking. If a linker sequence is included, this sequence will preferably contain at least 3 and not more than 30 amino acids. More preferably, the linker is about 5, 6, 7, 8, 9, 10, 11, 12, 13, 14, 15, 20, or 25 amino acids long. Generally, the linker consists of short glycine\serine spacers, but any known amino acid may be used. Examples of linkers known to those skilled in the art include (Gly4Ser)3 (SEQ ID NO:1) and (Gly4Ser)2Gly3AlaSer (SEQ ID NO:2).

CD1d complexes fused to the carboxyl terminus of the exceptionally long IgG3 hinge region or to the CH3 domain, are especially far removed from possible interference with the antigen binding site or its ligand. Fc binding function is preserved in the compounds of this invention that are based on CH3 fusions. It is possible that this would extend the half-life of these compounds in vivo.

In certain embodiments, the CD1d complexes are linked to the antibody through a multivalent compound. The CD1d complexes may be linked to the multivalent compound through any site. In a preferred embodiment CD1d molecules are linked to the multivalent compound through the CD1d carboxyl terminus.] These compounds comprise 2 or more CD1d complexes. The compounds may comprise 2, 3, 4, 5, 6, 7, 8, 9 or 10 CD1d complexes.

Likewise, the antibody may be linked to the multivalent compound through any site. The antibody may be linked to the multivalent compound through the light chain, the heavy chain, both light chains, both heavy chains, one light chain and one heavy chain, or both light and both heavy chains and at either the amino or the carboxyl terminus. Preferably, the antibody is linked to the multivalent compound at the carboxyl terminus of the heavy chain.

Examples of multivalent compounds are chicken avidin or streptavidin (Shin, S. U. et al., *J Immunology* 158: 4797-4804 (1997)) to which biotinylated CD1d complexes are bound (Altman, J. et al, *Science* 274:94-96 (1996); Boniface, J. J. et al., *Immunity* 9:459-66 (1998)); or a leucine zipper system.

Alternatively, the Cd1d complex can be genetically modified by including sequences encoding amino acid residues with chemically reactive side chains such as Cys or His. Such amino acids with chemically reactive side chains may be positioned in a variety of positions on the CD1d complex, preferably distal to the site where β2-microglobulin and CD1d interact. Suitable side chains can be used to chemically link two or more CD1d complexes to a suitable dendrimer particle. Dendrimers are synthetic chemical polymers that can have any one of a number of different functional groups on their surface (D. Tomalia, Aldrichimica Acta 26:91:101 (1993)). Exemplary dendrimers for use in accordance with the present invention include e.g. E9 starburst polyamine dendrimer and E9 combburst polyamine dendrimer, which can link cysteine residues. The CD1d molecule is modified to introduce a cysteine residue at the carboxyl terminus. Following synthesis in eukaryotic cells, a complete cysteine modified CD1d complex is assembled in vitro in the presence of β2-microglobulin. Cysteine modified CD1d will react with the maleimide groups on the various peptide backbones with either two, three, or four modified lysine residues for formation of CD1d dimers, trimers, and tetramers. In a preferred embodiment, a carboxyl terminal cysteine modified immunoglobulin chain or fragment thereof could also be synthesized for reaction with a maleimide-modified lysine residue on the same backbone peptide and at the same time as the cysteine modified CD1d.

Cochran, J. R. et al., *Immunity* 12:241-50 (2000) describe the use of chemically synthesized peptide-based cross-linking reagents in which two or more thiol-reactive maleimide groups are linked to lysine side chains in a flexible peptide of 8 to 19 residues containing glycine, serine, and glutamic acid in addition to the modified lysine residues. An isolated CD1d molecule is modified to introduce a cysteine residue at the carboxyl terminus. Cysteine modified CD1d molecules react with the maleimide groups on the various peptide backbones with either two, three, or four modified lysine residues for formation of dimers, trimers, and tetramers.

Another means of assembling polymeric complexes on specific antibody is to exploit the observation that defined amino acid substitutions in the GCN4 leucine zipper dimerization domain results in formation of highly stable trimeric and tetrameric structures of the synthetic peptide (Harbury, P. B. et al., *Science* 262:1401-7 (1993)). Pack, P. et al. *J. Mol. Biol.* 246:28-34 (1995) constructed tetravalent miniantibodies by fusing the modified GCN4-zipper to the carboxyl terminus of a single-chain Fv fragment via a flexible hinge region. Several additional modifications of the fusion protein improved yield from bacterial synthesis. Addition of a carboxyl terminal tag would facilitate purification. Targeted tetravalent CD1d could be assembled from a mixture of single chain antibody and CD1d complexes each separately fused through a hinge region to the modified GCN4-zipper motif.

The alternative embodiments of this invention, direct fusion of antibody and CD1d complexes or indirect association of antibody and CD1d complexes through a multivalent entity, are respectively advantageous in different situations. The direct fusion simplifies production of the compound while the multivalent entity, as indicated above, can present a larger number of more diverse ligands. In both cases it is desirable to design products that induce minimal immune reactivity. In the case of direct immunoglobulin- CD1d fusion proteins, this is accomplished by employing species compatible antibodies and CD1d complexes joined by simple linkers with a relatively non-immunogenic composition. Multivalent entities may be similarly selected to minimize immunogenicity. Chicken avidin is thought to be relatively nonimmunogenic because of its high concentration in egg products and the well-known propensity of oral infusion to induce immune tolerance (Shin, S. U. et al., J. Immunology 158: 4797-4804 (1997)). It may, in addition, be possible to develop protocols, including some that employ compounds of this invention, that induce specific tolerance to the multivalent entity.

The attachment site on the CD1d complex or antibody for binding to a multivalent compound may be naturally occurring, or may be introduced through genetic engineering. The site will be a specific binding pair member or one that is modified to provide a specific binding pair member, where the complementary pair has a multiplicity of specific binding sites. Binding to the complementary binding member can be a chemical reaction, epitope-receptor binding or hapten-receptor binding where a hapten is linked to the subunit chain.

In a preferred embodiment, the CD1d, β2 microglobulin, or antibody, contain an amino acid sequence which is a recognition site for a modifying enzyme. Modifying enzymes include BirA, various glycosylases, farnesyl protein transferase, and protein kinases. The group introduced by the modifying enzyme, e.g. biotin, sugar, phosphate, farnesyl, etc. provides a complementary binding pair member, or a unique site for further modification, such as chemical cross-linking, biotinylation, etc. that will provide a complementary binding pair member.

For example, the CD1d molecule may be engineered to contain a site for biotinylation, for example a BirA-dependent site. The antibody or fragment thereof can be linked to avidin either directly or indirectly. Direct linkage is accomplished by making an antibody-avidin fusion protein through genetic engineering as described in, for example, Shin et al., Shin, S.-U. et al., J. Immunol. 158:4797-4804 (1997); and Penichet et al., J. Immunol. 163:4421-4426.

The CD1d molecule may contain some or all of the amino acids from the transmembrane domain. Preferably, not more than about 20, 19, 18, 17, 16, 15, 14, 13, 12, 11, 10, 9, 8, 7, 6, 5, 4, 3, 2 or 1, and preferably none of the amino acids of the transmembrane domain will be included.

Additionally, fragments of $\beta_2$-microglobulin are useful in the present invention. To be useful in the present invention, the fragment of $\beta_2$-microglobulin would have to retain the ability to associate with the CD1d molecule. Preferably, not more than about 20, 19, 18, 17, 16, 15, 14, 13, 12, 11, 10, 9, 8, 7, 6, 5, 4, 3, 2 or 1, and preferably none of the amino acids of $\beta_2$-microglobulin will be deleted.

One may wish to introduce a small number of amino acids at the polypeptide termini of either the CD1d molecule or the $\beta_2$-microglobulin, usually not more than 20, 19, 18, 17, 16, 15, 14, 13, 12, 11, 10, 9, 8, 7, 6, 5, 4, 3, 2 or 1. The deletion or insertion of amino acids will usually be as a result of the needs of the construction, providing for convenient restriction sites, addition of processing signals, ease of manipulation, improvement in levels of expression, or the like. In addition, one may wish to substitute one or more amino acids with a different amino acid for similar reasons, usually not substituting more than about 10, 9, 8, 7, 6, 5, 4, 3, 2 or 1 amino acids in any one domain.

The CD1d molecule and β$_2$-microglobulin may be separately produced and allowed to associate to form a stable heteroduplex complex, or both of the subunits may be expressed in a single cell.

CD1d and β2-microglobulin molecules useful in the compounds of the present invention may be isolated from a multiplicity of cells, e.g., transformed cell lines JY, BM92, WIN, MOC, and MG, and CHO using a variety of techniques known to those skilled in the art.

Additionally, the amino acid sequences of CD1 d and β2-microglobulin are known, and the genes have been cloned, therefore, the proteins can be made using recombinant methods. For example, CD1d molecule is synthesized and the amino terrini coding sequence can be arbitrarily chosen to facilitate the ligation of the coding region for an antibody chain or fragment or a binding intermediate. The coding sequence for the CD1d and β$_2$ microglobulin chains or their fusion products are then inserted into expression vectors, expressed separately in an appropriate host, such as *E. coli*, yeast, insect cells, mammalian cells or other suitable cells, and the recombinant proteins obtained are recombined in the presence of the CD1d lipid, glycolipid (e.g. α-GalCer) or hydrophobic peptide ligand.

Antigens useful within the present invention include any lipid, glycopeptide or peptide which is capable of modulating an immune response in an animal when presented in conjunction with a CD1d molecule. The antigens may be derived from foreign antigens or from autoantigens. Further, the antigens may be synthetic. Particularly preferred as an antigen is αGalCer.

The compounds of the invention may contain a homogenous or heterogeneous population of antigens and/or costimulatory molecules. That is, each CD1d molecule in the compound may be linked to the same antigen or each CD1d molecule may be linked to different antigen. Likewise, the CD1d complex may be linked to the same costimulatory molecule or different CD1d complex β2-microglobulin molecules may be linked to different costimulatory molecules. Alternatively, some of the CD1d molecules may be linked to an antigen, while some of the CD1d molecules may be linked to a costimulatory molecule.

Antibodies are constructed of one, or several, units, each of which consists of two heavy (H) polypeptide chains and two light (L) polypeptide chains. The H and L chains are made up of a series of domains. The L chains, of which there are two major types (κ and λ), consists of two domains. The H chains are of several types, including μ, δ, and γ (of which there are several subclasses), α and ε. In humans, there are eight genetically and structurally identified antibody classes and subclasses as defined by heavy chain isotypes: IgM, IgD, IgG3, IgG1, IgG2, IgG4, IgE, and IgA. Further, for example, "IgG" means an antibody of the G class, and that, "IgG1" refers to an IgG molecules of subclass 1 of the G class. IgG1 antibodies, like all antibodies of the IgG class, are comprised of 4 domains, one of which is variable and the other 3 are constant. An Fab antibody fragment is comprised of an intact light chain and a truncated heavy chain that each comprise two domains, one variable and one constant.

As used herein, the term "antibody" (Ab) or "monoclonal antibody" (MAb) is meant to include intact molecules as well as antibody portions (such as, for example, Fab and F(ab')2 portions and Fv fragments) which are capable of specifically binding to a cell surface marker. Such portions are typically produced by proteolytic cleavage, using enzymes such as papain (to produce Fab portions) or pepsin (to produce F(ab')2 portions). Especially preferred in the compounds of the invention are Fab portions. Alternatively, antigen-binding portions can be produced through the application of recombinant DNA technology.

The immunoglobulin may be a "bifunctional" or "hybrid" antibody, that is, an antibody which may have one arm having a specificity for one antigenic site, such as a tumor associated antigen while the other arm recognizes a different target, for example, an immunologically active cytokine or lymphokine, or CD1d. In any case, the hybrid antibodies have a dual specificity, preferably with one or more binding sites specific for an antigen expressed on the surface of a target cell, for example, an antigen associated with a tumor, an infectious organism, or antigenic marker of another disease state.

In addition, the immunoglobin may be a single chain antibody ("SCA"). These may consist of single chain Fv fragments ("scFv") in which the variable light ("V[L]") and variable heavy ("V[H]") domains are linked by a peptide bridge or by disulfide bonds. Also, the immunoglobulin may consist of single V[H]domains (dAbs) which possess antigen-binding activity. See, e.g., G. Winter and C. Milstein, Nature 349:295 (1991); R. Glockshuber et al., Biochemistry 29:1362 (1990); and, E. S. Ward et al., Nature 341:544 (1989).

Also preferred for use in the present invention are chimeric monoclonal antibodies, preferably those chimeric antibodies having specificity toward a tumor associated surface membrane antigen, a surface membrane antigen of a tissue or organ affected by autoimmune disease, or an antigen of a pathogen infected cell. As used in this example, the term "chimeric antibody" refers to a monoclonal antibody comprising a variable region, i.e. binding region, from one source or species and at least a portion of a constant region derived from a different source or species, usually prepared by recombinant DNA techniques. Chimeric antibodies comprising a murine variable region and a human constant region are preferred in certain applications of the invention, particularly human therapy, because such antibodies are readily prepared and may be less immunogenic than purely murine monoclonal antibodies. Such murine/human chimeric antibodies are the product of expressed immunoglobulin genes comprising DNA segments encoding murine immunoglobulin variable regions and DNA segments encoding human immunoglobulin constant regions. Other forms of chimeric antibodies encompassed by the invention are those in which the class or subclass has been modified or changed from that of the original antibody. Such "chimeric" antibodies are also referred to as "class-switched antibodies". Methods for producing chimeric antibodies involve conventional recombinant DNA and gene transfection techniques now well known in the art. See, e.g., Morrison, S. L. et al., Proc. Natl Acad. Sci. 81:6851 (1984).

Encompassed by the term "chimeric antibody" is the concept of "humanized antibody", that is those antibodies in which the framework or "complementarity" determining regions ("CDR") have been modified to comprise the CDR of an immunoglobulin of different specificity as compared to that of the parent immunoglobulin. In a preferred embodiment, a murine CDR is grafted into the framework region of a human antibody to prepare the "humanized antibody". See, e.g., L. Riechmann et al., Nature 332:323 (1988); M. S. Neuberger et al., Nature 314:268 (1985). Particularly preferred CDR'S correspond to those representing sequences recognizing the antigens noted above for the chimeric and bifunctional antibodies. The reader is referred to the teaching of EPA 0 239 400 (published Sep. 30, 1987), for its teaching of CDR modified antibodies. See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).

Most preferably, fully human antibodies or fragments thereof are used in the compounds of the invention, preferably those fully human antibodies having specificity toward a tumor associated surface membrane antigen, a surface membrane antigen of a tissue or organ affected by autoimmune disease, or an antigen of a pathogen infected cell. Methods have been described for selection of fully human antibodies in human immunoglobulin transgenic mice, from libraries of human immunoglobulin genes constructed in phage and expressed in bacteria or constructed in a mammalian viral expression vector for expression in mammalian cells, and from human hybridoma cells. A method for selection of fully human antibodies from libraries of human immunoglobulin genes constructed in vaccinia virus is described in Zauderer, M. et al. WO 01/72995, published 4 Oct. 2001, the disclosure of which is incorporated by reference herein.

One skilled in the art will recognize that a bifunctional-chimeric antibody can be prepared which would have the benefits of lower immunogenicity of the chimeric, humanized or fully human antibody, as well as the flexibility, especially for therapeutic treatment, of the bifunctional antibodies described above. Such bifunctional-chimeric antibodies can be synthesized, for instance, by chemical synthesis using cross-linking agents and/or recombinant methods of the type described above. In any event, the present invention should not be construed as limited in scope by any particular method of production of an antibody whether bifunctional, chimeric, bifunctional-chimeric, humanized, fully human or an antigen-recognizing fragment or derivative thereof.

In addition, the invention encompasses within its scope immunoglobulins (as defined above) or immunoglobulin fragments to which are fused active proteins, for example, an enzyme of the type disclosed in Neuberger et al., PCT application, WO86/01533, published Mar. 13, 1986. The disclosure of such products is incorporated herein by reference.

As noted, "bifunctional", "fused", "chimeric" (including humanized), "fully human", and "bifunctional-chimeric" (including humanized) or "bifunctional-fully human" antibody constructions also include, within their individual contexts constructions comprising antigen recognizing fragments. As one skilled in the art will recognize, such fragments could be prepared by traditional enzymatic cleavage of intact bifunctional, chimeric, humanized, fully human or chimeric-bifunctional or fully human-bifunctional antibodies. If, however, intact antibodies are not susceptible to such cleavage, because of the nature of the construction involved, the noted constructions can be prepared with immunoglobulin fragments used as the starting materials; or, if recombinant techniques are used, the DNA sequences, themselves, can be tailored to encode the desired "fragment" which, when expressed, can be combined in vivo or in vitro, by chemical or biological means, to prepare the final desired intact immunoglobulin "fragment". It is in this context, therefore, that the term "fragment" is used.

Furthermore, as noted above, the immunoglobulin (antibody), or fragment thereof, used in the present invention may be polyclonal or monoclonal in nature. Monoclonal antibodies are the preferred immunoglobulins, however. The preparation of such polyclonal or monoclonal antibodies now is well known to those skilled in the art who, of course, are fully capable of producing useful immunoglobulins which can be used in the invention. See, e.g., G. Kohler and C. Milstein, Nature 256:495 (1975). Kohler et al., Nature 256:495 (1975); Kohler et al., Eur. J. Immunol. 6:511 (1976); Kohler et al., Eur. J. Immunol. 6:292 (1976); Hammerling et al., In: Monoclonal Antibodies and T-Cell Hybridomas, Elsevier, N.Y., pp. 563-681 (1981)). In general, such procedures involve immunizing an animal (preferably a mouse) with a protein antigen or, more preferably, with a protein-expressing cell. Suitable cells can be recognized by their capacity to bind antibody. Such cells may be cultured in any suitable tissue culture medium; however, it is preferable to culture cells in Excell hybridoma medium (JRH Biosciences, Lenexa, Kans.) with 5% fetal bovine serum. The splenocytes of such immunized mice are extracted and fused with a suitable myeloma cell line. Any suitable myeloma cell line may be employed in accordance with the present invention; however, it is preferable to employ the parent myeloma cell line (SP2O), available from the American Type Culture Collection, 10801 University Boulevard, Manassas, Va. 20110-2209. After fusion, the resulting hybridoma cells are selectively maintained in HAT medium, and then cloned by limiting dilution as described by Wands et al., Gastroenterology 80:225-232 (1981). The hybridoma cells obtained through such a selection are then assayed to identify clones which secrete antibodies capable of binding the antigen.

In addition, hybridomas and/or monoclonal antibodies which are produced by such hybridomas and which are useful in the practice of the present invention are publicly available from sources such as the American Type Culture Collection ("ATCC") 10801 University Boulevard, Manassas, Va. 20110-2209 or, commercially, for example, from Boehringer-Mannheim Biochemicals, P.O. Box 50816, Indianapolis, Ind. 46250.

The antibodies of the present invention may be prepared by any of a variety of methods. For example, cells expressing the cell surface marker or an antigenic portion thereof can be administered to an animal in order to induce the production of sera containing polyclonal antibodies. In a preferred method, a preparation of protein is prepared and purified as to render it substantially free of natural contaminants. Such a preparation is then introduced into an animal in order to produce polyclonal antisera of greater specific activity.

In certain embodiments, the compounds of the present invention comprise, instead of, or in addition to an antibody, a receptor or ligand that has a matching or counterpart ligand or receptor expressed on a cell surface of a target cell. In these embodiments, the compound comprises one or more CD1d complexes and a ligand or receptor specific for a cell surface marker. Examples include: CD4 coupled to CD1d for interaction with HIV infected cells; chemokine or chemokine receptor coupled to CD1d for interaction with DC subset; or heregulins coupled to CD1d for interaction with ErbB2 positive tumor cells.

In one embodiment, the antibody is specific for a cell surface marker of a tumor cell. CD1d-NKT can be directly cytolytic to tumor cells and can also recruit either directly or through activation of DC both NK cells and cytolytic T cells. The present invention allows CD1d loaded with a stimulatory ligand such as α-GalCer to be targeted to tumors by coupling the complex to an antibody specific for a tumor cell surface antigen. The CD1d complex concentrated on tumor cells will then recruit and activate CD1d-NKT cells and trigger a cascade of events that promote tumor cell-killing and growth inhibition.

In a preferred embodiment of the use of the present invention said cancer is a head and neck cancer, gastric cancer, esophageal cancer, stomach cancer, colorectal cancer, coloncarcinoma, cancer of liver and intrahepatic bile ducts, pancreatic cancer, lung cancer, small cell lung cancer, cancer of the larynx, breast cancer, malignant melanoma, multiple myeloma, sarcomas, rhabdomyosarcoma, lymphomas, folicular non-Hodgkin-lymphoma, leukemias, T- and B-cell-leukemias, Hodgkin-lymphoma, B-cell lymphoma, ovarian cancer, cancer of the uterus, cervical cancer, prostate cancer, genital cancer, renal cancer, cancer of the testis, thyroid cancer, bladder cancer, plasmacytoma or brain cancer.

Tumor associated antigens comprise pan-carcinoma antigens like CEA (Sundblad Hum. Pathol. 27, (1996) 297-301, llantzis Lab. Invest. 76(1997), 703-16), EGFR type I (Nouri, Int. J. Mol. Med. 6 (2000), 495-500) and EpCAM (17-1A/KSA/GA733-2, Balzar J. Mol. Med. 77 (1999), 699-712). EGFR type I is especially overexpressed in glioma and EpCAM in colon carcinoma. EGFR type II (Her-2/neu, ERBB2 Sugano Int. J. Cancer 89 (2000), 329-36) and TAG-72 glycoprotein (sTN antigen, Kathan Arch. Pathol. Lab. Med. 124 (2000), 234-9) are upregulated in breast cancer. EGFR deletion neoepitope might also play a role as tumor associated antigen (Sampson Proc. Nati. Acad. Sci. USA 97 (2000), 7503-8). The antigens A33 (Ritter Biochem. Biophys. Res. Commun. 236 (1997), 682-6), Lewis-Y (Di-Carlo Oncol. Rep. 8 (2001), 387-92), Cora Antigen (CEA-related Cell Adhesion Molecule CEACAM 6, CD66c, NCA-90, Kinugasa lnt. J. Cancer 76 (1998), 148-53) and MUC-1 (Mucin) are associated with colon carcinoma (lida Oncol. Res. 10 (1998), 407-14). Thomsen-Friedenreich-antigen (TF, Gal1B-3GaINAca1-0-Tbr/Ser) is not only found in colon carcinoma (Baldus Cancer 82 (1998), 1019-27) but also in breast cancer (Glinsky Cancer. Res. 60 (2000), 2584-8). Overexpression of Ly-6 (Eshel J. Biol. Chem. 275 (2000), 12833-40) and desmoglein 4 in head and neck cancer and of E-cadherin neoepitope in gastric carcinoma has been described (Fukudome Int. J. Cancer 88 (2000), 579-83). Prostate-specific membrane antigen (PSMA, Lapidus Prostate 45 (2000), 350-4), prostate stem cell antigen (PSCA, Gu Oncogene 191 (2000) 288-96) and STEAP (Hubert, Proc Natl Acad Sci USA 96 (1999), 14523-8) are associated with prostate cancer. The alpha and gamma subunit of the fetal type acetylcholine receptor (AChR) are specific immunohistochemical markers for rhabdomyosarcoma (RMS, Gattenlohner Diagn. Mol. Pathol. 3 (1998), 129-34).

Association of CD20 with follicular non-Hodgkin lymphoma (Yatabe Blood 95 (2000), 2253-61, Vose Oncology (Huntingt) 2 (2001) 141-7), of CD19 with B-cell lymphoma (Kroft Am. J. Clin. Pathol. 115 (2001), 385-95), of Wue-1 plasma cell antigen with multiple myeloma (Greiner Virchows Arch 437 (2000), 372-9), of CD22 with B cell leukemia (dArena Am. J. Hematol. 64 (2000), 275-81), of CD7 with T-cell leukemia (Porwit-MacDonald Leukemia 14 (2000), 816-25) and CD25 with certain T and B cell leukemias has been described (Wu Arch. Pathol. Lab. Med. 124 (2000), 1710-3). CD30 is associated with Hodgkin-lymphoma (Mir Blood 96 (2000), 4307-12). Expression of melanoma chondroitin sulfate proteoglycan (MCSP, Eisenmann Nat. Cell. Biol. 8 (1999), 507-13) and gangiloside GD3 is observed in melanoma (Welte Exp Dermatol 2 (1997), 64-9), while GD3 is also found in small cell lung cancer (SCLC, Brezicka Lung Cancer 1 (2000), 29-36). Expression of gangiloside GD2 is, also upregulated in SCLC and in neuroblastoma (Cheresh et al. Cancer Res. 10 (1986), 5112-8). Ovarian carcinoma is associated with Muellerian Inhibitory Substance (S) receptor type II (Masiakos Clin. Cancer Res. 11 (1999), 3488-99) and renal as well as cervical carcinoma with expression of carboanhydrase 9 (MN/CAIX, Grabmaier Int. J. Cancer 85 (2000) 865-70). Elevated expression levels of CA 19-9 were found in pancreatic cancer (Nazli Hepatogastroenterology 47 (2000), 1750-2).

Other examples of tumor cell surface antigens are Her2/neu, expressed in breast and ovarian carcinomas (Zhang, H. et al., *Experimental & Molecular Pathology* 67:15-25 (1999)); CM-1, expressed in breast cancer (Chen, L. et al., *Acta Academiae Medicinae Sinicae* 19(2):150-3); 28K2, expressed in Lung adenocarcinoma and large cell carcinoma (Yoshinari, K et al., *Lung Cancer* 25:95-103 (1999)); E48 and U 36 expressed in head and neck squamous cell carcinoma (Van Dongen, G. A. M. S. et al., *Anticancer Res.* 16:2409-14 (1996)); NY-ESO-1, expressed in esophageal carcinoma, and melanoma Jager, E. et al., *J. Exp. Med.* 187:265-70 (1998); Jager, E. et al., *International J. Cancer* 84:506-10 (1999)); KU-BL 1-5, expressed in bladder carcinoma (Ito, K. et al., *AUA 2000 Annual Meeting*, Abstract 3291 (2000)); NY CO 1-48, expressed in colon carcinoma (Scanlan, M. J. et al., *International J. Cancer* 76:652-8 (1998)); HOM MEL 40, expressed in melanoma (Tureci, O. et al., *Cancer Res.* 56:4766-72 (1996)); OV569, expressed in ovarian carcinoma (Scholler, N. et al., *Proc. Natl. Acad, Sci. USA* 96:11531-6 (1999)); ChCE7, expressed in neuroblastoma and renal cell carcinoma (Meli, M. L. et al., *International J. Cancer* 83:401-8 (1999)); CA19-9, expressed in colon carcinoma (Han, J. S. et al., *Cancer* 76:195-200 (1995)); CA125, expressed in ovarian carcinoma (O'Brien, T. J. et al., *International J. Biological Markers* 13:188-95 (1998)); and Gangliosides (GM2, GD2, 9-o-acetyl-GD3, GD3), expressed in melanoma and neuroblastoma (Zhang, S. et al., *Cancer Immunol. Immunotherapy* 40:88-94 (1995)).

In a most preferred embodiment of the method of the present invention said tumor-associated antigen is selected from the group consisting of Lewis Y, CEA, Muc-1, erbB-2,-3 and -4, Ep-CAM, E-cadherin neoepitope, EGF-receptor (e.g. EGFR type I or EGFR type II), EGFR deletion neoepitope, CA19-9, Muc-1, LeY, TF-, Tn- and sTn-antigen, TAG-72, PSMA, STEAP, Cora antigen, CD7, CD19 and CD20, CD22, CD25, Ig-a and Ig-B, A33 and G250, CD30, MCSP and gp100, CD44-v6, MT-MMPS, (MIS) receptor type II, carboanhydrase 9, F19-antigen, Ly6, desmoglein 4, PSCA, Wue-1, GD2 and GD3 as well as TM4SF-antigens (CD63, L6, CO-29, SAS), the alpha and gamma subunit of the fetal type acetylcholinreceptor (AChR), CM-1, 28K2, E48, U36, NY-ESO-1, KU-BL 1-5, NY CO 1-48, HOM MEL 40, OV569, ChCE7, CA19-9, CA125, GM2, GD2, 9-o-acetyl-GD3, or GD3.

In another embodiment, the antibody is specific for a cell surface marker of a CD1d-restricted NKT cells. In this embodiment, an inhibitory signal can be delivered to the NKT cells through their CD1d-restricted TCR, which can result in systemic downregulation of CD1d-NKT cell activity. Even in the absence of a linked inhibitory signal, just direct binding of CD1d:α-GalCer complexes to NKT cells has been reported to induce apoptosis of the NKT (Matsuda, J. L. et al. J. Exp. Med. 192:741-754,2000). Suitable NKT cell markers to which to target specific antibodies are CD161, CD56, or (for NKT subsets) CCR4 on CD4+

CD1d-NKT or CCR1 or CCR6 on double negative CD1d-NKT. This is particularly useful in treating diseases or symptoms which are the result of high NKT activity. These include myasthenia gravis (Reinhardt et al. Neurology 52:1485-87,1999), psoriasis (Bonish, J. Immunol. 165: 4076-85,2000), ulcerative colitis (Saubermann et al. Gastroenterology 119:119-128, 2000), and primary biliary cirrhosis (Kita et al. Gastroenterology 123:1031-43,2002). In these embodiments, localized downregulation of CD1d-NKT may ameliorate disease.

In another embodiment, the antibody is specific for a cell surface marker of a target tissue of autoimmune disease or inflammatory response. CD1d-NKT stimulated to secrete IL-4 by normal antigen presenting cells and DC at the site of an autoimmune lesion or inflammatory site can regulate the development and expression of aggressive cell-mediated immune responses. For those autoimmune or inflammatory diseases whose etiology is related to a paucity of CD1d-NKT in a specific tissue, this defect can be ameliorated by allowing CD1d loaded with a stimulatory ligand such as α-GalCer to be targeted to that tissue. In a preferred embodiment, CD1d:α-GalCer is targeted to such sites by coupling the complex to an antibody specific for a local tissue antigen. The CD1d complex concentrated on local tissue cells will then lead to recruitment and activation of CD1d-NKT cells and trigger a cascade of events that regulate the autoimmune or inflammatory response. The relevant specific tissue antigens may be different for different autoimmune and inflammatory diseases.

Alternatively, in this embodiment, the CD1d complexes comprise an antigen (for example, a lipid, glycolipid, or hydrophobin peptide) with antagonist properties (Miyamoto Nature 413:531-534, 2001). This embodiment of the invention is of particular relevance to those autoimmune diseases that appear to result from excessive CD1d-NKT activity. These include myasthenia gravis (Reinhardt et al. Neurology 52:1485-87,1999), psoriasis (Bonish, J. Immunol. 165: 4076-85,2000), ulcerative colitis (Saubermann et al. Gastroenterology 119:119-128, 2000), and primary biliary cirrhosis (Kita et al. Gastroenterology 123:1031-43,2002). In these embodiments, localized downregulation of CD1d-NKT may ameliorate disease.

In the case of demyelinating diseases including, most especially, multiple sclerosis, the antibody is specific for MBP (myelin basic protein), PLP (myelin proteolipid protein), or MOG (myelin oligodendrocyte glycoprotein). In a most preferred embodiment, the antibody is specific for MOG.

In the case of juvenile onset type I diabetes which follows from destruction of insulin producing pancreatic islet beta cells, the antibody is specific for target antigens of the islet beta cells such as GT3 ganglioside, IGRP (islet-specific glucose-6-phosphatase), or SUR1 (Proks P et al., Diabetes: 51 Suppl 3:S368-76, 2002). Recently, peri-islet Schwann cells have been described as an early target of autoimmune destruction in this disease (Winer S et al: Nature Medicine 9:198-205, 2003). In another preferred embodiment of the invention, therefore, the antibody is specific for Schwann cell specific antigens glial fibrillary acidic protein (GFAP), and S100beta for treatment or diagnosis of juvenile onset type I diabetes.

In other preferred embodiments of the invention for treatment of autoimmune and inflammatory diseases, conjugates comprising CD1d complexes and antibodies specific for type II collagen are injected into affected joints for treatment of rheumatoid arthritis; antibodies specific for thyroglobulin or TSH receptor are targeted to the thyroid for treatment of Hashimoto's thyroiditis and Graves' disease; and antibodies specific for the K+/H+ ATPase are employed for treatment of pernicious anemia or atrophic gastritis (targeting the gastric parietal cells).

In other preferred embodiments, the invention is employed to treat other autoimmune conditions: ankylosing spondylitis, acute anterior uveitis, Goodpasture's syndrome, Myasthenia gravis, Systemic Lupus Erythematosus, systemic sclerosis, *Pemphigus vulgaris*, or autoimmune Hepatitis. As discussed below, in some manifestations of autoimmune or inflammatory disease there is a surfeit rather than a paucity of CD1d-NKT cells or an excess of one subset of CD1d-NKT relative to another e.g. CD4+ CD1d-NKT relative to double negative (CD4−/CD8−) CD1d-NKT. Conjugates of the invention described here that can result in inhibition rather than activation of CD1d-NKT or that, by targeting different DC subsets, can activate one CD1d-NKT cell subset in preference to another.

In other embodiments, the antibody is specific for a cell surface marker of an infected cell or tissue. CD1d-NKT have been shown to have an important role in resistance to malaria, fungal and hepatitis B virus infections [12-14]. In a preferred embodiment, CD1d loaded with a stimulatory ligand such as α-GalCer is targeted to the site of infection by coupling the complex to an antibody specific for an antigen encoded by the infectious agent. The CD1d complex concentrated on infected cells will then lead to recruitment and activation of CD1d-NKT cells and trigger a cascade of events that lead to elimination or inhibition of growth of the infectious agent. The relevant antigens are different in the case of different infectious agents. In a preferred embodiment of the method of the present invention said surface marker for an infected cell is selected from the group consisting of viral envelope antigens, e.g. of human retroviruses (HTLV I and II, HIV1 and 2) or human herpes viruses (HSV1 and 2, CMV, EBV), haemagglutinin e.g. of influenza virus (influenza A, B or C), glycoproteins E1 and E2 from rubella virus or RGP of rabies virus.

In other preferred embodiments, the antibody is targeted to antigens encoded by other infectious viruses, bacteria, fungi, protozoa or helminthes.

In other embodiments, the antibody is specific for a cell surface marker of a target of allogenicity. CD1d-NKT have been reported to play a major role in blocking graft vs. host disease following allogeneic bone marrow transplantation (Zeng D. et al. J. Exp. Med. 189:1073-81,1999) and in maintenance of tolerance to allograft transplants (Seino K I et al. Proc. Natl. Acad. Sci. USA 98:2577-81,2001). An interesting feature of CD1d-NKT mediated allograft tolerance is that it is reported to depend on production of IFN-γ but not IL-4 by CD1d-NKT.

In a preferred embodiment of the invention, CD1d loaded with a stimulatory ligand such as α-GalCer is targeted to an allograft by coupling the complex to an antibody specific for a major or minor histocompatibility antigen of the allogeneic bone marrow or organ graft. The CD1d complex concentrated on cells of the allograft will then lead to recruitment and activation of CD1d-NKT cells. Examples of histocompatibility antigens include HLA specificities such as A (e.g. A1-A74), B (e.g., B1-B77), C (e.g., C1-C11), D (e.g., D1-D26), DR (e.g., DR1-DR8), DQ (e.g., DQ1-DQ9) and DP (e.g. DP1-DP6). More preferably, HLA specificities include A1, A2, A3, A11, A23, A24, A28, A30, A33, B7, B8, B35, B44, B53, B60, B62, DR1, DR2, DR3, DR4, DR7, DR8, and DR11. It is possible to tissue type a person by serological or genetic analysis to define which MHC class I or II molecule variants each person has using methods known in the art.

In one embodiment, the antibody is specific for a cell surface marker of a professional antigen presenting cell. Preferably, the antibody is specific for a cell surface marker of a dendritic cell, for example, CD83, DEC205, CMRF-44 (Fearnley D B et al. Blood 89:3708-16,1997), CMRF-56 (Hock B D et al. Tissue Antigens 53:320-34,1999), BDCA-1, BDCA-2, BDCA-3, and BDCA-4 (Dzionek A et al. *J. Immunol.* 165:6037-6046,2000). In other embodiments, the antibody is specific for markers of antigen presenting cells including Toll-like receptors (TLR1, TLR2, TLR3, TLR4, TLR5, TLR7, TLR9) mannose receptor, and mannan-binding lectin (MBL). As well as additional markers specific to dendritic cells, including, DC-SIGN (the C-type lectin, non-integrin, ICAM-3 receptor on DC), ALCAM, DC-LAMP, and any of a number of other receptors for apoptotic cells including phosphatidylserine receptor. The antibody may be specific for a cell surface marker of another professional antigen presenting cell such as a B cell or a macrophage. CD19, CD20 and CD22 are expressed on B cells, and other markers have been described for other antigen presenting cells.

In other embodiments, the antibody is specific for a cell surface marker of a dendritic cell subset. As noted above, whether CD1d-NKT give rise to a predominantly pro-inflammatory or anti-inflammatory response is, in part, a function of the relative frequency of two CD1d-NKT subsets. CD1d-NKT that are negative for expression of both CD4 and CD8 (double negative) and express the chemokine receptors CCR1 and CCR6 give rise to predominantly a pro-inflammatory TH1 type response including secretion of IFN-γ and TNF-α. In contrst, CD1d-NKT that are CD4+ and express the chemokine receptor CCR4 give rise to both a TH1 type and TH2 type response including secretion of the anti-inflammatory Th2-type cytokines IL-4, IL-5, IL-10 and IL-13. The activation of different CD1d-NKT subsets and their radiating influence in promulgating pro-inflammatory or anti-inflammatory responses is mediated by their interaction with different DC subsets (Wilson S B and Delovitch T L Nature Rev. Immunol. 3:211-222,2003; Vincent M S et al. Nature Immunol. 3:1163-68,2002).

Human DC have been broadly distinguished as myeloid and plasmacytoid. Myeloid DC are characterized by a monocytic morphology, express myeloid markers including the β2 integrin CD11c, and produce high levels of IL-12. Plasmacytoid DC, in contrast, have a morphology that is plama cell like, are CD11c negative, and produce high levels of IFN-α. Based on their ability to induce, under appropriate conditions, predominantly TH1 or TH2 type responses, mature myeloid DC have been designated as DC1 and mature plasmacytoid DC as DC2 (Rissoan M C et al. Science 283:1183, 1999). There is, however, a considerable degree of plasticity in the function of DC subsets that is influenced by the antigen they present, particularly antigens of microbial origin that match pattern recognition receptors on DC, by the cytokine environment in which they differentiate from earlier precursors, and by the properties of the T cells with which they interact (Liu Y J et al. Nature Immunol. 2:585-589,2001; Pulendran B et al. Science 293: 253-256,2001; Banchereau J et al. Ann. Rev. Immunol. 18:767-811,2000). Cross-talk between T cells and DC has emerged as an important factor in the maturation, polarization and survival of both T cells and DC (Shreedhar V et al. Immunity 11:625-636,1999) including interactions between CD1d expressing DC and CD1d-restricted NKT (Wilson S B and Delovitch T L Nature Rev. Immunol. 3:211-222,2003; Vincent M S et al. Nature Immunol. 3:1163-68,2002).

In a preferred embodiment of the invention, CD1d loaded with a stimulatory ligand such as α-GalCer is targeted to DC by coupling the complex to an antibody specific for a surface antigen marker of DC such as CD83, DEC205, CMRF-44, CMRF-56, DC-SIGN, Toll-like Receptors (TLR) including TLR1, TLR2, TLR3, TLR4, TLR5, TLR7, TLR9, mannose receptor, mannan-binding lectin (MBL), ALCAM, DC-LAMP, phosphatidylserine receptor, BDCA-1, BDCA-2, BDCA-3 or BDCA-4 (neuropilin, Tordjman R et al. Nature Immunol. 3:477-82,2002). The CD1d complex concentrated on DC will then lead to recruitment and activation of CD1d-NKT cells.

In a most preferred embodiment of the invention, CD1d loaded with a stimulatory ligand such as α-GalCer is targeted to a particular DC subset by coupling the complex to an antibody specific for a surface antigen marker of said DC subset such as TLR2, TLR4, TLR7, TLR9, BDCA-1, BDCA-2, BDCA-3, and BDCA-4 (Dzionek A et al. J. Immunol. 165:603746,2000; Liu Y J et al. Nature Immunol. 2:585-589,2001; Penna G et al. J. Immunol. 167:1862-66, 2001) or mannose receptor. TLR2, TLR4, BDCA-1 (CD1c), BDCA-3, and mannose receptor are expressed on subsets of myeloid DC while TLR7, TLR9, BDCA-2 and BDCA-4 are expressed on plasmacytoid DC. The CD1d complex concentrated on the DC subset will then lead to recruitment and activation of a matched subset of CD1d-NKT cells. This embodiment of the invention offers a focused means of directing polarization of immune responses to aggressive cell-mediated immunity or to potential tolerogenic interactions. The former is appropriate for inducing immunity to tumors and the latter for downregulation of autoimmune responses that are associated, for example, with multiple sclerosis or type I diabetes.

The strategy of targeting CD1d complexes to DC subsets can be employed either alone or in combination with targeting CD1d complexes to specific tissues or organs.

The compounds of the present invention may be labeled, so as to be directly detectable, or will be used in conjunction with secondary labeled immunoreagents which will specifically bind the compound for example, for detection or diagnostic purposes. Labels of interest may include dyes, enzymes, chemiluminescers, particles, radioisotopes, or other directly or indirectly detectable agent. Alternatively, a second stage label may be used, e.g. labeled antibody directed to one of the constituents of the compound of the invention.

Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include 3H, 111In, 125I, 131I, 32P, 35S, 14C, 51Cr, 57To, 58Co, 59Fe, 75Se, 152Eu, 90Y, 67Cu, 217Ci, 211At, 212Pb, 47Sc, 109Pd, etc. 111In is a preferred isotope where in vivo imaging is used since its avoids the problem of dehalogenation of the 125I or 131I-labeled monoclonal antibody by the liver. In addition, this radio nucleotide has a more favorable gamma emission energy for imaging (Perkins et al., Eur. J. Nucl. Med. 10:296-301 (1985); Carasquillo et al., J. Nucl. Med. 28:281-287 (1987)). For example, 111In coupled to monoclonal antibodies with 1-(P-isothiocyanatobenzyl)-DPTA has shown little uptake in non-tumorous tissues, particularly the liver, and therefore enhances specificity of tumor localization (Esteban et al., J. Nucl. Med. 28:861-870 (1987)).

Examples of suitable non-radioactive isotopic labels include 157Gd, 55Mn, 162Dy, 52Tr, and 56Fe.

Examples of suitable fluorescent labels include an 152Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and Fe.

Typical techniques for binding the above-described labels to antibodies are provided by Kennedy et al., Clin. Chim. Acta 70:1-31 (1976), and Schurs et al., Clin. Chim. Acta 81:140 (1977). Coupling techniques mentioned in the latter are the glutaraldehyde method, the periodate method, the dimaleimide method, the m-maleimidobenzyl-N-hydroxysuccinimide ester method, all of which methods are incorporated by reference herein.

The compound of the invention may further comprise other therapeutic agents. The therapeutic agent or agents may be linked to the multivalent compound, the antibody, or the CD1d complex. Examples of therapeutic agents include, but are not limited to, antimetabolites, alkylating agents, anthracyclines, antibiotics, and anti-mitotic agents. Antimetabolites include methotrexate, 6-mercaptopurine, 6-thioguanine, cytarabine, 5-fluorouracil decarbazine. Alkylating agents include mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin. Anthracyclines include daunorubicin (formerly daunomycin) and doxorubicin (also referred to herein as adriamycin). Additional examples include mitozantrone and bisantrene. Antibiotics include dactinomycin (formerly actinomycin), bleomycin, mithramycin, and anthramycin (AMC). Antinytotic agents include vincristine and vinblastine (which are commonly referred to as vinca alkaloids). Other cytotoxic agents include procarbazine, hydroxyurea, asparaginase, corticosteroids, mytotane (O,P'-(DDD)), interferons. Further examples of cytotoxic agents include, but are not limited to, ricin, doxorubicin, taxol cytochalasin B, gramicidin D, ethidium bromide, etoposide, tenoposide, colchicin, dihydroxy anthracin dione, 1-dehydrotestosterone, and glucocorticoid.

Analogs and homologs of such therapeutic and cytotoxic agents are encompassed by the present invention. For example, the chemotherapuetic agent aminopterin has a correlative improved analog namely methotrexate.

Further, the improved analog of doxorubicin is an Fe-chelate. Also, the improved analog for 1-methylnitrosourea is lomustine. Further, the improved analog of vinblastine is vincristine. Also, the improved analog of mechlorethamine is cyclophosphamide.

The present invention also relates to vectors which include a nucleotide sequence encoding a compound of the present invention or parts thereof, host cells which are genetically engineered with the recombinant vectors, and the production of the compounds of the present invention or parts thereof by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the E. coli lac, trp and tac promoters, or, in mammalian cells, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS and Bowes melanoma cells; and plant cells. Appropriate culture mediums and conditions for the above-described host cells are known in the art.

Several eukaryotic expression systems have been used for production of soluble CD1d complex, such as SC2 Drosophila melanogaster cells (Benlagha et al., 2000. J Exp Med 191:1895), baculovirus system (61) and Chinese hamster ovary CHO cells (Gumperz et al., 2002. J Exp Med 195:625). Regarding fusion proteins, a single chain composed of β2 microglobulin fused to N-terminus of CD1d heavy chain fused to the Fc part of IgG2a has been successfully produced in CHO cells both for human and mouse CD1d (Gumperz et al., 2002. J Exp Med 195:625, Gumperz et al., 2000. Immunity 12:211). The Fc portion of IgG2a can be replaced with the variable portion of the desired anti-TAA mAb, possibly a single chain scFv antibody fragment.

In parallel, a chemically coupled CD1d-antibody Fab fragment can be obtained essentially as done for MHC Class I-antibody conjugates (14) except that the CD1d-β2 microglobulin complex is produced in a eukaryotic system. Briefly, a free cysteine will be engineered at the carboxyl terminus of the CD1d molecule and after expression and purification, the CD1d complex is chemically coupled to the free cysteines of the Fab fragment via a thiol reactive bis-maleimide linker. For both the fusion and the conjugate strategy, α-GalCer can be loaded on CD1d either at the time of cell-based synthesis or after production and purification of the soluble CD1d complex.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when the Fc portion proves to be a hindrance to use in therapy and diagnosis, for example when the fusion protein is to be used as an antigen for immunizations. In drug discovery, for example, human proteins, such as the hIL5-receptor, have been fused with Fc portions for the purpose of high-throughput screening assays to identify antagonists of hIL-5. See, D. Bennett et al., J. Mol. Recognition 8:52-58 (1995) and K. Johanson et al., J. of Biol. Chem. 270(16): 9459-9471 (1995).

Several reports have described secretion and assembly of fusion proteins comprised of diverse sequences linked to the carboxyl terminus of immunoglobulin chains (Harvill, E. T. et al., J. Immunol. 157:3165-70 (1996); Shin, S. U. et al., J. Immunology 158: 4797-4804 (1997); Penichet, M. L. et al., J. Immunol. 163:4421-26 (1999); Zhang, H. F. et al., J. Clin. Invest 103:55-61 (1999)). Fusion proteins of the compounds of this invention will likewise retain amino terminal sequences of the immunoglobulin chain that direct secretion. CD1d molecules linked to the carboxyl terminus of the immunoglobulin chains are stripped of hydrophobic transmembrane sequences and should not interfere with secretion.

The polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides useful in the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

The ability of a compound of the present invention to modulate an immune response can be readily determined by an in vitro assay. NKT cells for use in the assays include transformed NKT cell lines, or NKT cells which are isolated from a mammal, e.g., from a human or from a rodent such as a mouse. NKT cells can be isolated from a mammal by sorting cells that bind CD1d:α-GalCer tetramers. See, for example, Benlagha et al., J Exp Med 191 (2000), pp. 1895-1903; Matsuda et al., J Exp Med 192 (2000), pp. 741-754; and Karadimitris et al., Proc Natl Acad Sci USA 98 (2001), pp. 3294-3298. A suitable assay to determine if a compound of the present invention is capable of modulating the activity of NKT cells is conducted by coculturing NKT cells and antigen presenting cells, adding the particular compound of interest to the culture medium that targets either the antigen presenting cells or the NKT cells directly, and measuring IL-4 or IFN-γ production. A significant increase or decrease in IL-4 or IFN-γ production over the same co-culture of cells in the absence of the compound of the invention or, preferably, in the presence of a compound of the invention with a non-targeting antibody indicates stimulation or inhibition of NKT cells.

The NKT cells employed in the assays are incubated under conditions suitable for proliferation. For example, an NKT cell hybridoma is suitably incubated at about 37° C. and 5% CO2 in complete culture medium (RPMI 1640 supplemented with 10% FBS, penicilin/streptomycin, L-glutamine and 5×10-5 M 2-mercaptoethanol). Serial dilutions of the compound can be added to the NKT cell culture medium. Suitable concentrations of the compound added to the NKT cells typically will be in the range of from $10^{-12}$ to $10^{-6}$ M. Use of antigen dose and APC numbers giving slightly submaximal NKT cell activation is preferred to detect stimulation or inhibition of NKT cell responses by the compounds of the invention.

Alternatively, rather than measurement of an expressed protein such as IL-4 or IFN-γ, modulation of NKT cell activation can be determined by changes in antigen-dependent T cell proliferation as measured by radiolabelling techniques as are recognized in the art. For example, a labeled (e.g., tritiated) nucleotide may be introduced to an assay culture medium. Incorporation of such a tagged nucleotide into DNA serves as a measure of T cell proliferation. This assay is not suitable for NKT cells that do not require antigen presentation for growth, e.g., NKT cell hybridomas. A difference in the level of T cell proliferation following contact with the compound of the invention indicates the complex modulates activity of the T cells. For example, a decrease in NKT cell proliferation indicates the compound can suppress an immune response. An increase in NKT cell proliferation indicates the compound can stimulate an immune response.

Additionally, the $^{51}$Cr release assay, described below, can be used to determine cytotoxic activity.

These in vitro assays can be employed to select and identify CD1d complexes that are capable of modulating an immune response. Assays described above, e.g., measurement of IL-4 or IFN-γ production or NKT cell proliferation, are employed to determine if contact with the compound modulates T cell activation.

In vivo assays also may be suitably employed to determine the ability of a compound of the invention to modulate the activity of NKT cells. For example, a compound of interest can be assayed for its ability to stimulate NKT cell activation or inhibit tumor growth. For example, a compound of the invention can be administered to a mammal such as a mouse, before or after challenge with a tumorigenic dose of transformed cells and the presence or size of growing tumors may be monitored.

The present invention also includes pharmaceutical compositions comprising a compound described above in combination with a suitable pharmaceutical carrier. Such compositions comprise a therapeutically effective amount of the compound and a pharmaceutically acceptable carrier or excipient. Such a carrier includes but is not limited to saline, buffered saline, dextrose, water, glycerol, ethanol, and combinations thereof. The formulation should suit the mode of administration.

The present invention also includes a method of modulating, i.e., either stimulating or inhibiting an immune response, comprising administering to an animal an effective amount of a compound or composition of the invention.

The compounds of the present invention may be administered in pharmaceutical compositions in combination with one or more pharmaceutically acceptable excipients. It will be understood that, when administered to a human patient, the total daily usage of the pharmaceutical compositions of the present invention will be decided by the attending physician within the scope of sound medical judgment. The specific therapeutically effective dose level for any particular patient will depend upon a variety of factors including the type and degree of the response to be achieved; the specific composition of another agent, if any, employed; the age, body weight, general health, sex and diet of the patient; the time of administration, route of administration, and rate of excretion of the composition; the duration of the treatment; drugs (such as a chemotherapeutic agent) used in combination or coincidental with the specific composition; and like factors well known in the medical arts. Suitable formulations, known in the art, can be found in Remington's Pharmaceutical Sciences (latest edition), Mack Publishing Company, Easton, Pa.

The compound to be used in the therapy will be formulated and dosed in a fashion consistent with good medical practice, taking into account the clinical condition of the individual patient (especially the side effects of treatment with the compounds alone), the site of delivery of the compound, the method of administration, the scheduling of administration, and other factors known to practitioners. The "effective amount" of the compounds of the invention for purposes herein is thus determined by such considerations.

Pharmaceutical compositions of the invention may be administered orally, intravenously, rectally, parenterally, intracisternally, intradermally, intravaginally, intraperitoneally, topically (as by powders, ointments, gels, creams, drops or transdermal patch), bucally, or as an oral or nasal spray. The term "parenteral" as used herein refers to modes of administration which include intravenous, intramuscular, intraperitoneal, intrastemal, subcutaneous and intraarticular injection and infusion.

The pharmaceutical compositions are administered in an amount which is effective for treating and/or prophylaxis of the specific indication. In most cases, the dosage is from about 1 μg/kg to about 30 mg/kg body weight daily, taking into account the routes of administration, symptoms, etc. However, the dosage can be as low as 0.001 μg/kg.

As a general proposition, the total pharmaceutically effective amount of the compositions administered parenterally per dose will be in the range of about 1 μg/kg/day to 100 mg/kg/day of patient body weight, although, as noted above, this will be subject to therapeutic discretion. If given continuously, the composition is typically administered at a dose rate of about 1 μg/kg/hour to about 5 mg/kg/hour, either by 1-4 injections per day or by continuous subcutaneous infusions, for example, using a mini-pump. An intravenous bag solution or bottle solution may also be employed.

The compounds of the invention may also be suitably administered by sustained-release systems. Suitable examples of sustained-release compositions include semipermeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (U. Sidman et al., Biopolymers 22:547-556 (1983)), poly (2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(-)-3-hydroxybutyric acid (EP 133,988). Sustained-release compositions also include liposomally entrapped compositions of the present invention. Liposomes are prepared by methods known per se: DE 3,218,121; Epstein, et al., Proc. Natl. Acad. Sci. USA 82:3688-3692 (1985); Hwang et al., Proc. Natl. Acad. Sci. USA 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal therapy.

For parenteral administration, in one embodiment, the composition is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compositions that are known to be deleterious to polypeptides.

Generally, the formulations are prepared by contacting the compounds of the invention uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes. Suitable formulations, known in the art, can be found in Remington's Pharmaceutical Sciences (latest edition), Mack Publishing Company, Easton, Pa.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The compositions are typically formulated in such vehicles at a concentration of about 0.01 µg/ml to 100 mg/ml, preferably 0.01 µg/ml to 10 mg/ml, at a pH of about 3 to 8. It will be understood that the use of certain of the foregoing excipients, carriers, or stabilizers will result in the formation of salts.

Compositions to be used for therapeutic administration must be sterile. Sterility is readily accomplished by filtration through sterile filtration membranes (e.g., 0.2 micron membranes). Therapeutic compositions generally are placed into a container having a sterile access port, for example, an intravenous solution bag or vial having a stopper pierceable by a hypodermic injection needle.

The compounds of the invention ordinarily will be stored in unit or multi-dose containers, for example, sealed ampules or vials, as an aqueous solution or as a lyophilized formulation for reconstitution. As an example of a lyophilized formulation, 10-ml vials are filled with 5 ml of sterile-filtered 1% (w/v) aqueous solution, and the resulting mixture is lyophilized. The infusion solution is prepared by reconstituting the lyophilized composition using bacteriostatic Water-for-Injection.

Dosaging may also be arranged in a patient specific manner to provide a predetermined concentration of activity in the blood, as determined by an RIA technique, for instance. Thus patient dosaging may be adjusted to achieve regular on-going trough blood levels, as measured by RIA, on the order of from 50 to 1000 ng/ml, preferably 150 to 500 ng/ml.

The compounds of the invention are useful for administration to any animal, preferably a mammal (such as apes, cows, horses, pigs, boars, sheep, rodents, goats, dogs, cats, chickens, monkeys, rabbits, ferrets, whales, and dolphins), and more preferably a human.

The invention also provides a pharmaceutical pack or kit comprising one or more containers filled with one or more of the ingredients of the pharmaceutical compositions of the invention. Associated with such containers can be a notice in the form prescribed by a governmental agency regulating the manufacture, use or sale of pharmaceuticals or biological products, which notice reflects approval by the agency of manufacture, use or sale for human administration. In addition, the compositions of the present invention may be employed in conjunction with other therapeutic compositions.

Other therapeutic compositions useful for administration along with a compound of the present invention include cytotoxic drugs, particularly those which are used for cancer therapy. Such drugs include, in general, alkylating agents, anti-proliferative agents, tubulin binding agents and the like. Preferred classes of cytotoxic agents include, for example, the anthracycline family of drugs, the vinca drugs, the mitomycins, the bleomycins, the cytotoxic nucleosides, the pteridine family of drugs, diynenes, and the podophyllotoxins. Particularly useful members of those classes include, for example, adriamycin, carminomycin, daunorubicin, aminopterin, methotrexate, methopterin, dichloromethotrexate, mitomycin C, porfiromycin, 5-fluorouracil, 6-mercaptopurine, cytosine arabinoside, podophyllotoxin, or podophyllotoxin derivatives such as etoposide or etoposide phosphate, melphalan, vinblastine, vincristine, leurosidine, vindesine, leurosine and the like. As noted previously, one skilled in the art may make chemical modifications to the desired compound in order to make reactions of that compound more convenient for purposes of preparing conjugates of the invention.

The compounds of the invention can be used to treat tumor-bearing animals, including humans, to generate an immune response against tumor cells. The generation of an adequate and appropriate immune response leads to tumor regression in vivo. Such "vaccines" can be used either alone or in combination with other therapeutic regimens, including but not limited to chemotherapy, radiation therapy, surgery, bone marrow transplantation, etc. for the treatment of tumors. For example, surgical or radiation techniques could be used to debulk the tumor mass, after which, the vaccine formulations of the invention can be administered to ensure the regression and prevent the progression of remaining tumor masses or micrometastases in the body. Alternatively, administration of the "vaccine" can precede such surgical, radiation or chemotherapeutic treatment.

Alternatively, the compounds of the invention can be used to immunize or "vaccinate" tumor-free subjects to prevent tumor formation. With the advent of genetic testing, it is now possible to predict a subject's predisposition for certain cancers. Such subjects, therefore, may be immunized using a compound comprising one or more antigenic ligands derived from tumors.

Suitable preparations of such vaccines include injectables, either as liquid solutions or suspensions; solid forms suitable for solution in, or suspension in liquid prior to injection, may also be prepared. The preparation may also be emulsified, or the polypeptides encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine preparation may also include minor amounts of auxiliary substances such as wetting or emulsifying agents, pH buffering agents, and/or adjuvants which enhance the effectiveness of the vaccine.

Examples of adjuvants which may be effective, include, but are not limited to: aluminum hydroxide, N-acetyl-muramyl-L-threonyl-D-isoglutamine (thr-MDP), N-acetyl-normuramyl-L-alanyl-D-isoglutamine, N-acetylmuramyl-L-alanyl-D-isoglutaminyl-L-alanine-2-(1'-2'-dipalmitoyl-sn-glycero-3-hydroxyphosphoryloxy)-ethylamine, GM-CSF, QS-21 (investigational drug, Progenics Pharmaceuticals, Inc.), DETOX (investigational drug, Ribi Pharmaceuticals), BCG, and CpG rich oligonucleotides.

The composition, if desired, can also contain minor amounts of wetting or emulsifying agents, or pH buffering agents. The composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

In an alternate embodiment, compounds of the present invention may be used in adoptive immunotherapeutic methods for the activation of NKT lymphocytes that are histocompatible with the patient. (for methods of adoptive immunotherapy, see, e.g., Rosenberg, U.S. Pat. No. 4,690,915, issued Sep. 1, 1987; Zarling, et al., U.S. Pat. No. 5,081,029, issued Jan. 14, 1992). Such NKT lymphocytes may be isolated from the patient or a histocompatible donor. The NKT lymphocytes are activated in vitro by exposure to the compound of the invention. Activated NKT lymphocytes are expanded and inoculated into the patient in order to transfer NKT cell immunity directed against the particular antigenic peptide or peptides.

The compounds of the present invention may be administered along with other compounds which modulate an immune response, for example, cytokines. The term "cytokine" refers to polypeptides, including, but not limited to, interleukins (e.g., IL1, IL-2, IL-3, IL-4, IL-5, IL-6, IL-7, IL-8, IL-9, IL-10, IL-11, IL-12, IL-13, IL-14, IL-15, IL-16, IL-17, and IL-18), $\alpha$ interferons (e.g., IFN-$\alpha$), $\beta$ interferon (IFN-$\beta$), $\gamma$ interferons (e.g., IFN-$\gamma$), colony stimulating factors (CSFs, e.g., CSF-1, CSF-2, and CSF-3), granulocyte-macrophage colony stimulating factor (GMCSF), transforming growth factor (TGF, e.g., TGF$\alpha$ and TGF$\beta$), and insulin-like growth factors (IGFs, e.g., IGF-I and IGF-II).

The compounds of the invention may also be employed in accordance with the present invention by expression of such compounds, especially CD1d-antibody fusion compounds, in vivo, which is often referred to as "gene therapy."

Polynucleotide that encodes a compound of this invention that is a direct fusion of antibody and a CD1d molecule, as well as a polynucleotide encoding a $\beta$2-microglobulin fusion, may be introduced directly into cells by transfection or infection with a suitable vector so as to give rise to synthesis and secretion of that compound by the successfully transfected or infected cells. This can be accomplished by cotransfection with separate DNA vector constructs or by co-expression in the same vector.

Thus, for example, cells from a patient may be engineered with a polynucleotide (DNA or RNA) encoding a compound of the invention ex vivo, with the engineered cells then being provided to a patient to be treated with the compounds. Such methods are well-known in the art. For example, cells may be engineered by procedures known in the art by use of a retroviral particle containing RNA encoding a compound of the present invention.

Similarly, cells may be engineered in vivo for expression of a compound in vivo by, for example, procedures known in the art. As known in the art, a producer cell for producing a retroviral particle containing RNA encoding the compound of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle. Examples of other delivery vehicles include an HSV-based vector system, adeno-associated virus vectors, pox viruses, and inert vehicles, for example, dextran coated ferrite particles.

Retroviruses from which the retroviral plasmid vectors hereinabove mentioned may be derived include, but are not limited to, lentiviruses, Moloney Murine Leukemia virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The nucleic acid sequence encoding the compound of the present invention is under the control of a suitable promoter. Suitable promoters which may be employed include, but are not limited to, adenoviral promoters, such as the adenoviral major late promoter; or heterologous promoters, such as cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the $\beta$-actin promoter; and human growth hormone promoters.

The retroviral plasmid vector is employed to transduce packaging cell lines to form producer cell lines. Examples of packaging cell lines which may be transfected include, but are not limited to, the PE501, PA317, 2-2, 2-AM, PA12, T19-14x, VT-19-17-H2, 2CRE, 2CRIP, GP+E-86, GP+en-vAm12, and DAN cell lines as described in Miller, Human Gene Therapy 1:5-14 (1990), which is incorporated herein by reference in its entirety. The vector may transduce the packaging cells through any means known in the art. Such means include, but are not limited to, electroporation, the use of liposomes, and CaPO4 precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

In certain embodiments, the polynucleotide constructs may be delivered as naked polynucleotides. By "naked" polynucleotides is meant that the polynucleotides are free from any delivery vehicle that acts to assist, promote, or facilitate entry into the cell, including viral sequences, viral particles, liposome formulation, lipofectin, precipitating agents and the like. Such methods are well known in the art and described, for example, in U.S. Pat. Nos. 5,593,972, 5,589,466, and 5,580,859.

The naked polynucleotides used in the invention can be those which do not integrate into the genome of the host cell. These may be non-replicating sequences, or specific replicating sequences genetically engineered to lack the genome-integration ability. Alternatively, the naked polynucleotides used in the invention may integrate into the genome of the host cell by, for example, homologous recombination, as discussed below. Preferably, the naked polynucleotide construct is contained in a plasmid. Suitable expression vectors for delivery include, but are not limited to, vectors such as pRSVcat (ATCC 37152), pSVL and MSG (Pharmacia, Uppsala, Sweden), pSV2dhfr (ATCC 37146) and pBC12MI (ATCC 67109). Additional suitable plasmids are discussed in more detail above.

The naked polynucleotides can be administered to any tissue (such as muscle tissue) or organ, as described above. In another embodiment, the naked polynucleotides are administered to the tissue surrounding the tissue of origin. In another embodiment, the naked polynucleotides are administered systemically, through intravenous injection.

For naked polynucleotide injection, an effective dosage amount of polynucleotide will be in the range of from about 0.05 μg/kg body weight to about 50 mg/kg body weight. Preferably, the dosage will be from about 0.005 mg/kg to about 20 mg/kg and more preferably from about 0.05 mg/kg to about 5 mg/kg. The appropriate and effective dosage of the polynucleotide construct can readily be determined by those of ordinary skill in the art and may depend on the condition being treated and the route of administration.

The constructs may also be delivered with delivery vehicles such as viral sequences, viral particles, liposome formulations, lipofectin, precipitating agents, etc. Such methods of delivery are known in the art. For example, the polynucleotide construct can be delivered specifically to hepatocytes through the method of Wu et al., J. Biol. Chem. 264:6985-16987 (1989).

In certain embodiments, the polynucleotide constructs are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., Proc. Natl. Acad. Sci. USA (1987) 84:7413-7416); mRNA (Malone et al., Proc. Natl. Acad. Sci. USA (1989) 86:6077-6081); and purified transcription factors (Debs et al., J. Biol. Chem. (1990) 265:10189-10192), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner et al., Proc. Natl Acad. Sci. USA (1987) 84:7413-7416). Other commercially available liposomes include transfectace (DDAB/DOPE) and DOTAP/DOPE (Boehringer).

Other cationic liposomes can be prepared from readily available materials using techniques well known in the art. See, e.g. PCT Application No. WO 90/11092 for a description of the synthesis of DOTAP (1,2-bis(oleoyloxy)-3-(trimethylammonio)propane) liposomes. Preparation of DOTMA liposomes is explained in the literature, see, e.g., P. Felgner et al., Proc. Natl. Acad. Sci. USA 84:7413-7417. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphosphatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15□C. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., Methods of Immunology (1983), 101:512-527. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include Ca2+-EDTA chelation (Papahadjopoulos et al., Biochim. Biophys. Acta (1975) 394:483; Wilson et al., Cell (1979) 17:77); ether injection (Deamer, D. and Bangham, A., Biochim. Biophys. Acta (1976) 443:629; Ostro et al., Biochem. Biophys. Res. Commun. (1977) 76:836; Fraley et al., Proc. Natl. Acad. Sci. USA (1979) 76:3348); detergent dialysis (Enoch, H. and Strittmatter, P., Proc. Natl. Acad. Sci. USA (1979) 76:145); and reverse-phase evaporation (REV) (Fraley et al., J. Biol. Chem. (1980) 255: 10431; Szoka, F. and Papahadjopoulos, D., Proc. Natl. Acad. Sci. USA (1978) 75:145; Schaefer-Ridder et al., Science (1982) 215:166).

Additional examples of useful cationic lipids include dipalmitoyl-phosphatidylethanolamine 5-carboxyspen-nylamide (DPPES); 5-carboxyspermylglycine dioctadecylamide (DOGS); dimethyldioctdecyl-ammonium bromide (DDAB); and (±)-N,N-dimethyl-N-[2-(sperminecarboxamido)ethyl]-2,3-bis(dioleyloxy)-1-propaniminium pentahydrochloride (DOSPA). Non-diether cationic lipids, such as DL-1,2-dioleoyl-3-dimethylaminopropyl-β-hydroxyethylammonium (DORI ester), 1,2-O-dioleyl-3-dimethylaminopropyl-β-hydroxethylammonium (DORIE diether), 1-O-oleyl-2-oleoyl-3-dimethylaminopropyl-β-hydroxyethylammonium (DORI ester/ether), and their salts promote in vivo gene delivery. Cationic cholesterol derivatives such as 3β[N—(N',N'-dimethylaminoethane)-carbomoyl]-chloesterol (DC-Chol), are also useful.

Preferred cationic lipids include: (±)-N-(2-hydroxyethyl)-N,N-dimethyl-2,3-bis(tetradecyloxy)-1-propaniminium bromide; 3,5-(N,N-di-lysyl)diamino-benzoylglycyl-3-(DL-1,2-dioleoyl-dimethylaminopropyl-β-hydroxyethylamine) (DLYS-DABA-GLY-DORI diester); 3,5-(NN-dilysyl)-diaminobenzoyl-3-(DL-1,2-dioleoyl-dimethylaminopropyl-β-hydroxyethylamine) (DLYS-DABA-DORI diester); and 1,2-dioleoyl-sn-glycero-3-phosphoethanolamine. Also preferred is the combinations of the following lipids: (±)-N-(2-hydroxyethyl)-N,N-dimethyl-2,3-bis(tetradecyloxy)-1-propaniminium bromide and 1,2-dioleoyl-sn-glycero-3-phosphoethanolamine; and (±)-N-(2-hydroxyethyl)-N,N-dimethyl-2,3-bis(tetradecyloxy)-1-propaniminium bromide, and 1,2-dioleoyl-sn-glycero-3-phosphoethanolamine in a 1:1 ratio.

The lipid formulations may have a cationic lipid alone, or also include a neutral lipid such as cardiolipin, phosphatidylcholine, phosphatidylethanolamine, dioleoylphosphatylcholine, dioleoylphosphatidyl-ethanolamine, 1,2-dioleoyl-sn-glycero-3-phosphatidylethanolamine (DOPE), sphingomyelin, and mono-, di- or tri-acylglycerol).

Lipid formulations may also have cationic lipid together with a lysophosphatide. The lysophosphatide may have a neutral or a negative head group. Useful lysophosphatides include lysophosphatidylcholine, lysophosphatidyl-ethanolamine, and 1-oleoyl lysophosphatidylcholine. Lysophosphatide lipids are present Other additives, such as cholesterol, fatty acid, ganglioside, glycolipid, neobee, niosome, prostaglandin, sphingolipid, and any other natural or synthetic amphiphiles, can be used. A preferred molar ratio of cationic lipid to neutral lipid in these lipid formulations is from about 9:1 to about 1:9; an equimolar ratio is more preferred in the lipid-containing formulation in a 1:2 ratio of lysolipid to cationic lipid.

Generally, the ratio of DNA to liposomes will be from about 10:1 to about 1:10. Preferably, the ratio will be from about 5:1 to about 1:5. More preferably, the ratio will be about 3:1 to about 1:3. Still more preferably, the ratio will be about 1:1.

U.S. Pat. No. 5,676,954 reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication no. WO 94/9469 provide cationic lipids for use in transfecting DNA into cells and mammals. U.S. Pat. Nos. 5,589,466, 5,693,622, 5,580,859, 5,703,055, and international publication no. WO 94/9469 provide methods for delivering DNA-cationic lipid complexes to mammals.

In certain other embodiments, cells are engineered, ex vivo or in vivo, with the polynucleotide operably linked to a promoter contained in an adenovirus vector. Adenovirus can be manipulated such that it encodes and expresses the desired gene product, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz, A. R. et al. (1974) Am. Rev. Respir. Dis. 109:233-238). Finally, adenovirus mediated gene transfer has been demonstrated in a number of instances including transfer of alpha-1-antitrypsin and CFTR to the lungs of cotton rats (Rosenfeld, M. A. et al. (1991) Science 252:431434; Rosenfeld et al., (1992) Cell 68:143-155). Furthermore, extensive studies to attempt to establish adenovirus as a causative agent in human cancer were uniformly negative (Green, M. et al. (1979) Proc. Natl. Acad. Sci. USA 76:6606).

Suitable adenoviral vectors useful in the present invention are described, for example, in Kozarsky and Wilson, Curr. Opin. Genet. Devel. 3:499-503 (1993); Rosenfeld et al., Cell 68:143-155 (1992); Engelhardt et al., Human Genet. Ther. 4:759-769 (1993); Yang et al., Nature Genet. 7:362-369 (1994); Wilson et al., Nature 365:691-692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, for example, the polynucleotide of the present invention, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, N., Curr. Topics in Microbiol. Immunol. 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host cell integration. The polynucleotide construct is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the polynucleotide construct. These viral particles are then used to transduce eukaryotic cells, either ex vivo or in vivo. The transduced cells will contain the polynucleotide construct integrated into its genome, and will express the molecule of interest.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications. For example, direct injection of naked calcium phosphate-precipitated plasmid into rat liver and rat spleen or a protein-coated plasmid into the portal vein has resulted in gene expression of the foreign gene in the rat livers (Kaneda et al., Science 243:375 (1989)).

A preferred method of local administration is by direct injection. Preferably, a recombinant molecule of the present invention complexed with a delivery vehicle is administered by direct injection into or locally within the area of the liver. Administration of a composition locally within the area of the liver refers to injecting the composition centimeters and preferably, millimeters within the liver.

Another method of local administration is to contact a polynucleotide-promoter construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site, for example, ligands for targeting the vehicle to a tissue of interest. Targeting vehicles for other tissues and organs are well known to skilled artisans.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA 189: 11277-11281, 1992, which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian.

Direct administration of a DNA construct coding for a compound of the invention can be suitably accomplished for expression of the fusion compound within cells of the subject. Also, rather than directly administering nucleic acids coding for a compound of the invention to a subject, host compatible cells into which such nucleic acids have been introduced may be administered to the subject. Upon administration to a subject, such engineered cells can then express in vivo the compound of the invention. Such engineered cells can be administered to a subject to induce an immune response or alternatively to suppress an immune response, as disclosed herein.

A treatment method for suppression of an immune response provides for administration of a compound of the invention in which the peptide is a TCR antagonist or partial agonist. See Sette et al., Ann. Rev. Immunol. 12:413-431 (1994)). Peptides that are TCR antagonists or partial agonists can be readily identified and selected by the in vitro protocols identified above. A compound of the invention that contains a peptide that is a TCR antagonist or partial agonist is particularly preferred for treatment of allergies and autoimmune diseases.

Immunosuppressive therapies of the invention also may be used in combination with other known immunosuppressive agents such as anti-inflammatory drugs to provide a more effective treatment of a T cell-mediated disorder. For example, other immunosuppressive agents useful in conjunction with the compounds of the invention include anti-inflammatory agents such as corticosteroids and nonsteroidal drugs.

The invention also provides methods for invoking an immune response in a mammal such as a human, including vaccinating a mammal with a compound or composition described herein.

The compounds of the invention are useful for raising an immune response and treating hyperproliferative disorders. Examples of hyperproliferative disorders that can be treated by the compounds of the invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated by the compounds of the invention. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

The compounds of the present invention are also useful for raising an immune response against infectious agents. Viruses are one example of an infectious agent that can cause disease or symptoms that can be treated by the compounds of the invention. Examples of viruses, include, but are not limited to the following DNA and RNA viral families: Arbovirus, Adenoviridae, Arenaviridae, Arterivirus, Bimaviridae, Bunyaviridae, Caliciviridae, Circoviridae, Coronaviridae, Flaviviridae, Hepadnaviridae (hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, measles, mumps, parainfluenza, rabies, the common cold, Polio, leukemia, Rubella, sexually transmitted diseases, skin diseases (e.g., Kaposi's, warts), and viremia.

Similarly, bacterial or fungal agents that can cause disease or symptoms and that can be treated by the compounds of the invention include, but are not limited to, the following Gram-Negative and Gram-positive bacterial families and fungi: Actinomycetales (e.g., *Corynebacterium, Mycobacterium, Norcardia*), Aspergillosis, Bacillaceae (e.g., Anthrax, *Clostridium*), Bacteroidaceae, Blastomycosis, *Bordetella, Borrelia*, Brucellosis, Candidiasis, *Campylobacter*, Coccidioidomycosis, Cryptococcosis, Dermatocycoses, Enterobacteriaceae (*Klebsiella, Salmonella, Serratia, Yersinia*), Erysipelothrix, *Helicobacter*, Legionellosis, Leptospirosis, *Listeria*, Mycoplasmatales, Neisseriaceae (e.g., Acinetobacter, Gonorrhea, Menigococcal), Pasteurellacea Infections (e.g., *Actinobacillus*, Heamophilus, *Pasteurella*), *Pseudomonas*, Rickettsiaceae, Chlamydiaceae, Syphilis, and *Staphylococcal*. These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections.

Moreover, parasitic agents causing disease or symptoms that can be treated by the compounds of the invention include, but are not limited to, the following families: amebiasis, babesiosis, coccidiosis, cryptosporidiosis, dientamoebiasis, dourine, ectoparasitic, giardiasis, helminthiasis, leishmaniasis, theileriasis, toxoplasmosis, trypanosomiasis, and trichomonas.

Additionally, the compounds of the invention are useful for treating autoimmune diseases. An autoimmune disease is characterized by the attack by the immune system on the tissues of the victim. In autoimmune diseases, the recognition of tissues as "self" apparently does not occur, and the tissue of the afflicted subject is treated as an invader—i.e., the immune system sets about destroying this presumed foreign target. The compounds of the present invention are therefor useful for treating autoimmune diseases by desensitizing the immune system to these self antigens by provided a TCR signal to T cells without a costimulatory signal or with an inhibitory signal.

Examples of autoimmune diseases which may be treated using the compounds of the present invention include, but are not limited to Addison's Disease, hemolytic anemia, antiphospholipid syndrome, rheumatoid arthritis, dermatitis, allergic encephalomyelitis, glomerulonephritis, Goodpasture's Syndrome, Graves' Disease, multiple sclerosis, myasthenia gravis, neuritis, ophthalmia, bullous pemphigoid, pemphigus, polyendocrinopathies, purpura, Reiter's Disease, Stiff-Man Syndrome, autoimmune thyroiditis, systemic lupus erythematosus, autoimmune pulmonary inflammation, Guillain-Barre Syndrome, insulin dependent diabetes mellitus, autoimmune inflammatory eye disease, autoimmune hemolysis, psoriasis, juvenile diabetes, primary idiopathic myxedema, autoimmune asthma, scleroderma, chronic hepatitis, hypogonadism, pernicious anemia, vitiligo, alopecia areata, Coeliac disease, autoimmune enteropathy syndrome, idiopathic thrombocytic purpura, acquired splenic atrophy, idiopathic diabetes insipidus, infertility due to antispermatazoan antibodies, sudden hearing loss, sensoneural hearing loss, polymyositis, autoimmune demyelinating diseases, traverse myelitis, ataxic sclerosis, progressive systemic sclerosis, dermatomyositis, polyarteritis nodosa, idiopathic facial paralysis, cryoglobulinemia, inflammatory bowel diseases, Hashimoto's disease, adrenalitis, hypoparathyroidism, and ulcerative colitis.

Similarly, allergic reactions and conditions, such as asthma (particularly allergic asthma) or other respiratory problems, may also be treated by compounds of the invention. Moreover, the compounds of the invention can be used to treat anaphylaxis, hypersensitivity to an antigenic molecule, or blood group incompatibility.

The compounds of the invention may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of the compounds of the invention that inhibit an immune response may be an effective therapy in preventing organ rejection or GVHD.

The compounds of the invention which can inhibit an immune response are also useful for treating and/or preventing atherosclerosis; olitis; regional enteritis; adult respiratory distress syndrome; local manifestations of drug reactions, such as dermatitis, etc.; inflammation-associated or allergic reaction patterns of the slin; atopic dermatitis and infantile eczema; contact dermatitis; psoriasis; lichen planus; allergic enteropathies; allergic rhinitis; bronchial asthma; hypersensitivity or destructive responses to infectious agents; poststreptococcal diseases, e.g. cardiac manifestations of rheumatic fever, and the like.

EXAMPLES

Example 1

Anti-Tumor Antibody-MIC-A or B or ULBP Conjugates or Fusion Proteins

Targeting a high density of MHC class I-related molecule such as MIC-A or -B, ULBP or CD1d on the surface of tumor cells will activate different effector cells such as NK, NKT, or T cells and induce them to kill target tumor cells.

It has previously been shown experimentally and clinically that radiolabeled or fluorescent labeled mAbs directed against TAA can be specifically targeted in vivo on tumor cells (Delaloye et al., J. Clin. Invest. 77:301 (1986); and Folli et al., Proc. Natl. Acad. Sci. USA 89:7973 (1992)). Thus our general strategy will be to couple monomorphic MHC class I-related proteins to anti-TAA mAbs or fragments of mAbs in order to target them on tumor cells. The interest of the proposed strategy is that it will take advantage of both the efficient targeting properties of high affinity anti-TAA mAbs and the powerful and rapid activation of effector cells known to play an essential role in innate immunity.

A combined strategy of tumor targeting has been developed, using monoclonal antibodies (mAbs) specific for a tumor-associated antigen (TAA), which are coupled to a soluble classical MHC class I molecule loaded with a highly antigenic viral peptide specific for cytotoxic T lymphocytes (CTL). Thus, the CTL are activated and selectively kill the targeted cancer cells.

In a first approach, they have developed tetramers of HLA-A2 loaded with the immunodominant Flu-MA peptide and coupled to either one of 3 different Fab' fragments from mAbs specific for TAA (anti-CEA, anti-ErbB-2 or anti-CD20). It was demonstrated that tumor expressing the relevant TAA were rendered susceptible to efficient lysis by Flu-Ma peptide specific cytotoxic T lymphocytes (Robert et al., *Eur. J. Immunol.* 30:3165 (2000)).

In a second step, the inventors have demonstrated that also monomers of Fab-HLA-A2/Flu-peptide conjugates are active, but only when they reach their target and are oligomerized on the surface of the tumor cells (Robert et al., Cancer Immunity (2001)). This property presents several advantages to the multimerized conjugates also developed by others (Ogg et al., Br. J. Cancer 82:1058 (2000); Savage et al., Int. J. Cancer 98:561 (2002)). First, monomers do not induce significant activation in solution and hence can be injected in larger amounts without side effects. Second, technically, it is easier to produce monomeric forms of conjugates or fusion proteins in amounts necessary for patient treatment (see PCT/US01/17184, WO 01/90198).

One limitation of MHC class I/peptide complexes are their polymorphism, which means that a large pool of conjugates should be developed to be able to treat the great majority of patients. That is the reason why in the present invention, we are introducing the socalled non-polymorphic MHC class I related molecules. They differ from MHC class I molecules, not only because they are non-polymorphic, but also because they contain, either no antigenic peptide for the MIC-A/B or ULBP molecules, or a glycolipid antigen for the CD1d molecules. In addition, these class I related molecules activate other types of effector cells belonging to the innate immune response, namely NK and NKT cells.

Among the first monomorphic class I related molecules, which have been described, are the MIC-A and -B, which have a high degree of homology between each other (84%) (Bauer et al., Science 285:727 (1999); Li et al., Immunity 10:577 (1999)). Contrary to the classical MHC class I molecules which form an heterodimer between the heavy chain and the B-2 microglobulin, the MIC-A and -B consist of a single heavy chain, which has only a low degree of homology with the heavy chain of classical MHC class I (about 30%) (Cosman et al., Immunity 14:123 (2001)).

The crystal structure of MIC-A has been recently established (Li et al., Immunity 10:577 (1999)). It revealed a dramatically altered MHC class I fold, both in detail and overall domain organization. There is only a remnant of a peptide binding groove and a loss of B-2 microglobulin binding site. The expression of MIC-A and -B protein is essentially restricted to gut epithelium and the corresponding genes appear to be under the control of a heat-shock promoter element. Thus, the expression of MIC-A can be induced on the epithelial cells by various stresses, including viral infection and malignant transformation (Groh et al., Proc. Natl. Acad. Sci. USA 96:6879 (1999)).

One of the major biological properties of MIC-A and -B is to bind specifically to the NKG2D activating receptor present on NK cells, as well as on CD8 T cells expressing also, either the y-8 or the a-B antigen receptor. Through this binding to NKG2D receptor, the MIC-A and -B can act as a natural antigen and activate NK and T cells and induce them to kill the epithelial cells overexpressing the MIC proteins. This activation of effector cells is more rapid than the system of acquired immunity and represents a first line of defense belonging to the innate immunity (Groh et al., Proc. Natl. Acad. Sci. USA 96:6879 (1999)).

ULBPs are a different group of monomorphic MHC class I related proteins, which are GPI-anchored and have only 25% amino acid sequence homology with classical MHC class I molecules and also a low sequence homology with MIC-A or -B (23%) (Cosman et al., Immunity 14:123 (2001)). The ULBPs are overexpressed in cells infected with the human cytomegaloviras (HCMV) and they share with MIC-A and -B the property of binding the activating NKG2D receptor. Thus, human cells infected with HCMV through overexpression of ULBPs can stimulate cytokine and chemokine production by NK cells and confer susceptibility to NK cells cytotoxicity (Cosman et al., Immunity 14:123 (2001)). In the present strategy, ULBPs conjugated to antibodies are used as ligands for NKG2D receptor and are targeted on tunor cells independently of HCMV infection.

The CD1 family represents another non-polymorphic lineage of class I related antigen-presenting molecules. Some T cells recognize bacterial and self-glycolipids associated with CD1 molecules (Porcelli et al., Annu. Rev. Immunol. 17:297 (1999); Shamshiev et al., Eur. J. Immunol. 29:1667 (1999); Park and Bendelac, Nature 406:788 (2000); and Matsuda and Kronenberg, Curr. Opin. Immunol. 13:19 (2001)). Five CD1 monomorphic isoforms have been identified (CD1 a, b, c, d and e), which have a high degree of homology among themselves and a lower degree of homology with the classical MHC class I molecules (almost no homology on alpha-1 and up to 35% on alpha-2 and alpha-3 domains). Despite low sequence homology, the resolution of the crystal structure of mouse CD1d revealed a folding similar to MHC class I (Zeng et al., Science 277:339 (1997)). The major difference resides in the antigen binding groove which is composed of only two very hydrophobic and deep pockets, that are likely to accomodate the lipidic tail of the antigen, while presenting the carbohydrate part to the T cell receptor. Numerous reports have described foreign and self-glycolipid presentation by CD1 molecules in bacterial infections and autoimmunity and their role in innate as well as acquired imunity has been established (Shamshiev et al., Eur. J. Immunol. 29:1667 (1999); Park and Bendelac, Nature 406:788 (2000); and Matsuda and Kronenberg, Curr. Opin. Immunol. 13:19 (2001)).

Of importance for the present invention, the CD1d molecule has been broadly associated with anti-tumor immunity (Wilson et al., Trends Mol. Med. 8:225 (2002); and Brutkiewicz et al., Crit. Rev. Oncol. Hematol. 41:287 (2002)). Several other characteristics have drawn much attention on CD1d in the past few years which makes this molecule very attractive for our strategy. First, CD1d-restricted T cells are characterized both in mice and humans by a highly restricted TCR repertoire and expression of some NK markers (CD161, NKG2d). They were therefore called NKT cells and are considered as part of innate immunity (Bendelac et al., Science 268:863 (1995)). Second, NKT cells have an unusual ability of secreting both Th1 and Th2 cytokines and their role in inflammation, autoimmunity and tumor immunity is being extensively investigated (Bendelac et al., Science 268:863 (1995); Chen and Paul, J. Immunol. 159: 2240 (1997); and Exley et al., J. Exp. Med. 186:109 (1997)). Last, the natural ligands of CD1d are still largely unknown but a high affinity ligand and potent activator of NKT cells has been isolated from an extract of a marine sponge known in japanese medicine to have antimetastatic effects. This glycoshingolipid absent in mammal tissues was characterized as alpha-galactosylceramide (alpha-GalCer) and has been used both in vitro and in vivo in various tumor models. It was confirmed that alpha-GalCer antimetastatic activity is mediated by CD1d-restricted NKT cells (Wilson et al., Trends Mol. Med. 8:225 (2002); and Brutkiewicz et al., Crit. Rev. Oncol. Hematol. 41:287 (2002)).

a) Chemical conjugate. MIC-A or -B or ULBP molecules are produced in bacteria or in an eukaryotic cells with a mutation introducing a cysteine at the C-terminus, as described for HLA-A2 by Robert et al. (Robert et al., Cancer Immunity (2001)). Then, the free SH group on the cysteine is saturated with an excess of bismaleimide coupling reagent. After elimination of the excess bis-maleimide, the maleimide derivatized MIC-A/B or ULBP is chemically coupled to the free SH groups of the cysteines from the Fab' fragments of a high affinity mAb anti-TAA, as described (Robert et al., Cancer Immunity (2001)).

b) Fusion protein. The genes encoding MIC-A or -B, or ULBP are fused to the genes encoding either a single chain antibody fragment or a Fab fragment directed against a human TAA. The genes are fused so that the synthesis starts either at the N-terminus of the MIC-A/B or ULBP and continues with the antibody fragment or at the N-terminus of the antibody fragment and be followed by the MIC-A/B or ULBP.

In both cases, a semi-rigid amino-acid spacer sequence is placed between the two molecules to avoid steric hindrance. The best form of fusion protein is selected by in vitro testing. For these tests the different fusion proteins are incubated on $^{51}$Cr-labeled target tumor cells bearing the relevant, TAA and different amounts of NK cells are added. The conjugate, which induces the most efficient lysis, as determined by $^{51}$Cr release is selected.

c) In vivo evaluation of the conjugate or fusion proteins. The conjugates or fusion proteins which gave the best in vitro results in the $^{51}$Cr release assay are then tested in vivo first in experimental animal models and subsequently in tumor bearing patients.

The experimental animal bearing a tumor known to express the relevant TAA are injected i.v. with increasing amounts of antibody-MIC-A/-B or ULBP conjugates or fusion proteins. One or two days after injection of the conjugate or fusion proteins, the animal or the patients are treated with a cytoline or chemoline such as interferon-gamma or IL-12 or IL-2, known to stimulate NK cells activity. The tumor size is monitored to verify that the tumor cells, which have been targeted with an optimal dose of conjugates or fusion proteins, are selectively killed by NK cells.

Example 2

Anti-Tumor Antibody CD1d Conjugates or Fusion Proteins a) Chemical coupling. Recombinant soluble human CD1d are produced in eukaryotic cells with a mutation at the C-terminus introducing a single cysteine residue. After derivation of the free cysteine with an excess of bis-maleimide and elimination of the excess of free bis-maleimide, the maleimide derivatized CD1d is coupled to the free SH group of eysteines from an Fab' fragment of a high affinity anti-TAA mAb, as described previously (Robert et al., Cancer Immunity (2001)).

b) Fusion protein. The cDNA of soluble CD1d protein is fused to the sequences encoding scFv or Fab fragment from a high affinity anti-TAA mAb. Two types of fusions will be made so that either the CD-1d will be expressed at the N-terminus, followed by the antibody fragment or the opposite. In both cases, a semi-rigid amino-acid spacer sequence is placed between the antibody fragment and the CD1d molecule to avoid steric hindrance. The most active form of fusion protein is selected in vitro on target cancer cells expressing the relevant TAA, as described in Example 1b, except that the CD1d in the fusion protein is loaded with alpha-galactosylceramide and that NKT cells are used as effector cells instead of NK cells.

c) In vivo evaluation of the conjugate or fusion protein. The conjugate or fusion proteins which gave the best in vitro results are tested in vivo, first in tumor bearing experimental animals and subsequently in patients, as described in example 1c, except that the antibody fragment-CD1d conjugate or fusion protein is loaded with alpha-galactosylceramide or with different activating glycolipids.

Alternatively, the antibody-CD1d conjugate or fusion protein is injected without alpha-galactosylceramide or glycolipids, in order that the CD1d molecules, targeted on tumor cells, become progressively loaded with endogenous glycolipids.

A third strategy is evaluated in vivo in experimental animals. It consists of the injection in a first step of alpha-galactosylceramide in order to stimulate activation and proliferation of NKT cells, followed in a second step 8 to 24 hours later, by the injection of the antibody-CD1d conjugate.

Example 3

Anti-Neoangiogenesis Antibody-MHC Class I Related Conjugates or Fusion Proteins

It is now broadly accepted that neoangiogenesis represents an essential condition for tumor development and growth. Thus, one application of our strategy consists in antibody targeting of monomorphic MHC class I related protein such as MIC-A/B, ULCBPs or CD1d molecules in the neovessels. The presence of monomorphic MHC class I related molecules in the neovessels will focus NK and NKT cells activity in the tumor area. The activation of NK and NKT cells in the tumor neovessels have three beneficial effects: 1) It increases inflammation in the tumor area and enhances anti-tumor immune response by recruitment of antigen presenting cells and T lymphocytes through local secretion of cytokines and interleukins; 2) It has a direct cytotoxic effect against endothelial cells from tumor neovessels and thus decreases blood flow in the tumor and 3) The increased secretion of TNF and other cytokines by macrophages ultimately induce the collapse of the tumor neovasculature.

Numerous mAbs directed against antigens associated with tumor neovessels have been described, such as mAbs against avB3 integrins, TNF receptors, platelet derived growth factor receptor, or the ED-B oncofoetal domain of fibronection (Halin et al., Nat. Biotechnol. 20:2264 (2002)) and many others (for review, Nature Biotechnol. 17:963) and are be used in this strategy of tumor treatment.

b) Chemical coupling and fusion between mAbs against neoangiogenesis antigens and monomorphic MHC class I related proteins. The synthesis of chemical conjugates and fusion proteins between the mAbs anti-neoangiogenesis antigens and the MICA-A/B, ULBPs or CD1d is performed as described in Examples 1 and 2, paragraph a) and b).

c) In vitro evaluation of the conjugates or fusion proteins on endothelial cells. The effect of the different conjugates or fusion proteins is tested on human umbilical vein endothelial cells (HUVEC), or on tumor cell lines expressing neoangiogenesis antigens in the presence of either NK or NKT cells. The target cells are $^{51}$Cr-labeled and their lysis by effector cells is measured in presence or absence of conjugate or fusion protein as described for tumor target cells in Examples 1 and 2, c). Alternatively, the degree of activation of NK or NKT cells in presence of target cells coated or not with the conjugates or fusion proteins is evaluated by measurement of the release of cytokines or interleukins such as IFN-gamma or IL4 by NK or NKT cells.

d) In vivo evaluation of conjugates or fusion proteins on tumor bearing experimental animals. The effect of intravenous injection of conjugates or fusion proteins on tumor growth is evaluated in tumor bearing mice. Furthermore the tumor vascular parameters, such as blood flow, blood volume and vascular permeability is analyzed during conjugate or fusion protein treatment, as previously described for TNF treatment (Folli et al., Proc. Natl. Acad. Sci. USA 89:7973 (1992)).

Example 4

Construction of IgG-Avidin Fusion Protein Complexed with Soluble CD1d

An antibody fusion molecule is formed that contains either all (IgG-avidin), or a portion (F(ab)-avidin and F(ab')2-avidin) of an antibody molecule fused in frame with the chicken avidin open reading frame. The chimeric Ig Heavy chain-avidin along with the complementing Ig Light Chain are produced in Drosophila cells in three steps. In step one, PCR is used to create the cloning cassette for VH, including appropriate regions preceded by a signal sequence (SS) for secretion and followed by a linker with an embedded KpnI restriction site. In step two, PCR is used to amplify the avidin gene. Finally, in step three, restriction digestion is used at the KpnI site followed by ligation to combine the two fragments. The IgG1 and avidin proteins are separated by a 12 amino acid linker.

The extracellular portion of CD1d along with β2-microglobulin (β2M) is produced separately in Drosophila. The CD1d/B2M molecule is biotinylated, incubated with the Ig-Avidin fusion protein and purified.

1. Construction of VH cassette. Standard PCR is used to amplify the relevant portions of IgG with a pre-configured VH insertion site from a previously described template. The PCR product is gel purified according to standard procedure. Specifically, an IgG1 construct that allows for insertion of a variable gene of interest through BssHI and BstEII restriction sites has been generated (U.S. Appl. Publ. No. 2003/0104402, published Jun. 5, 2003). This construct is available as template for PCR using the following primers:

For the F(ab) fragment: (7) Sense 5' AATTGCGGCCGC AAACCATGGGATGGAGCTGTATCATC 3' (SEQ ID NO:3) (NotI and NcoI sites in bold); and (8) Anti-sense 5' CGGGGGTACCTGACCCACCGCCTCCTTTCTTG-TCCACCTTGGTGTT 3' (SEQ ID NO:4) (linker is in bold; KpnI site is bolded and underlined.).

For the (Fab'2) fragment: (7) Sense 5' AATTGCGGCCGC AAACCATGGGATGGAGCTGTATCATC 3' (SEQ ID NO:5) (NotI and NcoI sites in bold); and (8) Anti-sense 5' CGGGGTACCTGACCCACCGCCTCCTGGGCACGGT-GGGCATGTGTG 3' (SEQ ID NO:6) (linker is in bold; KpnI site is bolded and underlined).

For full IgG1: (7) Sense 5' AATTGCGGCCGCAAAC-CATGGG ATGGAGCTGTATCATC 3' (SEQ ID NO:7) (NotI and NcoI sites in bold); and (8) Anti-sense 5' CGG GGTACCTGACCCACCGCCTCC TTTACCCGGA-GACAGGGAGAG 3' (SEQ ID NO:8) (linker is in bold; KpnI site is bolded and underlined).

In other embodiments, the CH1 region derives from other immunoglobulin isotypes, including IgG2, IgG3, IgG4, IgA, IgM, IgD or IgE. Particularly preferred is the longer and more flexible IgG3 hinge region.

2. Construction of Chick Avidin. The fragment containing the mature avidin polypeptide (minus the signal sequence) is generated by standard PCR using plasmid DNA as template and the following primers: (1) Sense 5' CGGGGTACCG-GAGGCGGTGGGTCAGCCAGAAAGTGCTCGC 3' (SEQ ID NO:9) (linker is in bold; KpnI restriction site is bolded and underlined); and (14) Anti-sense 5'-CGAC-CGGT CTCCTTCTGTGTGCGCAGGC-3' (SEQ ID NO:10) (AgeI restriction site is in bold). The PCR product is gel purified according to standard procedure.

3. Assembled product. The above fragments "1" and "2" are joined by restriction digestion at the KpnI site followed by ligation employing standard protocols. The complete gene is designed for insertion in frame with a C terminal 6-His tag into the Drosophila expression vector pMT/V5-His (Invitrogen). This strategy is not limited to the use of this vector or a drosophila expression system. Specifically, the use of other expression vectors simply requires re-engineering of the restriction digestion sites flanking the complete construct (NotI and AgeI). The nucleotide and protein sequences of each construct below are shown without an inserted VH-gene. Any given VH-gene can be inserted between the BssHII (bold) and BstEII (dashed underline) sites.

The final sequence is for the F(ab) construct is: GCGGCCGCAAACC ATGGGATGGAGCTGTATCATCC-- TCTTCTTGGTAGCAACAGCTACAGGCGCGCATAT GGTCACCTCTCCTCAGCCTCCACCAAGGGCCCATC GGTCTTCCCCCTGGCACCCTCCTCCAAGAGCAC-CTCTGGGGGCACA GCGGCCCTGGGCTGCCTGGT-CAAGGACTACTTCCCCGAACCGGTGA CGGT-GTCGTGGAACTCAGGCGCCCTGACCAGCGGCGT-GCACACCTT CCCGGCTGTCCTACAGTCCTCAG-GACTCTACTCCCTCAGCAGCGTC GTGACCGTGC-CCTCCAGCAGCTTGGGCACCCAGACCTACATCT-GCA ACGTGAATCACAAGCCCAGCAACACCAAGGTGGA-CAAGAAAGGAGGCGGTGGGTCAG-GTACCGGAGGCGGTGGGTCAGCCAGAAAGT GCTCGCTGACTGGGAAATGGACCAAC-GATCTGGGCTCCAACATGAC CATCGGGGCTGT-GAACAGCAGAGGTGAATTCACAGGCACCTACAT CACAGCCGTAACAGCCACATCAAATGAGAT-CAAAGAGTCACCACT GCATGGGACACAAAACAC-CATCAACAAGAGGACCCAGCCCACCTT TGGCT-TCACCGTCAATTGGAAGTTTTCAGAGTCCACCA-CTGTCTTCA CGGGCCAGTGCTTCATAGACAG-GAATGGGAAGGAGGTCCTGAAGA CCATGTGGCT-GCTGCGGTCAAGTGTTAATGACATTGGTGAT-GACTG GAAAGCTACCAGGGTCGGCATCAACATCT-TCACTCGCCTGCGCACA CAGAAGGAG ACCGGTCATCATCACCATCACCATTGA (SEQ ID NO:11) (double underline: NotI restriction site; single underline: Signal sequence; bold: BssHII restriction site; dashed underline: BstEII restriction site; bold and underlined: linker; wavy underline: AgeI restriction site; italics and underlined: 6-His tag).

The F(ab) construct polypeptide sequence is: MGWSCI-ILFLVATATGAHMVTVSSASTKGPSVFPLAPSSKST-SGGTAA LGCLVKDYFPEPVTVSWNSGALTSGVHTF-PAVLQSSGLYSLSSVVTVP SSSLGTQTYICNVNHKPSNTKVDKK GGGGSGTGGGGSARKCSLTGK WTNDLGSNMTI-GAVNSRGEFTGTYITAVTATSNEIKESPLHGTQNTINK RTQPTFGFTVNWKFSESTTVFTGQCFIDRNGKEVLK-TMWLLRSSVNDI GDDWKATRVGINIFTRLRTQKETG HHHHHH(SEQ ID NO:12). The variable gene sequence is introduced at the upstream histidine in bold and the rest of the bolded amino acids are removed upon insertion of the variable gene sequence. The linker is bolded and underlined.

The F(ab'2) construct nucleotide sequence is:
GCGGCCGCAAACC
ATGGGATGGAGCTGTATCATCCTCTTC-
TTGGTAGCAACAGCTACAGGCGCGCATAT
GGTCACCGTCTCCTCAGCCTCCACCAAGGGCCC-
ATC GGTCTTCCCCCTGGCACCCTCCTCCAAGAG-
CACCTCTGGGGGCACA GCGGCCCTGGGCTGCCTG-
GTCAAGGACTACTTCCCCGAACCGGTGA CGGT-
GTCGTGGAACTCAGGCGCCCTGACCAGCGGCG-
TGCACACCTT CCCGGCTGTCCTACAGTCCTCAG-
GACTCTACTCCCTCAGCAGCGTC GTGACCGTGC-
CCTCCAGCAGCTTGGGCACCCAGACCTACATCT-
GCA
ACGTGAATCACAAGCCCAGCAACACCAAGGTGGA-
CAAGAAAGTTG AGCCCAAATCTTGTGACAAAACT-
CACACATGCCCACCGTGCCCA
GGAGGCGGTGGGTCAGGTACCGGAGGCGG-
TGGGTCAGCCAGAAA GTGCTCGCT-
GACTGGGAAATGGACCAACGATCTGGGCTC-
CAACATG ACCATCGGGGCTGTGAACAGCAGAGGT-
GAATTCACAGGCACCTAC
ATCACAGCCGTAACAGCCACATCAAATGAGAT-
CAAAGAGTCACCA CTGCATGGGACACAAAACAC-
CATCAACAAGAGGACCCAGCCCACC TTTGGCT-
TCACCGTCAATTGGAAGTTTTCAGAGTCCACCA-
CTGTCTT CACGGGCCAGTGCTTCATAGACAG-
GAATGGGAAGGAGGTCCTGAA GACCATGTGGCT-
GCTGCGGTCAAGTGTTAATGACATTGGTGATGAC
TGGAAAGCTACCAGGGTCGGCATCAACATCT-
TCACTCGCCTGCGCA CACAGAAGGAGA
ACCGGTCATCATCACCATCACCATTGA (SEQ ID
NO:13) (double underline: NotI restriction site; single
underline: Signal sequence; bold: BssHII restriction site;
dashed underline: BstEII restriction site; bold and underlined: linker; wavy underline: BamII restriction site.)

The F(ab'2) construct polypeptide sequence is:
MGWSCIILFLVATATGAHMVTVSSASTKGPSVF-
PLAPSSKSTSGGTAA LGCLVKDYFPEPVTVSWNS-
GALTSGVHTFPAVLQSSGLYSLSSVVTVP SSSLGTQ-
TYICNVNHKPSNTKVDKKVEPKSCDKTHTCPPCP
GGGGSGTGGGGSARKCSLTGKWTNDLGSNMTIG-
AVNSRGEFTGTYITAVTATS NEIKESPLHGTQNTINK-
RTQPTFGFTVNWKFSESTTVFTGQCFIDRNGK EVLK-
TMWLLRSSVNDIGDDWKATRVGINIFTRLRTQKE
TGHHHHHH (SEQ ID NO:14). The variable gene sequence
is introduced at the histidine in bold and the rest of the
bolded amino acids are removed upon insertion of the
variable gene sequence. The linker is bolded and underlined.

The full IgG1 construct nucleotide sequence is:
GCGGCCGCAAACC
ATGGGATGGAGCTGTATCATCCTCTTCTTGGTA-
GCAACAGCTACAGGCGCGCATAT
GGTCACCGTCTCCTCAGCCTCCACCAAGGGCCCATC
GGTCTTCCCCCTGGCACCCTCCTCCAAGAGCAC-
CTCTGGGGGCACA GCGGCCCTGGGCTGCCTGGT-
CAAGGACTACTTCCCCGAACCGGTGA CGGT-
GTCGTGGAACTCAGGCGCCCTGACCAGCGGCGT-
GCACACCTT CCCGGCTGTCCTACAGTCCTCAG-
GACTCTACTCCCTCAGCAGCGTC GTGACCGTGC-
CCTCCAGCAGCTTGGGCACCCAGACCTACATCT-
GCA
ACGTGAATCACAAGCCCAGCAACACCAAGGTGGA-
CAAGAAAGTTG AGCCCAAATCTTGTGACAAAACT-
CACACATGCCCACCGTGCCCAGC ACCTGAACTC-
CTGGGGGGACCGTCAGTCTTCCTCTTCCCCCC-
AAAA CCCAAGGACACCCTCATGATCTCCCGGAC-
CCCTGAGGTCACATGCG TGGTGGTGGACGTGAGC-
CACGAAGACCCTGAGGTCAAGTTCAACT
GGTACGTGGACGGCGTGGAGGTGCATAATGC-
CAAGACAAAGCCGC GGGAGGAGCAGTACAACAG-
CACGTACCGTGTGGTCAGCGTCCTCA CCGTCCTG-
CACCAGGACTGGCTGAATGGCAAGGAGTACAA-
GTGCA AGGTCTCCAACAAAGCCCTCCCAGC-
CCCCATCGAGAAAACCATCTC CAAAGC-
CAAAGGGCAGCCCCGAGAACCACAGGTGTACAC-
CCTGCC
CCCATCCCGGGATGAGCTGACCAAGAACCAG-
GTCAGCCTGACCTGC CTGGTCAAAGGCTTCTATC-
CCAGCGACATCGCCGTGGAGTGGGAGA
GCAATGGGCAGCCGGAGAACAACTACAAGAC-
CACGCCTCCCGTGC TGGACTCCGACGGCTCCTTCT-
TCCTCTACAGCAAGCTCACCGTGGA CAAGAGCAG-
GTGGCAGCAGGGGAACGTCTTCTCATGCTCCGTG-
ATG CATGAGGCTCTGCACAACCACTACACGCA-
GAAGAGCCTCTCCCTGT CTCCGGGTAAA
GGAGGCGGTGGGTCAGGTACCGGAGGCGGT
GGGTCAGCCAGAAAGTGCTCGCTGACTGGGAAA-
TGGACCAACGATCT GGGCTCCAACATGAC-
CATCGGGGCTGTGAACAGCAGAGGTGAATT CACA-
GGCACCTACATCACAGCCGTAACAGCCACAT-
CAAATGAGAT
CAAAGAGTCACCACTGCATGGGACACAAAACAC-
CATCAACAAGAG GACCCAGCCCACCTTTGGCT-
TCACCGTCAATTGGAAGTTTCAGAG TCCACCACT-
GTCTTCACGGGCCAGTGCTTCATAGACAGGAAT-
GGGA AGGAGGTCCTGAAGACCATGTGGCTGCT-
GCGGTCAAGTGTTAATGA CATTGGTGATGACTG-
GAAAGCTACCAGGGTCGGCATCAACATCTTC
ACTCGCCTGCGCACACAGAAGGAG
ACCGGTCATCATCACCATCACCATTGA (SEQ ID
NO:15) (double underline: NotI restriction site; single
underline: Signal sequence; bold: BssHII restriction site;
dashed underline: BstEII restriction site; bold and underlined: linker; wavy underline: BamHI restriction site).

The full IgG1 construct polypeptide sequence is:
MGWSCIILFLVATATGAHMVTVSSASTKGPSVF-
PLAPSSKSTSGGTAA LGCLVKDYFPEPVTVSWNS-
GALTSGVHTPAVLQSSGLYSLSSVVTVP SSSLGTQTY-
ICNVNHKPSNTKVDKKVEPKSCDKTHTCPPCPAPE-
LLGG PSVFLFPPKPKDTLMISRTPEVTCVVVD-
VSHEDPEVKFNWYVDGVEVH NAKTKPREEQYN-
STYRVVSVLTVLHQDWLNGKEYKCKVSNKALPAPI
EKTISKAKGQPREPQVYTLPPSRDELTKNQVSLT-
CLVKGFYPSDIAVE WESNGQPENNYKTTPPVLDS-
DGSFFLYSKLTVDKSRWQQGNVFSCSV MHEALHN-
HYTQKSLSLSPGK
GGGGSGTGGGGSARKCSLTGKWTND LGSNMTI-
GAVNSRGEFTGTYITAVTATSNEIKESPLHGTQNTINK-
RTQP TFGFTVNWKFSESTTVFTGQCFIDRNGKEVLK-
TMWLLRSSVNDIGDD WKATRVGINITRLRTQKE
TGHHHHHH (SEQ ID NO:16). The variable gene sequence
is introduced at the histidine in bold and the rest of the
bolded amino acids are removed upon insertion of the
variable gene sequence. The linker is bolded and underlined.

Example 5

Chimeric Kappa L Chain-Avidin

Employing the same strategy described above for fusion products with immunoglobulin heavy chain or heavy chain fragments, a chimeric kappa L chain is coupled in frame with avidin. Assembly takes place in a three-step process. In step one, PCR is employed to create the CL region preceded by a signal sequence for secretion and followed by a linker with an embedded KpnI restriction site. The kappa light chain constant region (CK) is PCR amplified from a previously described plasmid template with a pre-configured VL insertion site that allows for directional cloning of any immunoglobulin light chain variable region gene of interest at ApaLI and XhoI restriction sites (US20020123057, published Sep. 5, 2002). In step two the avidin gene preceded by the linker with a KpnI restriction site is amplified exactly as described above for heavy chain fusion products. Finally in step three the two fragments are joined by restriction digestion at the KpnI site followed by ligation employing standard protocols. The modifications of primer sequences required for amplification of the immunoglobulin light chain with either kappa or lambda light chain constant regions will be apparent to those skilled in the art.

Example 6

N Terminal Fusion Proteins

Employing strategies similar to those described above, chimeric molecules are constructed where avidin is fused in frame with the amino terminus of the immunoglobulin heavy or light chain. These molecules are assembled in a 3 step process. In step 1, avidin, including the signal sequence, is PCR amplified from a plasmid template. This PCR modification adds a NotI site at the 5' end, and a portion of the gly,ser linker and a KPNI site at the 3' end. In step 2, the entire immunoglobulin heavy chain or light chain genes (variable and constant domains, or constant domain with restriction endonuclease sites for the insertion of a V gene), without the signal sequence, is PCR amplified. This PCR modification adds a portion of the gly,ser linker and a KpnI site at the 5' end, and an AgeI site at the 3' end. Finally, in step three, the two fragments are joined by restriction digestion at the KpnI site followed by ligation employing standard protocols. The modifications of primer sequences required for amplification of these genes and the construction of these molecules will be apparent to those skilled in the art.

Example 7

Construction of Extracellular Domain of CD1d

1. Addition of Biotinylation Sequence to pMTN5-His. The pMTN5-His vector (Invitrogen) is a *Drosophila* expression vector. The purpose of this step is to modify this vector so that it contains a biotinylation sequence (BirA recognition sequence) in frame with a 6-His Tag at the C terminus. This allows for cloning of polypeptides of interest in frame with the BirA sequence and the 6-His Tag: (1) BirA Sense: 5'CCGGTggtggcggtctgaac gacatcttcgaggctcagaaaatcgaatggcacgaaT (SEQ ID NO:17); and (2) BirA Antisense: 5'CCGGAttcgtgccattcgattttctgagcctcgaagatgtcgttcagaccgccaccA (SEQ ID NO:18).

These 2 oligonucleotides are annealed together in vitro to create a double stranded oligo that contains an AGEI sticky end (bold) at both ends. This double stranded oligo is cloned into the AgeI site of pMT/V5-His, creating pMT/V5-BirA-His. The 3' AGEI site is destroyed by this cloning reaction, leaving a single AGEI site upstream and in frame with the BirA sequence.

2. Extracellular Domain of CD1d. Plasmid DNA or cDNA isolated from human bone marrow or spleen is used as a source of CD1d mRNA. The extracellular domain of CD1d is PCR amplified using the primers: (E1 sense): CAC GGTACCGATATGGGGTGCCTGCTGTTTCTGC (SEQ ID NO:19) (KPNI site is underlined); and (E1 antisense): CAGACCGGTCCAGTAGAGGACGATGTCCTG (SEQ ID NO:20) Age I site is underlined.

The CD1d extracellular product is digested with Kpn I and Age I and cloned into the KpnI and AgeI sites of pMT/V5-BirA-His A vector (E.1). The C terminus of CD1d is in frame with the BirA sequence and the 6 His tag encoded by the vector, and contains an additional Thr and Gly that are encoded by the 5' AgeI site, and a Ser and Gly encoded by the 3' AgeI site.

The final sequence is: GGTACCGAT ATGGGGTGCCTGCTGTTTCTGCTGCTCTGGGCG-CTCCTCCAGGCTTGGGGAAGCGCTGAAGTCCC-GCAAAGGCTTTTCCCCCTCCGCTGCCTC CAGATCTCGTCCTTCGCCAATAGCAGCTGGACGCG-CACCGACGGCT TGGCGTGGCTGGGGGAGCTGCA-GACGCACAGCTGGAGCAACGACT CGGACAC-CGTCCGCTCTCTGAAGCCTTGGTCCCAGGGC-ACGTTCAG CGACCAGCAGTGGGAGACGCTGCAG-CATATATTTCGGGTTTATCGA AGCAGCTTCACCA-GGGACGTGAAGGAATTCGCCAAAATGCTACGC TTATCCTATCCCTTGGAGCTCCAGGTGTCCGCTG-GCTGTGAGGTGC ACCCTGGGAACGCCT-CAAATAACTTCTTCCATGTAGCATTTCAAGG AAAAGATATCCTGAGTTTCCAAGGAACTTCT-TGGGAGCCAACCCAA GAGGCCCCACTTTGGG-TAAACTTGGCCATTCAAGTGCTCAACCAGG ACAAGTGGACGAGGGAAACAGTGCAGTGGCTCCT-TAATGGCACCT GCCCCCAATTTGTCAGTGGCCTC-CTTGAGTCAGGGAAGTCGGAACT GAAGAAGCAAGTGAAGCCCAAGGCCTGGCTGTC-CCGTGGCCCCAG TCCTGGCCCTGGCCGTCTGCT-GCTGGTGTGCCATGTCTCAGGATTCT ACCCAAAGC-CTGTATGGGTGAAGTGGATGCGGGGTGAGCAGGAGC AGCAGGGCACTCAGCCAGGGACATCCTGC-CCAATGCTGACGAGA CATGGTATCTCCGAGCAAC-CCTGGATGTGGTGGCTGGGGAGGCAGC TGGCCT-GTCCTGTCGGGTGAAGCACAGCAGTCTAGAG-GGCCAGGA CATCGTCCTCTACTGG ACCGGTGGCGGTCTGAACGACATCTT CGAG-GCTCAGAAAATCGAATGGCACGAA TCCGGTCATCATCACCATCACCATTGA (SEQ ID NO:21) (single underline: KPNI site; double underline: Signal Sequence; wavy Underline: 5' AgeI site; bold: BirA sequence; dashed underline: 3' AgeI site; italics: 6 His Tag).

The translated polypeptide sequence is:

(SEQ ID NO: 22)
MGCLLFLLLWALLQAWGSAEVPQRLFPLRCLQISSFANSSWTRTDGLA

WLGELQTHSWSNDSDTVRSLKPWSQGTFSDQQWETLQHIFRVYRSSF

TRDVKEFAKMLRLSYPLELQVSAGCEVHPGNASNNFFHVAFQGKDILS

FQGTSWEPTQEAPLWVNLAIQVLNQDKWTRETVQWLLNGTCPQFVS

GLLESGKSELKKQVKPKAWLSRGPSPGPGRLLLVCHVSGFYPKPVWV

KWMRGEQEQQGTQPGDILPNADETWYLRATLDVVAGEAAGLSCRVK

HSSLEGQDIVLYW<u>TG</u>GGGLNDIFEAQKIEWHE<u>SG</u>*HHHHHH*.

Example 8

Construction of β2 Microglobulin

The fragment encoding the entire open reading frame of β2-microglobulin is generated by standard PCR using plasmid DNA as template. This fragment is cloned into a

*Drosophila* expression vector such as pMT/V5-His. Cloning is designed so that there is not a 6-His Tag at the C terminal. This is easily accomplished by incorporating a "Stop" codon in the antisense primer immediately following the β2-microglobulin open reading frame. Methods to accomplish this construction are well known to those skilled in the art.

Example 9

Production and Purification of the Chimeric Antibody-Avidin/CD1d-β2-Microglobulin Complex Production of the antibody-avidin CD1d-β2-microglobulin complex is accomplished in 2 steps. In the first step, *Drosophila* S2 cells are transfected with the constructs encoding the chimeric antibody-avidin and the antibody light chain gene. High expressing clones are selected. At the same time a different aliquot of S2 cells is transfected with the CD1d construct and a construct encoding B2M and clones expressing high levels of the CD1d-β2-microglobulin complex are isolated.

A. Generation of *Drosophila* S2 cells stably transfected and producing antibody-avidin. *Drosophila* S2 cells are triply transfected with plasmids that encode 1) antibody-avidin (full IgG, F(ab), or F(ab')2; 2) antibody light chain; and 3) pCOHYGRO (Invitrogen). This plasmid confers resistance to the drug hygromycin. The triply transfected cells are selected with hygromycin and clones isolated. Expression of the recombinant antibody-avidin is induced in the cells by the addition of copper sulfate or cadmium chloride, and the cell supernatants are screened by ELISA using antibodies specific for antibody and avidin. The clones that express the highest amount of antibody-avidin complex are expanded and used to produce quantities of this molecule.

B. Production of the chimeric antibody-β2-microglobulin/CD1d complex. Different S2 cells are cotransfected with plasmids encoding CD1d (I.E), β2-microglobulin (I.F) and pCOBLAST (Invitrogen). pCOBLAST confers resistance to Blasticidin. Stable clones are selected using Blasticidin. Expression of the recombinant CD1d-β2-microglobulin complex is induced in the cells by the addition of copper sulfate or cadmium chloride, and the cell supernatants screened by ELISA using antibodies specific for B2M, and CD1d. The clones that express the highest amount of CD1d-β2-microglobulin complex are expanded and used to produce quantities of this molecule.

C. Purification. The highest expressing clone from (A) and (B) of Example 9 is expanded to 10+ L scale cultures in serum free X-press serum free media, and induced to express the recombinant molecules by the addition of copper sulfate or cadmium chloride to the media. For both the antibody-avidin and CD1d-B2M molecules, the complex containing media is concentrated and dialyzed against 0.15M sodium phosphate buffer (pH 7.4). The antibody-avidin and CD1d-B2M complexes are purified by Ni-NTA agarose chromatography, and then further purified by HPLC. BirA enzymatic biotinylation of CD1d is carried out according to the manufacturers protocol (Avidity, Inc). The remaining free biotin is removed by dialysis into phosphate buffered saline, pH 7.4. The biotinylated CD1d/B2M complex is incubated with a 3 fold molar excess of α-GalCer (CD1d ligand) overnight at room temperatue. Excess α-GalCer is removed by dialysis. The CD1d/B2M/α-GalCer complex is incubated with the antibody-avidin molecule for 4 hours at room temperature. Assembled complex is purified by HPLC.

Example 10

Construction of IgG-B2M Fusion Protein Complexed with Soluble CD1d

An antibody fusion molecule is formed that contains all (IgG-B2M), or a portion (F(ab)-B2M and F(ab')2-B2M) of an antibody molecule fused in frame with the β2-microglobulin open reading frame. Assembly takes place in a three-step process. In step one, PCR is used to create the cloning cassette for VH, including the appropriate regions preceded by a signal sequence (SS) for secretion and followed by a linker with an embedded KpnI restriction site. In step two, PCR is used to amplify the β2-microglobulin gene. Finally, in step three, restriction digestion at the KpnI site followed by ligation is used to combine the two fragments. The IgG1 and β2-microglobulin proteins are separated by a 12 amino acid linker.

The chimeric Heavy Chain along with the complementing Ig Light Chain is produced in *Drosophila* cells along with the extracellular portion of CD1d. This trimeric complex is purified.

1. Construction of IgG1/VH cassette. Standard PCR is used to amplify the appropriate regions of IgG1 with a pre-configured VH insertion site from a previously described template. The PCR product is gel purified according to standard procedure. Specifically, an IgG1 construct that allows for insertion of a variable gene of interest through BssHI and BstEII restriction sites is used. This construct is described elsewhere (U.S. Appl. Publ. No. 2003/0104402, published Jun. 5, 2003) and is available as template for PCR using the following primers.

For the F(ab) construct: (7) Sense 5' AATTGCGGCCG-CAAA CCATGGGATGGAGCTGTATCATC 3' (SEQ ID NO:23) (NotI and NcoI sites in bold); and (8) Anti-sense 5' CGGGGTACCTGACCCACCGCCTCCTTT-CTTGTCCACCTTGGTGTT 3' (SEQ ID NO:24) (linker is in bold; KpnI site is bolded and underlined). For the F(ab') 2 construct: (7) Sense 5' AATTGCGGCCGCAAACCATGG GATGGAGCTGTATCATC 3' (SEQ ID NO:25) (NotI and NcoI sites in bold); and (8) Anti-sense 5' CGG GGTACCTGACCCACCGCCTCC TGGGCACG-GTGGGCATGTGTG 3' (SEQ ID NO:26) (linker is in bold; KpnI site is bolded and underlined).

For the full length IGg1 construct: (7) Sense 5' AATT-GCGGCCGC AAACCATGGGATGGAGCTGTATCATC 3' (SEQ ID NO:27) (NotI and NcoI sites in bold); and (8) Anti-sense 5' CGGGGTACC TGACCCACCGCCTCCTT-TACCCGGAGACAGGGAGAG 3' (SEQ ID NO:28) (linker is in bold; KpnI site is bolded and underlined).

In other embodiments, the CH1 region derives from other immunoglobulin isotypes, including IgG2, IgG3, IgG4, IgA, IgM, IgD or IgE. Particularly preferred is the longer and more flexible IgG3 hinge region.

2. Construction of β2-microglobulin. The fragment is generated by standard PCR using plasmid DNA as template and the following primers: (1) Sense 5' CGG GGTACCGGAGGCGGTGGGTCA ATCCAGCG-TACTCCA 3' (SEQ ID NO: 29) (linker is in bold; KpnI restriction site is bolded and underlined); and (14) Anti-sense 5'-CGACCGGTCATGTCTCGATCCCACTT-3' (SEQ ID NO:30) (AgeI restriction site is in bold). The PCR product is gel purified according to standard procedure.

3. Assembled Chimeric IgG1-β2-microglobulin product. The above fragments "1" and "2" are joined by restriction digestion at the KpnI site followed by ligation employing standard protocols. The complete gene is designed for insertion in frame with a C terminal 6-His tag into the Drosophila expression vector pMT/V5-His (Invitrogen). This strategy is not limited to the use of this vector or a drosophila expression system. Specifically, the use of other expression vectors simply requires re-engineering of the restriction digestion sites flanking the complete construct (NotI and AgeI). The nucleotide and protein sequence below are presented without an inserted VH-gene. Any given VH-gene can be inserted between the BssHII (bold) and BstEII (dashed underline) sites.

The nucleotide sequence of the chimeric F(ab)-β2 microglobulin is: GCGGCCGCAAACC ATGGGATGGAGCTGTATCATCCTCTTCTTGGTA-GCAACAGCTACAGGCGCGCATAT GGTCACCGTCTCCTCAGCCTCC ACCAAGGGC-CCATCGGTCTTCCCCCTGGACACCCTCCTC-CAAGAGCA CCTCTGGGGGCACAGCGGC-CCTGGGCTGCCTGGTCAAGGACTACTT CCCCGAACCGGTGACGGTGTCGTGGAACTCAG-GCGCCCTGACCAGC GGCGTGCACACCTTCCCG-GCTGTCCTACAGTCCTCAGGACTCTACT CCCTCA-GCAGCGTCGTGACCGTGCCCTCCAGCAGCTTG-GGCACCCA GACCTACATCTGCAACGTGAATCA-CAAGCCCAGCAACACCAAGGT GGACAAGAAA GGAGGCGGTGGGTCAGGTACCGGAGGCGGTG-GGTCAATCCAGCGTACTCCAAAGATTCAGGTTT-ACTCACGTCATCCA GCAGAGAATGGAAAGT-CAAATTTCCTGAATTGCTATGTGTCTGGGT TTCATC-CATCCGACATTGAAGTTGACTTACTGAAGAATGGA-GAGAG AATTGAAAAAGTGGAGCATTCAGACTTGTCTTTCA-GCAAGGACTGG TCTTTCTATCTCTTGTACTACACT-GAATTCACCCCCACTGAAAAAGA TGAGTATGCCT-GCCGTGTGAACCATGTGACTTTGTCACAGCCCAAG ATAGTTAAGTGGGATCGAGACATG ACCGGTCATCATCACCATCACCATTGA-780 (SEQ ID NO:31) (double underline: NotI restriction site; single underline: Signal sequence; bold: BssHII restriction site; dashed underline: BstEII restriction site; bold and underlined: linker; wavy underline: AgeI restriction site; italics and underlined: His Tag).

The nucleotide sequence of the chimeric F(ab)-β2 microglobulin is: MGWSCIILFLVATATGAHMVTVSSASTK-GPSVFPLAPSSKSTSGGTAA LGCLVKDYFPEPVT-VSWNSGALTSGVHTFPAVLQSSGLYSLSSVVTVP SSSLGTQTYICNVNHKPSNTKVDKK GGGGSGTGGGGSIQRTPKIQVY SRHPAENGKSNFLN-CYVSGFHPSDIEVDLLKNGERIEKVEHSDLVFSKD WSFYLLYYTEFTPTEKDEYACRVNHVTLSQPKIVKW-DRDMTGHHHHHH (SEQ ID NO:32). The variable gene sequence is introduced at the upstream histidine in bold and the rest of the bolded amino acids are removed upon insertion of the variable gene sequence. The linker is bolded and underlined.

The nucleotide sequence of the chimeric F(ab')2-β2-microglobulin is: GCGGCCGCAAACC ATGGGATGGAGCTGTATCATCCTCTTCTTGG-TAGCAACAGCTACAGGCGCGCATAT GGTCACCGTCTCCTCAGCCTCC ACCAAGGGC-CCATCGGTCTTCCCCCTGGCACCCTCCTC-CAAGAGCA CCTCTGGGGGCACAGCGGC-CCTGGGCTGCCTGGTCAAGGACTACTT CCCCGAACCGGTGACGGTGTCGTGGAACTCAG-GCGCCCTGACCAGC GGCGTGCACACCTTCCCG-GCTGTCCTACAGTCCTCAGGACTCTACT CCCTCA-GCAGCGTCGTGACCGTGCCCTCCAGCAGCTTGG-GCACCCA GACCTACATCTGCAACGTGAATCA-CAAGCCCAGCAACACCAAGGT GGACAAGAAAGT-TGAGCCCAAATCTTGTGACAAAACTCACACATG CCCACCGTGCCCAGGAGGCGGTGGG-TCAGGTACCGGAGGCGGTGGGTCAATCCAGCGT-ACTCCAAAGATTCAGGTTTACTCACGTCATC CAGCAGAGAATGGAAAGTCAAATTTCCTGAATT-GCTATGTGTCTGGG GTTTCATCCATCCGACATT-GAAGTTGACTTACTGAAGAATGGAGAG AGAATT-GAAAAAGTGGAGCATTCAGACTTGTCTTTCAGCA-AGGACT GGTCTTTCTATCTCTTGTACTACACTGAAT-TCACCCCCACTGAAAAA GATGAGTATGCCTGCCGT-GTGAACCATGTGACTTTGTCACAGCCCA AGATAGT-TAAGTGGGATCGAGACATG ACCGGTCATCATCACCATCACCATTGA (SEQ ID NO:33) (double underline: NotI restriction site; single underline: signal sequence; bold: BssHII restriction site; dashed underline: BstEII restriction site; bold and underlined: linker; wavy underline: AgeI restriction site; italics and underlined: His Tag).

The polypeptide sequence of the chimeric F(ab')2-β2-microglobulin is: MGWSCIILFLVATATGAHMVTVSSAS-TKGPSVFPLAPSSKSTSGGTAA LGCLVKDYFPEPVT-VSWNSGALTSGVHTFPAVLQSSGLYSLSSVVTVP SSSLGTQTYICNVNHKPSNTKVDKKVEPKSCDKTH-TCPPCPGGGGSGTGGGGSIQRTPKIQVYSRHP-AENGKSNFLNCYVSGFHPSDIEVDLLKN GERIEK-VEHSDLVFSKDWSFYLLYYTEFTPTEKDEYACRVN-HVTLSQP KIVKWDRDMTGHHHHHH (SEQ ID NO:34). The variable gene sequence is introduced at the histidine in bold and the rest of the bolded amino acids are removed upon insertion of the variable gene sequence. The linker is bolded and underlined.

The nucleotide sequence of the chimeric full IgG1-β2 microglobulin is: GCGGCCGCAAACC ATGGGATGGAGCTGTATCATCCTCTTCTTGGT-AGCAACAGCTACAGGCGCGCATAT GGTCACCGTCTCCTCAGCC TCCACCAAGGGC-CCATCGGTCTTCCCCCTGGCACCCTCCTCCAAGA GCAACCTCTGGGGGCACAGCGGCCCTGGGCTGC-CTGGTCAAGGACTA CTTCCCCGAACCGGTGACG-GTGTCGTGGAACTCAGGCGCCCTGACC AGCG-GCGTGCACACCTTCCCGGCTGTCCTACAGTCCTC-AGGACTCT ACTCCCTCAGCAGCGTCGTGACCGT-GCCCTCCAGCAGCTTGGGCAC CCAGACCTA-CATCTGCAACGTGAATCACAAGCCCAGCAACAC-CAA GGTGGACAAGAAAGTTGAGCCCAAATCTTGT-GACAAAACTCACAC ATGCCCACCGTGCCCAGCAC-CTGAACTCCTGGGGGGACCGTCAGTC TTCCTCT-TCCCCCCAAAACCCAAGGACACCCTCATGATCT-CCCGGA CCCCTGAGGTCACATGCGTGGTGTG-GACGTGAGCCACGAAGACC CTGAGGTCAAGT-TCAACTGGTACGTGGACGGCGTGGAGGTGCATA ATGCCAAGACAAAGCCGCGGGAGGAGCAGTA-CAACAGCACGTACC GTGTGGTCAGCGTCCTCAC-CGTCCTGCACCAGGACTGGCTGAATGG CAAGGAG-TACAAGTGCAAGGTCTCCAACAAAGCCCTCCCA-GCCCC CATCGAGAAACCATCTCCAAAGC-CAAAGGGCAGCCCCGAGAACC ACAGGTGTACAC-CCTGCCCCCATCCCGGGATGAGCTGACCAAGAAC CAGGTCAGCCTGACCTGCCTGGTCAAAGGCTTC-TATCCCAGCGACA TCGCCGTGGAGTGGGAGAG-CAATGGGCAGCCGGAGAACAACTACA AGAC- CACGCCTCCCGTGCTGGACTCCGACGGCTCCTTC-
TTCCTCTAC AGCAAGCTCACCGTGGACAAGAGCA-
GGTGGCAGCAGGGGAACGTC TTCTCATGCTCCGT-
GATGCATGAGGCTCTGCACAACCACTACACGC
AGAAGAGCCTCTCCCTGTCTCCGGGTAAA
GGAGGCGGTGGGTCAGGTACCGGAGGCGGT-
GGGTCAATCCAGCGTACTCCAAAGATTCA GGTT-
TACTCACGTCATCCAGCAGAGAATGGAAAGT-
CAAATTTCCTG AATTGCTATGTGTCTGGGTTTCATC-
CATCCGACATTGAAGTTGACTT
ACTGAAGAATGGAGAGAGAATTGAAAAAGTG-
GAGCATTCAGACTT GTCTTTCAGCAAGGACTG-
GTCTTTCTATCTCTTGTACTACACTGAAT TCAC-
CCCCACTGAAAAAGATGAGTATGCCTGCCGTGT-
GAACCATGT GACTTTGTCACAGCCCAAGATAGT-
TAAGTGGGATCGAGACATG
ACCGGTCATCATCACCATCACCATTGA (SEQ ID
NO:35) (double underline: NotI restriction site; single
underline: Signal sequence; bold: BssHII restriction site;
dashed underline: BstEII restriction site; bold and under-
lined: linker; wavy underline: AgeI restriction site; and
italics and underlined: His Tag).

The polypeptide sequence of the chimeric full IgG1-β2
microglobulin is: MGWSCIILFLVATATGAHMVTVSSAS-
TKGPSVFPLAPSSKSTSGG TAALGCLVKDYFPEPVT-
VSWNSGALTSGVHTFPAVLQSSGLYSLSSVV TVPSSS-
LGTQTYICNVNHKPSNTKVDKKVEPKSCDKTHTC-
PPCPAPELL GGPSVFLFPPKPKDTLMISRTPEVTCV-
VVDVSHEDPEVKFNWYVDGVE VHNAKTKPRE-
EQYNSTYRWSVLTVLHQDWLNGKEYKCKVSNKALP
APIEKTISKAKGQPREPQVYTLPPSRDELTKNQVSLT-
CLVKGFYPSDIA VEWESNGQPENNYKTTPPVIDS-
DGSFFLYSKLTVDKSRWQQGNVFSC SVMHEALHN-
HYTQKSLSLSPGK
GGGGSGTGGGGSIQRTPKIQVYSRH PAENGKSNFLN-
CYVSGFHPSDIEVDLLKNGERIEKVEHSDLVFSKDWS
FYLLYYTEFTPTEKDEYACRVNHVTLSQPKIVKW-
DRDMTTGHHHHHH (SEQ ID NO:36). The variable gene
sequence is introduced at the histidine in bold and the rest of
the bolded amino acids are removed upon insertion of the
variable gene sequence. The linker is bolded and underlined.

Example 11

Chimeric Kappa L Chain-β2 Microglobulin

Employing the same strategy described above for fusion
products with immunoglobulin heavy chain or heavy chain
fragments, a chimeric kappa L chain is coupled in frame
with β2-microglobulin. Assembly takes place in a three-step
process. In step one, PCR is employed to create the CL
region preceded by a signal sequence for secretion and
followed by a linker with an embedded KpnI restriction site.
The kappa light chain constant region (CK) is PCR ampli-
fied from a previously described plasmid template with a
pre-configured VL insertion site that allows for directional
cloning of any immunoglobulin light chain variable region
gene of interest at ApaLI and XhoI restriction (U.S. Appl.
Publ. No. 2003/0104402, published Jun. 5, 2003). In step
two, the β2-microglobulin gene preceded by the linker with
a KpnI restriction site is amplified exactly as described
above for heavy chain fusion products. Finally, in step three,
the two fragments are joined by restriction digestion at the
KpnI site followed by ligation employing standard proto-
cols. The modifications of primer sequences required for
amplification of the immunoglobulin light chain with either
kappa or lambda light chain constant regions will be appar-
ent to those skilled in the art.

Example 12

N Terminal Fusion Proteins

Employing strategies similar to those described above,
chimeric molecules are constructed where β2 microglobulin
is fused in frame with the amino terminus of the immuno-
globulin heavy or light chain. These molecules are
assembled in a 3 step process. In step 1, the β2 microglobu-
lin gene, including the signal sequence, is PCR amplified
from a plasmid template. This PCR modification adds a NotI
site at the 5' end, and a portion of the gly, ser linker and a
KPNI site at the 3' end. In step 2, the entire immunoglobulin
heavy chain or light chain genes (variable and constant
domains, or constant domain with restriction endonuclease
sites for the insertion of a V gene), without the signal
sequence, is PCR amplified. This PCR modification adds a
portion of the gly,ser linker and a KpnI site at the 5' end, and
an AgeI site at the 3' end. Finally, in step three, the two
fragments are joined by restriction digestion at the KpnI site
followed by ligation employing standard protocols. The
modifications of primer sequences required for amplification
of these genes and the construction of these molecules will
be apparent to those skilled in the art.

Example 13

Construction of Extracellular Domain of CD1d.
cDNA Isolated from Human Bone Marrow or
Spleen is Used as a Source of CD1d mRNA The extracellular domain of CD1d is PCR amplified using
the primers: (E1 sense): CAC
GGTACCGATATGGGGTGCCTGCTGTTTCTGC (SEQ D
NO:37) (KPNI site is underlined) and (E1 antisense): CAG
ACCGGTCCAGTAGAGGACGATGTCCTG (SEQ ID
NO:38) (Age I site is underlined).

The CD1d extracellular product is digested with Kpn I
and Age I and cloned into the KpnI and AgeI sites of
pMT/V5-His A vector (Invitrogen). The C terminus of CD1d
is in frame with a 6 His tag encoded by the vector, and
contains an additional Thr and gly that are encoded by the
AgeI site. The resulting sequence is:
GGTACCGATATGGGGTGCCTGCTGTTTCTG
CTGCTCTGGGCGCTCCTCCAGGCT-
TGGGGAAGCGCTGAAGTCCCGC AAAGGCTTTTC-
CCCCTCCGCTGCCTCCAGATCTCGTCCTTCGCCAAT
AGCAGCTGGACGCGCACCGACGGCTTGGCGTG-
GCTGGGGGAGCTG CAGACGCACAGCTGGAG-
CAACGACTCGGACACCGTCCGCTCTCTGA AGCCT-
TGGTCCCAGGGCACGTTCAGCGACCAGCAGTGG-
GAGACGC TGCAGCATATATTTCGGGTTTATC-
GAAGCAGCTTCACCAGGGACGT GAAGGAATTCGC-
CAAAATGCTACGCTTATCCTATCCCTTGGAGCTC
CAGGTGTCCGCTGGCTGTGAGGTGCAC-
CCTGGGAACGCCTCAAATA ACTTCTTCCATGTAG-
CATTTCAAGGAAAAGATATCCTGAGTTTCCA
AGGAACTTCTTGGGAGCCAACCCAAGAGGC-
CCCACTTTGGGTAAAC TTGGCCATTCAAGTGCT-
CAACCAGGACAAGTGGACGAGGGAAACA GTGCA-
GTGGCTCCTTAATGGCACCTGCCCCCAATTTGTC-
AGTGGCC TCCTTGAGTCAGGGAAGTCGGAACT-
GAAGAAGCAAGTGAAGCCCA AGGCCTGGCTGTC-
CCGTGGCCCCAGTCCTGGCCCTGGCCGTCTGCT GCTGGTGTGCCATGTCTCAGGATTCTACCCAAAGC-
CTGTATGGGTG AAGTGGATGCGGGGTGAGCAG-
GAGCAGCAGGGCACTCAGCCAGGG GACATCCT-
GCCCAATGCTGACGAGACATGGTATCTCCGAGCA-
ACCC TGGATGTGGTGGCTGGGGAGGCAGCTGGC-
CTGTCCTGTCGGGTGAA GCACAGCAGTCTA-
GAGGGCCAGGACATCGTCCTCTACTGG
ACCGGTCATCATCACCATCACCATTGA (SEQ ID NO:39).

The translated polypeptide sequence is: MGCLLFLLL-
WALLQAWGS AEVPQRLFPLRCLQISSFANSSWTRT-
DGLAWLGELQTHSWSNDSDTVR SLKPWSQGTF-
SDQQWETLQHIFRVYRSSFTRDVKEFAKMLRLSYPLEL
QVSAGCEVHPGNASNNFFHVAFQGKDILS-
FQGTSWEPTQEAPLWVNL AIQVLNQDKWTRET-
VQWLLNGTCPQFVSGLLESGKSELKKQVKPKA
WLSRGPSPGPGRLLLVCHVSGFYPKPVWVKWM-
RGEQEQQGTQPGDIL PNADETWYLRATLDV-
VAGEAAGLSCRVKHSSLEGQDIVLYWTGHHH HHH
(SEQ ID NO:40).

Example 14

Production and Purification of the Chimeric
Antibody-β2-Microglobulin CD1d Complex Production of the antibody-β2-microglobulin/CD1d complex is done in 2 steps. In the first step, *Drosophila* S2 cells are transfected with the constructs encoding the chimeric antibody-b2M and the antibody light chain gene. High expressing clones are selected and then transfected with the CD1d construct and clones expressing high levels of the antibody-β2-microglobulin/CD1d complex are isolated.

A. Generation of *Drosophila* S2 cells stably transfected and producing antibody-β2-microglobulin. *Drosophila* S2 cells are triply transfected with plasmids that encode 1) antibody-B2M (full IgG, F(ab), or F(ab')2); 2) antibody light chain; and 3) pCOHYGRO (Invitrogen). This plasmid confers resistance to the drug hygromycin. The triply transfected cells are selected with hygromycin and clones isolated. Expression of the recombinant antibody-b2M are induced in the cells by the addition of copper sulfate or cadmium chloride, and the cell supernatants screened by ELISA using antibodies specific for antibody and B2M.

B. Production of the chimeric antibody-β2-microglobulin/CD1d complex. The highest antibody-B2M producing clones from (A) is cotransfected with plasmids encoding CD1d (I.E) and pCOBLAST (Invitrogen). pCOBLAST confers resistance to Blasticidin. Stable clones are selected using Hygromycin and Blasticidin. Expression of the recombinant antibody-b2M/CD1d complex is induced in the cells by the addition of copper sulfate or cadmium chloride, and the cell supernatants screened by ELISA using antibodies specific for Ig, B2M, and CD1d. The clones that express the highest amount of antibody-b2M/CD1d complex are expanded and used to produce quantities of this molecule.

C. Purification. The highest expressing clone from (B) is expanded to 10+ L scale cultures in serum free X-press media, and induced to express this complex by the addition of copper sulfate or cadmium chloride to the media. The complex containing media is concentrated and dialyzed against 0.15M sodium phosphate buffer (pH 7.4). The antibody-b2M/CD1d complex is purified by Ni-NTA agarose chromatography, and then further purified by HPLC. The purified complex is then incubated with a 3 fold molar excess of α-GalCer (CD1d ligand) overnight at room temperature. Excess α-GalCer is removed by dialysis.

Example 15

Construction of IgG-CD1d Fusion Protein

An antibody fusion molecule is formed that contains all (IgG-CD1d), or a portion (F(ab)-CD1d and F(ab')2-CD1d) of an antibody molecule fused in frame with the extracellular domain of CD1d. Assembly takes place in a three-step process. In step one, PCR is used to create the cloning cassette for VH, including the appropriate IgG1 regions preceded by a signal sequence (SS) for secretion and followed by a linker with an embedded KpnI restriction site. In step two, PCR is used to amplify the extracellular region of the CD1d gene. Finally, in step three, restriction digestion at the KpnI site followed by ligation is used to combine the two fragments. The IgG1 and CD1d proteins are separated by a 12 amino acid linker.

The chimeric heavy chain along with the complementing Ig Light Chain is produced in *Drosophila cells along with human* β2-microglobulin. This trimeric complex is purifed.

1. Construction of VH cassette. Standard PCR is used to amplify the appropriate portion of IgG1 with a pre-configured VH insertion site from a previously described template which is a human IgG1 construct that allows for insertion of a variable gene of interest through BssHI and BstEII restriction sites. The PCR product is gel purified according to standard procedure. This construct is described elsewhere (U.S. Appl. Publ. No. 2003/0104402, published Jun. 5, 2003) and is available as template for PCR using the following primers.

For the F(ab) fragment: (7) Sense 5' AATTGCGGCCG-CAAA CCATGGGATGGAGCTGTATCATC 3' (SEQ ID NO:41) (NotI and NcoI sites in bold); and (8) Anti-sense 5' CGG<u>GGTACC</u>TGACCCACCGCCTCCTTTCTTGT-CCACCTTGGTGTT 3' (SEQ ID NO:42) (linker is in bold; KpnI site is bolded and underlined).

For the F(ab')2 fragment: (7) Sense 5' AATTGCGGCCG-CAAACCATGGG ATGGAGCTGTATCATC 3' (SEQ ID NO:43) (NotI and NcoI sites in bold); and (8) Anti-sense 5' CGG<u>GGTACC</u>TGACCCACCGCCTCCTGGGCACGG-TGGGCATGTGT G 3' (SEQ ID NO:44) (linker is in bold; KpnI site is bolded and underlined).

For the full IgG1: (7) Sense 5' AATTGCGGCCG-CAAACCATGG GATGGAGCTGTATCATC 3' (SEQ ID NO:45) (NotI and NcoI sites in bold); and (8) Anti-sense 5' CGG<u>GGTACC</u>TGACCCACCGCCTCC TTTACCCGGA-GACAGGGAGAG 3' (SEQ ID NO:46) (linker is in bold; KpnI site is bolded and underlined).

In other embodiments, the antibody regions derive from other immunoglobulin isotypes, including IgG2, IgG3, IgG4, IgA, IgM, IgD or IgE. Particularly preferred is the longer and more flexible IgG3 hinge region.

2. Construction of extracellular CD1d. The fragment is generated by standard PCR using plasmid DNA as template and the following primers: (1) Sense 5' CGG <u>GGTACC</u>GGAGGCGGTGGGTCA GTCCCGCAAAGGC=TTTC 3' (SEQ ID NO:47) (linker is in bold; KpnI restriction site is bolded and underlined); and (14) Anti-sense 5'-CG <u>ACCGGT</u>CCAGTAGAGGACGATGTCCTG-3' (SEQ ID NO:48) (AgeI restriction site is in bold). The PCR product is gel purified according to standard procedure.

3. Assembled chimeric antibody-CD1d product. The above fragments "1" and "2" are joined by restriction digestion at the KpnI site followed by ligation employing standard protocols. The complete gene is designed for insertion in frame with a C terminal 6-His tag into the *Drosophila* expression vector pMT/V5-His (Invitrogen). This strategy is not limited to the use of this vector or a *drosophila* expression system. Specifically, the use of other expression vectors simply requires re-engineering of the restriction digestion sites flanking the complete construct (NotI and AgeI). The nucleotide and protein sequences below are presented without an inserted VH-gene. Any given VH-gene can be inserted between the BssHII (bold) and BstEII (dashed underline) sites.

The final nucleotide sequence of the chimeric F(ab)-CD1d product is: GCGGCCGCAAACC ATGGGATGGAGCTGTATCATCCTCTTCTTGGTA GCAACAGCTACAGGCGCGCATAT GGTCACCGTCTCCTCAGCCTCC ACCAAGGGC CCATCGGTCTTCCCCCTGGCACCCTCCTC CAAGAGCA CCTCTGGGGGCACAGCGGC CCTGGGCTGCCTGGTCAAGGACTACTT CCCCGAACCGGTGACGGTGTCGTGGAACTCAG GCGCCCTGACCAGC GGCGTGCACACCTTCCCG GCTGTCCTACAGTCCTCAGGACTCTACT CCCTCA GCAGCGTCGTGACCGTGCCCTCCAGCAGCTTGG GCACCCA GACCTACATCTGCAACGTGAATCA CAAGCCCAGCAACACCAAGGT GGACAAGAAA GGAGGCGGTGGGTCAGGTACCGGAGGCGG TGGGTCAGTCCCGCAAAGGCTTTTCCCCCTCCG CTGCCTCCAGATCTCG TCCTTCGCCAATAGCA GCTGGACGCGCACCGACGGCTTGGCGTGGC TGGGGGAGCTGCAGACGCACAGCTGGAGCAAC GACTCGGACACCG TCCGCTCTCTGAAGCCTTG GTCCCAGGGCACGTTCAGCGACCAGCA GTGGGA GACGCTGCAGCATATATTTCGGGTTTATCGAAGC AGCTTC ACCAGGGACGTGAAGGAATTCGC CAAAATGCTACGCTTATCCTATC CCTTGGAGCTC CAGGTGTCCGCTGGCTGTGAGGTGCACCCTGGGAA CGCCTCAAATAACTTCTTCCATGTAG CATTTCAAGGAAAAGATATC CTGAGTTTC CAAGGAACTTCTTGGGAGCCAACCCAAGAGGC CCCAC TTTGGGTAAACTTGGCCATTCAAGTGCTCAACCAG GACAAGTGGAC GAGGGAAACAGTGCAGTGGCTC CTTAATGGCACCTGCCCCCAATTT GTCAGTGGC CTCCTTGAGTCAGGGAAGTCGGAACTGAAGAAGCAA GTGAAGCCCAAGGCCTGGCTGTCCCGTGGCCCCA GTCCTGGCCCTG GCCGTCTGCTGCTGGTGTGCCAT GTCTCAGGATTCTACCCAAAGCC TGTATGGGT GAAGTGGATGCGGGGTGAGCAGGAGCAGCAGG GCAC TCAGCCAGGGGACATCCTGCCCAATGCT GACGAGACATGGTATCTC CGAGCAACCCTGGAT GTGGTGGCTGGGGAGGCAGCTGGCCTGTCCT GTCGGGTGAAGCACAGCAGTCTAGAGGGCCAGGA CATCGTCCTCT ACTGG ACCGGTCATCATCACCATCACCATTGA (SEQ ID NO:49) (double underline: NotI restriction site; single underline: Signal sequence; bold: BssHII restriction site; dashed underline: BstEII restriction site; bold and underlined: linker, wavy underline: AgeI restriction site; italics and underlined: His Tag).

The final polypeptide sequence of the chimeric F(ab)-CD1d product is: MGWSCIILFLVATATGAHMVTVSSAS TKGPSVFPLAPSSKSTSGGTAA LGCLVKDYFPEPVT VSWNSGALTSGVHTFPAVLQSSGLYSLSSVVTVP SSSLGTQTYICNVNHKPSNTKVDKK GGGGSGTGGGGSVPQRLFPLRC LQISSFANSSWTRT DGLAWLGELQTHSWSNDSDTVRSLKPWSQGTFS DQQWETLQHIFRVYRSSFTRDVKEFAKMLRLSY PLELQVSAGCEVHP GNASNNFFHVAFQGKDILS FQGTSWEPTQEAPLWVNLAIQVLNQDKW TRET VQWLLNGTCPQFVSGLLESGKSELKKQVKPKAW LSRGPSPGPG RLLLVCHVSGFYPKPVWVKWM RGEQEQQGTQPGDILPNADETWYLR ATLDV VAGEAAGLSCRVKHSSLEGQDIVLYWTGHHHHH (SEQ ID NO:50). The variable gene sequence is introduced at the upstream histidine in bold and the rest of the bolded amino acids are removed upon insertion of the variable gene sequence. The linker is bolded and underlined.

The final nucleotide sequence of the chimeric F(ab')2-CD1d product is: GCGGCCGCAAA CCATGGGATGGAGCTGTATCATCCTCTTCTTGGT AGCAACAGCTACAGGCGCGCATATGGTCACCGT CTCCTCAGCCT CCACCAAGGGCCCATCGGTCTTC CCCCTGGCACCCTCCTCCAAGAG CAC CTCTGGGGGCACAGCGGCCCTGGGCTGCCTGGT CAAGGACTAC TTCCCCGAACCGGTGACGGTGTCGTGGAACTCAG GCGCCCTGACCA GCGGCGTGCACACCTTCCCG GCTGTCCTACAGTCCTCAGGACTCTA CTCCCTCA GCAGCGTCGTGACCGTGCCCTCCAGCAGCTTGGG CACC CAGACCTACATCTGCAACGTGAATCA CAAGCCCAGCAACACCAAG GTGGACAAGAAAGT TGAGCCCAAATCTTGTGACAAAACTCACACA TGC CCACCGTGCCCAGGAGGCGGTGGGTC AGGTACCGGAGGCGGTGGGTCAGTCCCGCAA AGGCTTTTCCCCCTCCGCTGCCTCCAGAT CTCGTC CTTCGCCAATAGCAGCTGGACGCGCACCGACG GCTTGGCG TGGCTGGGGGAGCTGCAGACGCACA GCTGGAGCAACGACTCGGAC ACCGTCCGCTCTCTGAAGCCTTGGTCCCA GGGCACGTTCAGCGACC AGCAGTGGGAGACGCT GCAGCATATATTTCGGGTTTATCGAAGCAG CTTCACCAGGGACGTGAAGGAATTCGCCAAAAT GCTACGCTTATCC TATCCCTTGGAGCTCCAGGT GTCCGCTGGCTGTGAGGTGCACCCTG GGAACGC CTCAAATAACTTCTTCCATGTAGCATTTCAAG GAAAAGA TATCCTGAGTTTCCAAGGAACTTCT TGGGAGCCAACCCAAGAGGCC CCACTTTGGG TAAACTTGGCCATTCAAGTGCTCAACCAGGA CAAGT GGACGAGGGAAAC AGTGCAGTGGCTCCTTAATGGCACCTGCCCCC AATTTGTCAGTGGCCTCCTTGAGTCAGGGAAGTCG GAACTGAAGAA GCAAGTGAAGCCCAAGGCCTG GCTGTCCCGTGGCCCCAGTCCTGGC CCTGGC CGTCTGCTGCTGGTGTGCCATGTCTCAGGATTCT ACCCAA AGCCTGTATGGGTGAAGTGGAT GCGGGGTGAGCAGGAGCAGCAGG GCACTCAGC CAGGGGACATCCTGCCCAATGCTGACGAGA CATGGT ATCTCCGAGCAACCCTGGATGTGGTG GCTGGGGAGGCAGCTGGCCT GTCCTGTCGGGT GAAGCACAGCAGTCTAGAGGGCCAGGACATCGT CCTCTACTGG ACCGGTCATCATCACCATCACCATTGA (SEQ ID NO:51) (double underline: NotI restriction site; single underline: Signal sequence; bold: BssHII restriction site; dashed underline: BstEII restriction site; bold and underlined: linker; wavy underline: AgeI restriction site; and italics and underlined: 6 His tag).

The final polypeptide sequence of the chimeric F(ab')2-CD1d product is: MGWSCIILFLVATATGA HMVTVSSASTKGPSVFPLAPSSKSTSGG TAALG CLVKDYFPEPVTVSWNSGALTSGVHTFPAVLQSS GLYSLSSVV TVPSSSLGTQTYICNVNHKPSNTKVDK-KVEPKSCDKTHTCPPCP GGGGSGTGGGSVPQRLFPLRCLQISSFANSSWTRT-DGLAWLGELQTHSWS NDSDTVRSLKPWSQGTF-SDQQWETLQHIFRVYRSSFTRDVKEFAKML RLSY-PLELQVSAGCEVHPGNASNNFFHVAFQGKDILS-FQGTSWEPTQE APLWVNLAIQVLNQDKWTRET-VQWLLNGTCPQFVSGLLESGKSELKK QVKP-KAWLSRGPSPGPGRLLLVCHVSGFYPKPVWVKWM-RGEQEQQG TWPGDILPNADETWYLRATLDV-VAGEAAGLSCRVKHSSLEGQDIVLY WT<u>GHHHHHH</u> (SEQ ID NO:52). The variable gene sequence is introduced at the upstream histidine in bold and the rest of the bolded amino acids are removed upon insertion of the variable gene sequence. The linker is bolded and underlined.

The final nucleotide sequence of the chimeric IgG1-CD1d product is: <u>GCGGCCGC</u>AAACC ATGGGATGGAGCTGTATCATCCTCTTCTTGGTA-GCAACAGCTACAGGCGCGCATAT <u>GGTCACC</u>GTCTCCTCAGCCTCC ACCAAGGGC-CCATCGGTCTTCCCCCTGGCACCCTCCTC-CAAGAGCA CCTCTGGGGGCACAGCGGC-CCTGGGCTGCCTGGTCAAGGACTACTT CCCCGAACCGGTGACGGTGTCGTGGAACTCAG-GCGCCCTGACCAGC GGCGTGCACACCTTCCCG-GCTGTCCTACAGTCCTCAGGACTCTACT CCCTCA-GCAGCGTCGTGACCGTGCCCTCCAGCAGCTTGGG-CACCCA GACCTACATCTGCAACGTGAATCA-CAAGCCCAGCAACACCAAGGT GGACAAGAAAGT-TGAGCCCAAATCTTGTGACAAAACTCACACATG CCCACCGTGCCCAGCACCTGAACTC-CTGGGGGGACCGTCAGTCTTC CTCTTC-CCCCCAAAACCCAAGGACACCCTCATGATCTCCCG-GACCC CTGAGGTCACATGCGTGGTGGTGGACGTGAGC-CACGAAGACCCTG AGGTCAAGTTCAACTGG-TACGTGGACGGCGTGGAGGTGCATAATG CCAAGA-CAAAGCCGCGGGAGGAGCAGTACAACAGCAC-GTACCGTG TGGTCAGCGTCCTCACCGTCCTGCAC-CAGGACTGGCTGAATGGCAA GGAGTACAAGTG-CAAGGTCTCCAACAAAGCCCTCCCAGCCCCCATC GAGAAAACCATCTCCAAAGCCAAAGGGCAGC-CCCGAGAACCACAG GTGTACACCCTGCCCCCATC-CCGGGATGAGCTGACCAAGAACCAGG TCAGCCT-GACCTGCCTGGTCAAAGGCTTCTATCCCAGCGACAT<u>CGC</u> CGTGGAGTGGGAGAGCAATGGGCAGCCGGA-GAACAACTACAAGAC CACGCCTCCCGTGCTG-GACTCCGACGGCTCCTTCTTCCTCTACAGCA AGCT-CACCGTGGACAAGAGCAGGTGGCAGCAGGGGA-ACGTCTTCT CATGCTCCGTGATGCATGAGGCTCTG-CACAACCACTACACGCAGAA GAGCCTCTCCCT-GTCTCCGGGTAAAGGAGGCGGTGGGTCA-<u>GGTACC</u>GGAGGCGGTGGGTCAGTCCCGCAAAG-GCTTTTCCCCCTCCGCT GCCTCCAGATCTCGTCCT-TCGCCAATAGCAGCTGGACGCGCACCGA CGGCT-TGGCGTGGCTGGGGGAGCTGCAGACGCACAGCTG-GAGCAA CGACTCGGACACCGTCCGCTCTCTGAAGCCTTG-GTCCCAGGGCACG TTCAGCGACCAGCAGTGGGA-GACGCTGCAGCATATATTTCGGGTTT ATCGAAGCA-GCTTCACCAGGGACGTGAAGGAATTCGCCAAAATGC TACGCTTATCCTATCCCTTGGAGCTCCAGGTGTC-CGCTGGCTGTGAG GTGCACCCTGGGAACGCCT-CAAATAACTTCTTCCATGTAGCATTTC AAGGAAAAGATATCCTGAGTTTCCAAGGAACTTCT-TGGGAGCCAAC CCAAGAGGCCCCACTTTGGG-TAAACTTGGCCATTCAAGTGCTCAAC CAGGA-CAAGTGGACGAGGGAAACAGTGCAGTGGCTCCT-TAATGGC ACCTGCCCCCAATTTGTCAGTGGCCTC-CTTGAGTCAGGGAAGTCGG AACT-GAAGAAGCAAGTGAAGCCCAAGGCCTGGCTGTC-CCGTGGCC CCAGTCCTGGCCCTGGCCGTCTGCTGCTGGTGTGC-CATGTCTCAGG ATTCTACCCAAAGCCTGTATGGGT-GAAGTGGATGCGGGGTGAGCA GGAGCAGCA-GGGCACTCAGCCAGGGGACATCCTGCCCAAT-GCTGA CGAGACATGGTATCTCCGAGCAACCCTG-GATGTGGTGGCTGGGGA GGCAGCTGGCCTGTCCT-GTCGGGTGAAGCACAGCAGTCTAGAGGG CCAG-GACATCGTCCTCTACTGG <u>ACCGGTCATCATCACCATCACCAT</u>TG A (SEQ ID NO:53) (double underline: NotI restriction site; single underline: Signal sequence; bold: BssHII restriction site; dashed underline: BstEII restriction site; bold and underlined: linker; wavy underline: AgeI restriction site; and italics and underlined: 6-His tag).

The final polypeptide sequence of the IgGlCD1d product is: <u>MGWSCIILFLVATATGA</u>HMVTVS-SASTKGPSVFPLAPSSKSTSGGTAA LGCLVKDYFPEP-VTVSWNSGALTSGVHTFPAVLQSSGLYSLSSVVTVP SSSLGTQTYICNVNHKPSNTKVDKKVEPKSCDKTH-TCPPCPAPELLGG PSVFLFPPKPKDTLMISRTPE-VTCVVVDVSHEDPEVKFNWYVDGVEVH NAKTK-PREEQYNSTYRVVSVLTVLHQDWLNGKEYKC-KVSNKALPAPI EKTISKAK-GQPREPQVYTLPPSRDELTKNQVSLTCLVKGFYPSDI-AVE WESNGQPENNYKTTPPVLDSDGSFFLYSKLT-VDKSRWQQGNVFSCSV MHEALHNHYTQKSLSLSP GKGGGGSGTGGGGSVPQRLFPLRCLQISS FANSS-WTRTDGLAWLGELQTHSWSNDSDTVRSLKP-WSQGTFSDQQW ETLQHIFRVYRSSFTRDVKEFAKM-LRLSYPLELQVSAGCEVHPGNASN NFFHVAFQGKDILSFQGTSWEPTQEAPLWVNLAIQV-LNQDKWTRETV QWLLNGTCPQFVSGLLESGKSELK-KQVKPKAWLSRGPSPGPGLLLV CHVSGFYPK-PVWVKWMRGEQEQQGTQPGDILPNADETWY-LRATLDV VAGEAAGLSCRVKHSSLEGQDIVLYW T<u>GHHHHH</u> (SEQ ID NO:54). The variable gene sequence is introduced at the histidine in bold and the rest of the bolded amino acids are removed upon insertion of the variable gene sequence. The linker is bolded and underlined.

Example 16

Chimeric Lappa L Chain-CD1d

Employing the same strategy described above for fusion products with immunoglobulin heavy chain or heavy chain fragments, a chimeric kappa L chain is coupled in frame with CD1d. Assembly takes place in a three-step process. In step one, PCR is employed to create the CL region preceded by a signal sequence for secretion and followed by a linker with an embedded KpnI restriction site. The kappa light chain constant region (CK) is PCR amplified from a previously described plasmid template with a pre-configured VL insertion site that allows for directional cloning of any immunoglobulin light chain variable region gene of interest at ApaLI and XhoI restriction sites. In step two, the CD1d gene preceded by the linker with a KpnI restriction site is amplified exactly as described above for heavy chain fusion products. Finally, in step three, the two fragments are joined by restriction digestion at the KpnI site followed by ligation employing standard protocols. The modifications of primer sequences required for amplification of the immunoglobulin light chain with either kappa or lambda light chain constant regions will be apparent to those skilled in the art.

Example 17

N Terminal Fusion Proteins

Employing strategies similar to those described above, chimeric molecules are constructed where the extracellular domain of CD1d is fused in frame with the amino terminus of the immunoglobulin heavy or light chain. These molecules are assembled in a 3 step process. In step 1, the extracellular domain of CD1d, including the signal sequence is PCR amplified from a plasmid template. This PCR modification adds a NotI site at the 5' end, and a portion of the gly,ser linker and a KPNI site at the 3' end. In step 2, the entire immunoglobulin heavy chain or light chain genes (variable and constant domains, or constant domain with restriction endonuclease sites for the insertion of a V gene), without the signal sequence, is PCR amplified. This PCR modification adds a portion of the gly,ser linker and a KpnI site at the 5' end, and an AgeI site at the 3' end. Finally, in step three, the two fragments are joined by restriction digestion at the KpnI site followed by ligation employing standard protocols. The modifications of primer sequences required for amplification of these genes and the construction of these molecules will be apparent to those skilled in the art.

Example 18

Construction of β2 Microglobulin

The fragment encoding the entire open reading frame of β2-microglobulin is generated by standard PCR using plasmid DNA as template. This fragment is cloned into a *Drosophila* expression vector such as pMT/V5-His. Cloning is designed so that there is not a 6-His Tag at the C terminal. This is easily accomplished by incorporating a "Stop" codon in the antisense primer immediately following the β2-microglobulin open reading frame. Methods to accomplish this construction are well known to those skilled in the art.

Example 19

Production of the Chimeric Antibody-CD1d/β2-Microglobulin Complex

Production of the antibody-CD1d/β2-microglobulin complex is done in 2 steps. In the first step, *Drosophila* S2 cells are transfected with the constructs encoding the chimeric antibody-CD1d and the antibody light chain gene. High expressing clones are selected and then transfected with the β2-microglobulin construct and clones expressing high levels of the antibody-CD1d/β-microglobulin complex isolated.

Step 1. Generation of *Drosophila* S2 cells stably transfected and producing antibody-CD1d. *Drosophila* S2 cells are triply transfected with plasmids that encode 1) antibody-CD1d (full IgG, F(ab), or F(ab')2 2) antibody light chain 3) pCOHYGRO (Invitrogen) Note that this plasmid confers resistance to the drug hygromycin. The triply transfected cells are selected with hygromycin and clones isolated. Expression of the recombinant anitbody-CD1d is induced in the cells by the addition of copper sulfate or cadmium chloride, and the cell supernatants screened by ELISA using antibodies specific for antibody and CD1d.

Step 2. Production and purification of the chimeric antibody-CD1d/β2-microglobulin complex. The highest antibody-CD1d producing clones from (A) is cotransfected with plasmids encoding β2-microglobulin (I.E) and pCOBLAST (Invitrogen). pCOBLAST confers resistance to Blasticidin. Stable clones are selected using Hygromycin and Blasticidin. Expression of the recombinant antibody-CD1d/β2M complex is induced in the cells by the addition of copper sulfate or cadmium chloride, and the cell supernatants screened by ELISA using antibodies specific for Ig, B2M, and CD1d. The clones that express the highest amount of antibody-CD1d/β2M complex are expanded and used to produce quantities of this molecule.

The highest expressing clone is expanded to 10+ L scale cultures in X-press serum free media, and induced to express this complex by the addition of copper sulfate or cadmium chloride to the media. The complex containing media is concentrated and dialyzed against 0.15M sodium phosphate buffer (pH 7.4). The antibody-CD1d/β2M complex is purified by Ni-NTA agarose chromatography, and then further purified by HPLC. The purified complex is incubated with a 3 fold molar excess of α-GalCer (CD1d ligand) overnight at room temperature. Excess α-GalCer is removed by dialysis. The final complex is purified by HPLC.

Example 20

In Vitro Testing of Complexes

The complexes prepared above are tested for the ability of the antibody part to bind the tumor antigen and for the proper conformation of the CD1d complex, by flow cytometry on target antigen-expressing cell lines revealed by an anti-CD1d mAb or by "sandwich elisa" on immobilized target antigen and revealed by anti-CD1d.

Ability of the bifunctional molecules to activate NKT cells is tested on freshly isolated mouse liver MNC or on α-GalCer-established human NKT cell lines. Due to the high degree of conservation between human and mouse CD1d, the two systems are cross reactive (Brossay et al., 1998. J Exp Med 188:1521 and Naidenko et al., 1999. J Exp Med 190:106964, 65). The read out after incubation with target cells coated with the CD1d-anti TAA complex is IFNγ release measured by Elisa or flow cytometry with CD1d-tetramer and intracellular cytoline staining (Matsuda et al., 2000. J Exp Med 192:741).

The monomer of CD1d-antibody is tested for specific activation of NKT cells when coated on a tumor cell line positive for the antigen recognized by the anti-TAA antibody fragment (i.e. human CEA transfected mouse cell line). Negative controls are either a tumor cell line that does not express the TAA, or an unrelated conjugate or α-GalCer alone. Activation of ex vivo mouse liver MNCs or enriched NKT cells (microbeads sorting) or human NKT cell lines will be tested by flow cytometry staining with CD1d tetramer and intracellular cytokine such as IFNγ.

Example 20

In Vivo Testing of Complexes

The anti-tumor activity of CD1d-α-GalCer restricted NKT cells was demonstrated mainly in models of liver and lung metastasis and the favoured cell lines used were EL-4 T lymphoma and B16-BL6 melanoma, both with BL/6 background (Smyth et al., 2002. Blood 99:1259; Hayakawa et al., 2001. Eur J Immunol 31:1720; Takeda et al., 2000. Int Immunol 12:909; and Cui et al., 1997. Science 278:1623). These cells are stably transfected with the surface antigen chosen as target, for example human CEA. In this case, the bifunctional molecules in human CEA-transgenic mice that are tolerant for this antigen and do not develop anti-CEA IgGs will be tested (Clarke et al., 1998. Cancer Res 58:1469). For liver metastasis, tumor cells are injected intrasplenically with or without removing the spleen, while for lung metastasis, injection is intravenous in the tail vein.

The complex is tested for systemic activation of NKT cells. Different amounts of conjugate or fusion are injected in normal mice with no tumor and results are compared with injection of α-GalCer alone. It is known that as few as 2 μg of α-GalCer (ip) leads to a rapid disappearance of NKT by activation induced cell death in spleen and liver (Hayakawa et al., 2001. Eur J Immunol 31:1720, Eberl and MacDonald. 2000, Eur J Immunol 30:985). Effects of CD1d-antibody conjugate versus α-GalCer alone is evaluated on liver MNCs by ex vivo flow cytometry with CD1d tetramer. Optimal amount of the bifunctional molecule with limited systemic effect is selected for in vivo tumor treatment.

Tumor graft inhibition: the tumor cell line expressing the TAA is coated in vitro with the selected CD1d-antibody fusion or conjugate and the cells are injected intravenously in the tail vein. The negative control is either the parental cell line negative for the TAA or the same tumor cells coated with a classical MHC Class I-antibody conjugate produced in the laboratory (such as H-2Kb-OVAp-anti CEA conjugate). After two weeks or at longer time, mice are sacrificed and metastatic nodules in the lung and possibly are counted is be compared with the known NKT-mediated effects of α-GalCer or IL-12 treatments (Hayakawa et al., 2001. Eur J Immunol 31:1720; Takeda et al., 2000. Int Immunol 12:909).

Established tumors: based on the results of the tumor protection experiments, a second set of in vivo experiments is used to test the effectiveness of CD1d-antibody bifunctional molecule on established tumors. Tumor cells are injected iv in the tail vein and treatment with the conjugate or fusion protein is started at different time points as a single or as multiple injections. Antibody fragment alone is injected in additional animals as a negative control. After two to three weeks, animals are sacrificed and metastatic nodules will be analyzed as above. Results are compared to the injection of α-GalCer alone in view of its known antimetastatic effect. In parallel experiments, liver metastasis will be favoured by intrasplenic injection of tumor cells and subsequent removal of the spleen. Similar treatments as above will be tested.

Role of NK cells: When liver and lungs are examined for metastatic nodules, MNCs are isolated and analysed by flow cytometry using anti-CD3 (or CD1d tetramer) and NK markers such as NK1.1 or DX5, allowing to evaluate the presence of CD1d-NKT (CD3+NK1.1+DX5−) and the proliferation of NK cells (CD3-NK1.1+DX5+). Results are compared with MNCs isolated from metastatic tissue treated with the antibody alone or with α-GalCer alone. Alternatively, in vivo depletion of NK cells by injections of anti-asialoGM1 are done in a group of mice at the time of tumor treatment (Smyth et al., 2002. Blood 99:1259, Hayakawa et al., 2001. Eur J Immunol 31:1720).

Human NKT cells: Human NKT cells can be propagated in vitro in contrast to mouse NKT and adoptive transfer studies in mice have shown that small numbers of NKT and NK cells can collaborate to suppress tumor metastasis (Wilson et al., 2002. Trends Mol Med 8:225; Smyth et al., 2002Curr Opin Immunol 14:165; and Smyth et al., 2002. Blood 99:1259). Human CD1d-antitumor antibody molecule is tested in vitro with human tumor cell lines that express the TAA such as CEA as targets and with freshly expanded human NKT cell lines. The read out will be IFNγ release and the respective role of NKT and NK cells will be assessed by non T cells depletion by microbeads negative sorting. Human CD1d-antitumor antibody molecule is also tested in vivo by adoptive transfer of human NKT cells in immunodeficient mice (SCID) grafted with human tumors positive for the TAA. Treatment with the bifunctional molecule of human CD1d-α-GalCer-antitumor antibody is performed as in the syngeneic mouse model.

The entire disclosure of all publications (including patents, patent applications, journal articles, laboratory manuals, books, or other documents) cited herein are hereby incorporated by reference.

What is claimed is:

1. A compound comprising:
   (a) a soluble CD1d complex comprising:
      i) a CD1d molecule or antigen-binding fragment thereof;
      ii) a β2-microglobulin molecule or fragment thereof; and
      iii) a stimulatory glycolipid antigen bound in the antigen binding groove of the CD1d molecule or antigen-binding fragment thereof; and
   (b) an antibody or an antigen-binding fragment thereof specific for a cell surface marker of a tumor cell;
   wherein said CD1d complex is linked to said antibody or fragment thereof; and wherein said compound stimulates the activation of the cytolytic activity of NKT cells.

2. The compound of claim 1, wherein said antigen is α-GalCer.

3. The compound of claim 1, wherein said antigen is a modified α-GalCer that is the OCH analog thereof having a long-chain sphingosine base shortened from C14 to C5 and acyl chain from C26 to C24.

4. The compound of claim 1, wherein said antigen-binding antibody fragment is a F(ab).

5. The compound of claim 1, wherein said antigen-binding antibody fragment is a scFv.

6. The compound of claim 1, wherein said antibody is a full-length antibody.

7. The compound of claim 1, wherein said cell surface marker is selected from the group consisting of: CEA, Her2/neu, EGFR type I or type II, CD19, CD20, CD22, Muc-1, PSMA, and STEAP.

8. The compound of claim 1, wherein said CD1d molecule or antigen-binding fragment thereof is attached to the heavy chain of said antibody.

9. The compound of claim 1, wherein said CD1d molecule or antigen-binding fragment thereof is attached to the light chain of said antibody.

10. The compound of claim 1, wherein said β2 microglobulin molecule is attached to the heavy chain of said antibody.

11. The compound of claim 1, wherein said β2 microglobulin molecule is attached to the light chain of said antibody.

12. The compound of claim 1, wherein the CD1d complex is linked in a fusion protein with the antibody or antigen-binding fragment thereof.

13. The compound of claim 7, wherein said cell surface marker is Her2/neu.

14. The compound of claim 1, wherein the CD1d molecule or antigen-binding fragment thereof of said CD1d complex comprises the extracellular portion of CD1d.

15. The compound of claim 14, wherein said extracellular portion comprises amino acids 1-297 of the amino acid sequence of SEQ ID NO: 40.

16. The compound of claim 5, wherein the variable light domain and the variable heavy domain of said scFv are linked by a peptide bridge.

17. The compound of claim 5, wherein the variable light domain and the variable heavy domain of said scFv are linked by one or more disulfide bonds.

18. The compound of claim 12, wherein the CD1d molecule of said CD1d complex is fused to said antibody or antigen-binding fragment thereof.

19. The compound of claim 18, wherein the CD1d molecule of said CD1d complex is fused to the amino terminus of the antibody or antigen-binding fragment thereof.

20. The compound of claim 18, wherein the CD1d molecule of said CD1d complex is fused to the carboxyl terminus of the antibody or antigen-binding fragment thereof.

21. The compound of claim 18, wherein a short linker amino acid sequence consisting of at least 3 and not more than 30 amino acids is situated between the CD1d molecule of said CD1d complex and the antibody or antigen-binding fragment thereof.

22. The compound of claim 21, wherein said short linker amino acid sequence comprises the sequence of SEQ ID NO: 1.

23. The compound of claim 21, wherein said short linker amino acid sequence comprises the sequence of SEQ ID NO: 2.

24. The compound of claim 12, wherein the β2-microglobulin molecule of said CD1d complex is fused to said antibody or antigen-binding fragment thereof.

25. The compound of claim 24, wherein the β2-microglobulin molecule of said CD1d complex is fused to the amino terminus of the antibody or antigen-binding fragment thereof.

26. The compound of claim 24, wherein the β2-microglobulin molecule of said CD1d complex is fused to the carboxyl terminus of the antibody or antigen-binding fragment thereof.

27. The compound of claim 24, wherein a short linker amino acid sequence of from about 3 to about 30 amino acids is situated between the β2-microglobulin molecule of said CD1d complex and the antibody or antigen-binding fragment thereof.

28. The compound of claim 27, wherein said short linker amino acid sequence comprises the sequence of SEQ ID NO: 1.

29. The compound of claim 27, wherein said short linker amino acid sequence comprises the sequence of SEQ ID NO: 2.

* * * * *

SEQUENCE LISTING

```
<160> NUMBER OF SEQ ID NOS: 54

<210> SEQ ID NO 1
<211> LENGTH: 15
<212> TYPE: PRT
<213> ORGANISM: Artificial Sequence
<220> FEATURE:
<223> OTHER INFORMATION: Artificial linker peptide

<400> SEQUENCE: 1

Gly Gly Gly Gly Ser Gly Gly Gly Gly Ser Gly Gly Gly Gly Ser
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Artificial linker peptide

<400> SEQUENCE: 2
```

Gly Gly Gly Gly Ser Gly Gly Gly Gly Ser Gly Gly Gly Ala Ser
1               5                   10                  15

<210> SEQ ID NO 3
<211> LENGTH: 38
<212> TYPE: DNA
<213> ORGANISM: Artificial Sequence
<220> FEATURE:
<223> OTHER INFORMATION: F(ab)-avidin sense fragment

<400> SEQUENCE: 3
aattgcggcc gcaaaccatg ggatggagct gtatcatc                              38

<210> SEQ ID NO 4
<211> LENGTH: 45
<212> TYPE: DNA
<213> ORGANISM: Artificial Sequence
<220> FEATURE:
<223> OTHER INFORMATION: F(ab)-avidin antisense fragment

<400> SEQUENCE: 4
cggggtacct gacccaccgc ctcctttctt gtccaccttg gtgtt                      45

<210> SEQ ID NO 5
<211> LENGTH: 38
<212> TYPE: DNA
<213> ORGANISM: Artificial Sequence
<220> FEATURE:
<223> OTHER INFORMATION: F(ab')2-avidin sense fragment

<400> SEQUENCE: 5
aattgcggcc gcaaaccatg ggatggagct gtatcatc                              38

<210> SEQ ID NO 6
<211> LENGTH: 45
<212> TYPE: DNA
<213> ORGANISM: Artificial Sequence
<220> FEATURE:
<223> OTHER INFORMATION: F(ab')2-avidin antisense fragment

<400> SEQUENCE: 6
cggggtacct gacccaccgc ctcctgggca cggtgggcat gtgtg                      45

<210> SEQ ID NO 7
<211> LENGTH: 38
<212> TYPE: DNA
<213> ORGANISM: Artificial Sequence
<220> FEATURE:
<223> OTHER INFORMATION: IgG1-avidin sense fragment

<400> SEQUENCE: 7
aattgcggcc gcaaaccatg ggatggagct gtatcatc                              38

<210> SEQ ID NO 8
<211> LENGTH: 45
<212> TYPE: DNA
<213> ORGANISM: Artificial Sequence
<220> FEATURE:
<223> OTHER INFORMATION: IgG1-avidin antisense fragment

<400> SEQUENCE: 8
cggggtacct gacccaccgc ctcctttacc cggagacagg gagag                      45

<210> SEQ ID NO 9
<211> LENGTH: 40
<212> TYPE: DNA

<210> SEQ ID NO 9
<211> LENGTH: 40
<212> TYPE: DNA
<213> ORGANISM: Artificial Sequence
<220> FEATURE:
<223> OTHER INFORMATION: Chick avidin sense primer

<400> SEQUENCE: 9
cggggtaccg gaggcggtgg gtcagccaga aagtgctcgc        40

<210> SEQ ID NO 10
<211> LENGTH: 28
<212> TYPE: DNA
<213> ORGANISM: Artificial Sequence
<220> FEATURE:
<223> OTHER INFORMATION: Chick avidin antisense primer

<400> SEQUENCE: 10
cgaccggtct ccttctgtgt gcgcaggc        28

<210> SEQ ID NO 11
<211> LENGTH: 823
<212> TYPE: DNA
<213> ORGANISM: Artificial Sequence
<220> FEATURE:
<223> OTHER INFORMATION: F(ab)-Avidin nucleotide construct

<400> SEQUENCE: 11
gcggccgcaa accatgggat ggagctgtat catcctcttc ttggtagcaa cagctacagg        60
cgcgcatatg gtcaccgtct cctcagcctc caccaagggc ccatcggtct tccccctggc       120
accctcctcc aagagcacct ctgggggcac agcggccctg ggctgcctgg tcaaggacta       180
cttccccgaa ccggtgacgg tgtcgtggaa ctcaggcgcc ctgaccagcg gcgtgcacac       240
cttcccggct gtcctacagt cctcaggact ctactccctc agcagcgtcg tgaccgtgcc       300
ctccagcagc ttgggcaccc agacctacat ctgcaacgtg aatcacaagc ccagcaacac       360
caaggtggac aagaaaggag cggtgggtc aggtaccgga ggcggtgggt cagccagaaa       420
gtgctcgctg actgggaaat ggaccaacga tctgggctcc aacatgacca tcggggctgt       480
gaacagcaga ggtgaattca caggcaccta catcacagcc gtaacagcca tcaaatga       540
gatcaaagag tcaccactgc atgggacaca aaacaccatc aacaagagga cccagcccac       600
ctttggcttc accgtcaatt ggaagttttc agagtccacc actgtcttca cgggccagtg       660
cttcatagac aggaatggga aggaggtcct gaagaccatg tggctgctgc ggtcaagtgt       720
taatgacatt ggtgatgact ggaaagctac cagggtcggc atcaacatct tcactcgcct       780
gcgcacacag aaggagaccg gtcatcatca ccatcaccat tga       823

<210> SEQ ID NO 12
<211> LENGTH: 269
<212> TYPE: PRT
<213> ORGANISM: Artificial Sequence
<220> FEATURE:
<223> OTHER INFORMATION: F(ab)-Avidin polypeptide construct

<400> SEQUENCE: 12

Met Gly Trp Ser Cys Ile Ile Leu Phe Leu Val Ala Thr Ala Thr Gly
1               5                   10                  15

Ala His Met Val Thr Val Ser Ser Ala Ser Thr Lys Gly Pro Ser Val
            20                  25                  30

Phe Pro Leu Ala Pro Ser Ser Lys Ser Thr Ser Gly Gly Thr Ala Ala
        35                  40                  45

Leu Gly Cys Leu Val Lys Asp Tyr Phe Pro Glu Pro Val Thr Val Ser
    50                  55                  60

```
Trp Asn Ser Gly Ala Leu Thr Ser Gly Val His Thr Phe Pro Ala Val
 65                  70                  75                  80

Leu Gln Ser Ser Gly Leu Tyr Ser Leu Ser Val Val Thr Val Pro
                 85                  90                  95

Ser Ser Ser Leu Gly Thr Gln Thr Tyr Ile Cys Asn Val Asn His Lys
            100                 105                 110

Pro Ser Asn Thr Lys Val Asp Lys Lys Gly Gly Gly Ser Gly Thr
        115                 120                 125

Gly Gly Gly Gly Ser Ala Arg Lys Cys Ser Leu Thr Gly Lys Trp Thr
130                 135                 140

Asn Asp Leu Gly Ser Asn Met Thr Ile Gly Ala Val Asn Ser Arg Gly
145                 150                 155                 160

Glu Phe Thr Gly Thr Tyr Ile Thr Ala Val Thr Ala Thr Ser Asn Glu
                165                 170                 175

Ile Lys Glu Ser Pro Leu His Gly Thr Gln Asn Thr Ile Asn Lys Arg
            180                 185                 190

Thr Gln Pro Thr Phe Gly Phe Thr Val Asn Trp Lys Phe Ser Glu Ser
        195                 200                 205

Thr Thr Val Phe Thr Gly Gln Cys Phe Ile Asp Arg Asn Gly Lys Glu
210                 215                 220

Val Leu Lys Thr Met Trp Leu Leu Arg Ser Ser Val Asn Asp Ile Gly
225                 230                 235                 240

Asp Asp Trp Lys Ala Thr Arg Val Gly Ile Asn Ile Phe Thr Arg Leu
                245                 250                 255

Arg Thr Gln Lys Glu Thr Gly His His His His His His
            260                 265

<210> SEQ ID NO 13
<211> LENGTH: 871
<212> TYPE: DNA
<213> ORGANISM: Artificial Sequence
<220> FEATURE:
<223> OTHER INFORMATION: F(ab')2-Avidin nucleotide construct

<400> SEQUENCE: 13
gcggccgcaa accatgggat ggagctgtat catcctcttc ttggtagcaa cagctacagg      60
cgcgcatatg gtcaccgtct cctcagcctc caccaagggc ccatcggtct tccccctggc     120
accctcctcc aagagcacct ctgggggcac agcggccctg ggctgcctgg tcaaggacta     180
cttccccgaa ccggtgacgg tgtcgtggaa ctcaggcgcc ctgaccagcg gcgtgcacac     240
cttcccggct gtcctacagt cctcaggact ctactccctc agcagcgtcg tgaccgtgcc     300
ctccagcagc ttgggcaccc agacctacat ctgcaacgtg aatcacaagc ccagcaacac     360
caaggtggac aagaaagttg agcccaaatc ttgtgacaaa actcacacat gcccaccgtg     420
cccaggaggc ggtgggtcag gtaccggagg cggtgggtca gccagaaagt gctcgctgac     480
tgggaaatgg accaacgatc tgggctccaa catgaccatc ggggctgtga acagcagagg     540
tgaattcaca ggcacctaca tcacagccgt aacagccaca tcaaatgaga tcaaagagtc     600
accactgcat gggacacaaa acaccatcaa caaggaggacc cagcccacct ttggcttcac     660
cgtcaattgg aagttttcag agtccaccac tgtcttcacg gccagtgct tcatagacag     720 gaatgggaag gaggtcctga agaccatgtg gctgctgcgg tcaagtgtta atgacattgg     780
tgatgactga aaagctacca gggtcggcat caacatcttc actcgcctgc gcacacagaa     840
ggagaccggt catcatcacc atcaccattg a                                    871
```

<210> SEQ ID NO 14
<211> LENGTH: 285
<212> TYPE: PRT
<213> ORGANISM: Artificial Sequence
<220> FEATURE:
<223> OTHER INFORMATION: F(ab')2-Avidin polypetide construct

<400> SEQUENCE: 14

```
Met Gly Trp Ser Cys Ile Ile Leu Phe Leu Val Ala Thr Ala Thr Gly
1               5                   10                  15

Ala His Met Val Thr Val Ser Ser Ala Ser Thr Lys Gly Pro Ser Val
            20                  25                  30

Phe Pro Leu Ala Pro Ser Ser Lys Ser Thr Ser Gly Gly Thr Ala Ala
        35                  40                  45

Leu Gly Cys Leu Val Lys Asp Tyr Phe Pro Glu Pro Val Thr Val Ser
    50                  55                  60

Trp Asn Ser Gly Ala Leu Thr Ser Gly Val His Thr Phe Pro Ala Val
65                  70                  75                  80

Leu Gln Ser Ser Gly Leu Tyr Ser Leu Ser Ser Val Val Thr Val Pro
                85                  90                  95

Ser Ser Ser Leu Gly Thr Gln Thr Tyr Ile Cys Asn Val Asn His Lys
            100                 105                 110

Pro Ser Asn Thr Lys Val Asp Lys Lys Val Glu Pro Lys Ser Cys Asp
        115                 120                 125

Lys Thr His Thr Cys Pro Pro Cys Pro Gly Gly Gly Ser Gly Thr
    130                 135                 140

Gly Gly Gly Gly Ser Ala Arg Lys Cys Ser Leu Thr Gly Lys Trp Thr
145                 150                 155                 160

Asn Asp Leu Gly Ser Asn Met Thr Ile Gly Ala Val Asn Ser Arg Gly
                165                 170                 175

Glu Phe Thr Gly Thr Tyr Ile Thr Ala Val Thr Ala Thr Ser Asn Glu
            180                 185                 190

Ile Lys Glu Ser Pro Leu His Gly Thr Gln Asn Thr Ile Asn Lys Arg
        195                 200                 205

Thr Gln Pro Thr Phe Gly Phe Thr Val Asn Trp Lys Phe Ser Glu Ser
    210                 215                 220

Thr Thr Val Phe Thr Gly Gln Cys Phe Ile Asp Arg Asn Gly Lys Glu
225                 230                 235                 240

Val Leu Lys Thr Met Trp Leu Leu Arg Ser Ser Val Asn Asp Ile Gly
                245                 250                 255

Asp Asp Trp Lys Ala Thr Arg Val Gly Ile Asn Ile Phe Thr Arg Leu
            260                 265                 270

Arg Thr Gln Lys Glu Thr Gly His His His His His
        275                 280                 285
```

<210> SEQ ID NO 15
<211> LENGTH: 1522
<212> TYPE: DNA
<213> ORGANISM: Artificial Sequence
<220> FEATURE:
<223> OTHER INFORMATION: IgG1 Avidin nucleotide construct

<400> SEQUENCE: 15

```
gcggccgcaa accatgggat ggagctgtat catcctcttc ttggtagcaa cagctacagg    60
cgcgcatatg gtcaccgtct cctcagcctc caccaagggc ccatcggtct tccccctggc   120
```

```
accctcctcc aagagcacct ctgggggcac agcggccctg ggctgcctgg tcaaggacta    180
cttccccgaa ccggtgacgg tgtcgtggaa ctcaggcgcc ctgaccagcg gcgtgcacac    240
cttcccggct gtcctacagt cctcaggact ctactccctc agcagcgtcg tgaccgtgcc    300
ctccagcagc ttgggcaccc agacctacat ctgcaacgtg aatcacaagc ccagcaacac    360
caaggtggac aagaaagttg agcccaaatc ttgtgacaaa actcacacat gcccaccgtg    420
cccagcacct gaactcctgg ggggaccgtc agtcttcctc ttccccccaa aacccaagga    480
caccctcatg atctcccgga cccctgaggt cacatgcgtg gtggtggacg tgagccacga    540
agaccctgag gtcaagttca actggtacgt ggacggcgtg gaggtgcata atgccaagac    600
aaagccgcgg gaggagcagt acaacagcac gtaccgtgtg gtcagcgtcc tcaccgtcct    660
gcaccaggac tggctgaatg gcaaggagta caagtgcaag gtctccaaca aagccctccc    720
agcccccatc gagaaaacca tctccaaagc caaagggcag ccccgagaac cacaggtgta    780
caccctgccc ccatcccggg atgagctgac caagaaccag gtcagcctga cctgcctggt    840
caaaggcttc tatcccagcg acatcgccgt ggagtgggag agcaatgggc agccggagaa    900
caactacaag accacgcctc ccgtgctgga ctccgacggc tccttcttcc tctacagcaa    960
gctcaccgtg gacaagagca ggtggcagca ggggaacgtc ttctcatgct ccgtgatgca   1020
tgaggctctg cacaaccact acacgcagaa gagcctctcc ctgtctccgg gtaaaggagg   1080
cggtgggtca ggtaccggag gcggtgggtc agccagaaag tgctcgctga ctgggaaatg   1140
gaccaacgat ctgggctcca acatgaccat cggggctgtg aacagcagag gtgaattcac   1200
aggcacctac atcacagccg taacagccac atcaaatgag atcaaagagt caccactgca   1260
tgggacacaa aacaccatca caagaggacc cagcccacc tttggcttca ccgtcaattg   1320
gaagttttca gagtccacca ctgtcttcac gggccagtgc ttcatagaca ggaatgggaa   1380
ggaggtcctg aagaccatgt ggctgctgcg gtcaagtgtt aatgacattg gtgatgactg   1440
gaaagctacc agggtcggca tcaacatctt cactcgcctg cgcacacaga aggagaccgg   1500
tcatcatcac catcaccatt ga                                             1522
```

<210> SEQ ID NO 16
<211> LENGTH: 502
<212> TYPE: PRT
<213> ORGANISM: Artificial Sequence
<220> FEATURE:
<223> OTHER INFORMATION: IgG1 Avidin polypeptide construct
<400> SEQUENCE: 16

```
Met Gly Trp Ser Cys Ile Ile Leu Phe Leu Val Ala Thr Ala Thr Gly
1               5                   10                  15

Ala His Met Val Thr Val Ser Ser Ala Ser Thr Lys Gly Pro Ser Val
            20                  25                  30

Phe Pro Leu Ala Pro Ser Ser Lys Ser Thr Ser Gly Gly Thr Ala Ala
        35                  40                  45

Leu Gly Cys Leu Val Lys Asp Tyr Phe Pro Glu Pro Val Thr Val Ser
    50                  55                  60

Trp Asn Ser Gly Ala Leu Thr Ser Gly Val His Thr Phe Pro Ala Val
65                  70                  75                  80

Leu Gln Ser Ser Gly Leu Tyr Ser Leu Ser Ser Val Val Thr Val Pro
                85                  90                  95

Ser Ser Ser Leu Gly Thr Gln Thr Tyr Ile Cys Asn Val Asn His Lys
            100                 105                 110
```

```
Pro Ser Asn Thr Lys Val Asp Lys Lys Val Glu Pro Lys Ser Cys Asp
            115                 120                 125
Lys Thr His Thr Cys Pro Pro Cys Pro Ala Pro Glu Leu Leu Gly Gly
        130                 135                 140
Pro Ser Val Phe Leu Phe Pro Pro Lys Pro Lys Asp Thr Leu Met Ile
145                 150                 155                 160
Ser Arg Thr Pro Glu Val Thr Cys Val Val Val Asp Val Ser His Glu
                165                 170                 175
Asp Pro Glu Val Lys Phe Asn Trp Tyr Val Asp Gly Val Glu Val His
            180                 185                 190
Asn Ala Lys Thr Lys Pro Arg Glu Glu Gln Tyr Asn Ser Thr Tyr Arg
        195                 200                 205
Val Val Ser Val Leu Thr Val Leu His Gln Asp Trp Leu Asn Gly Lys
    210                 215                 220
Glu Tyr Lys Cys Lys Val Ser Asn Lys Ala Leu Pro Ala Pro Ile Glu
225                 230                 235                 240
Lys Thr Ile Ser Lys Ala Lys Gly Gln Pro Arg Glu Pro Gln Val Tyr
                245                 250                 255
Thr Leu Pro Pro Ser Arg Asp Glu Leu Thr Lys Asn Gln Val Ser Leu
            260                 265                 270
Thr Cys Leu Val Lys Gly Phe Tyr Pro Ser Asp Ile Ala Val Glu Trp
        275                 280                 285
Glu Ser Asn Gly Gln Pro Glu Asn Asn Tyr Lys Thr Thr Pro Pro Val
    290                 295                 300
Leu Asp Ser Asp Gly Ser Phe Phe Leu Tyr Ser Lys Leu Thr Val Asp
305                 310                 315                 320
Lys Ser Arg Trp Gln Gln Gly Asn Val Phe Ser Cys Ser Val Met His
                325                 330                 335
Glu Ala Leu His Asn His Tyr Thr Gln Lys Ser Leu Ser Leu Ser Pro
            340                 345                 350
Gly Lys Gly Gly Gly Gly Ser Gly Thr Gly Gly Gly Ser Ala Arg
        355                 360                 365
Lys Cys Ser Leu Thr Gly Lys Trp Thr Asn Asp Leu Gly Ser Asn Met
        370                 375                 380
Thr Ile Gly Ala Val Asn Ser Arg Gly Glu Phe Thr Gly Thr Tyr Ile
385                 390                 395                 400
Thr Ala Val Thr Ala Thr Ser Asn Glu Ile Lys Glu Ser Pro Leu His
                405                 410                 415
Gly Thr Gln Asn Thr Ile Asn Lys Arg Thr Gln Pro Thr Phe Gly Phe
            420                 425                 430
Thr Val Asn Trp Lys Phe Ser Glu Ser Thr Thr Val Phe Thr Gly Gln
        435                 440                 445
Cys Phe Ile Asp Arg Asn Gly Lys Glu Val Leu Lys Thr Met Trp Leu
450                 455                 460
Leu Arg Ser Ser Val Asn Asp Ile Gly Asp Asp Trp Lys Ala Thr Arg
465                 470                 475                 480
Val Gly Ile Asn Ile Phe Thr Arg Leu Arg Thr Gln Lys Glu Thr Gly
                485                 490                 495
His His His His His His
            500

<210> SEQ ID NO 17
<211> LENGTH: 57
<212> TYPE: DNA
```

```
<213> ORGANISM: Artificial Sequence
<220> FEATURE:
<223> OTHER INFORMATION: BirA Sense Sequence

<400> SEQUENCE: 17
ccggtggtgg cggtctgaac gacatcttcg aggctcagaa atcgaatgg cacgaat          57

<210> SEQ ID NO 18
<211> LENGTH: 57
<212> TYPE: DNA
<213> ORGANISM: Artificial Sequence
<220> FEATURE:
<223> OTHER INFORMATION: BirA Antisense Sequence

<400> SEQUENCE: 18
ccggattcgt gccattcgat ttctgagcc tcgaagatgt cgttcagacc gccacca          57

<210> SEQ ID NO 19
<211> LENGTH: 34
<212> TYPE: DNA
<213> ORGANISM: Artificial Sequence
<220> FEATURE:
<223> OTHER INFORMATION: E1 sense sequence

<400> SEQUENCE: 19
cacggtaccg atatggggtg cctgctgttt ctgc                                  34

<210> SEQ ID NO 20
<211> LENGTH: 30
<212> TYPE: DNA
<213> ORGANISM: Artificial Sequence
<220> FEATURE:
<223> OTHER INFORMATION: E1 antisense

<400> SEQUENCE: 20
cagaccggtc cagtagagga cgatgtcctg                                       30

<210> SEQ ID NO 21
<211> LENGTH: 978
<212> TYPE: DNA
<213> ORGANISM: Artificial Sequence
<220> FEATURE:
<223> OTHER INFORMATION: Construct of nucleotide sequence for
      extracellular domain of CD1d

<400> SEQUENCE: 21
ggtaccgata tggggtgcct gctgtttctg ctgctctggg cgctcctcca ggcttgggga      60
agcgctgaag tcccgcaaag cttttcccc ctccgctgcc tccagatctc gtccttcgcc     120
aatagcagct ggacgcgcac cgacggcttg gcgtggctgg gggagctgca gacgcacagc     180
tggagcaacg actcggacac cgtccgctct ctgaagcctt ggtcccaggg cacgttcagc     240
gaccagcagt gggagacgct gcagcatata tttcgggttt atcgaagcag cttcaccagg     300
gacgtgaagg aattcgccaa aatgctacgc ttatcctatc ccttggagct ccaggtgtcc     360
gctggctgtg aggtgcaccc tgggaacgcc tcaaataact tcttccatgt agcatttcaa     420
ggaaaagata tcctgagttt ccaaggaact tcttgggagc aacccaaga ggccccactt     480 tgggtaaact tggccattca agtgctcaac aggacaagt ggacgaggga acagtgcag     540 tggctcctta atggcaccctg cccccaattt gtcagtggcc tccttgagtc agggaagtcg     600
gaactgaaga gcaagtgaa gcccaaggcc tggctgtccc gtggcccag tcctggccct     660 ggccgtctgc tgctggtgtg ccatgtctca ggattctacc caaagcctgt atgggtgaag     720
```

```
tggatgcggg gtgagcagga gcagcagggc actcagccag gggacatcct gcccaatgct    780
gacgagacat ggtatctccg agcaaccctg gatgtggtgg ctggggaggc agctggcctg    840
tcctgtcggg tgaagcacag cagtctagag ggccaggaca tcgtcctcta ctggaccggt    900
ggtggcggtc tgaacgacat cttcgaggct cagaaaatcg aatggcacga atccggtcat    960
catcaccatc accattga                                                  978
```

<210> SEQ ID NO 22
<211> LENGTH: 322
<212> TYPE: PRT
<213> ORGANISM: Artificial Sequence
<220> FEATURE:
<223> OTHER INFORMATION: Construct of polypeptide sequence for
     extracellular domain of CD1d

<400> SEQUENCE: 22

```
Met Gly Cys Leu Leu Phe Leu Leu Leu Trp Ala Leu Leu Gln Ala Trp
1               5                   10                  15

Gly Ser Ala Glu Val Pro Gln Arg Leu Phe Pro Leu Arg Cys Leu Gln
            20                  25                  30

Ile Ser Ser Phe Ala Asn Ser Ser Trp Thr Arg Thr Asp Gly Leu Ala
        35                  40                  45

Trp Leu Gly Glu Leu Gln Thr His Ser Trp Ser Asn Asp Ser Asp Thr
    50                  55                  60

Val Arg Ser Leu Lys Pro Trp Ser Gln Gly Thr Phe Ser Asp Gln Gln
65                  70                  75                  80

Trp Glu Thr Leu Gln His Ile Phe Arg Val Tyr Arg Ser Ser Phe Thr
                85                  90                  95

Arg Asp Val Lys Glu Phe Ala Lys Met Leu Arg Leu Ser Tyr Pro Leu
            100                 105                 110

Glu Leu Gln Val Ser Ala Gly Cys Glu Val His Pro Gly Asn Ala Ser
        115                 120                 125

Asn Asn Phe Phe His Val Ala Phe Gln Gly Lys Asp Ile Leu Ser Phe
    130                 135                 140

Gln Gly Thr Ser Trp Glu Pro Thr Gln Glu Ala Pro Leu Trp Val Asn
145                 150                 155                 160

Leu Ala Ile Gln Val Leu Asn Gln Asp Lys Trp Thr Arg Glu Thr Val
                165                 170                 175

Gln Trp Leu Leu Asn Gly Thr Cys Pro Gln Phe Val Ser Gly Leu Leu
            180                 185                 190

Glu Ser Gly Lys Ser Glu Leu Lys Lys Gln Val Lys Pro Lys Ala Trp
        195                 200                 205

Leu Ser Arg Gly Pro Ser Pro Gly Pro Gly Arg Leu Leu Leu Val Cys
    210                 215                 220

His Val Ser Gly Phe Tyr Pro Lys Pro Val Trp Val Lys Trp Met Arg
225                 230                 235                 240

Gly Glu Gln Glu Gln Gln Gly Thr Gln Pro Gly Asp Ile Leu Pro Asn
                245                 250                 255

Ala Asp Glu Thr Trp Tyr Leu Arg Ala Thr Leu Asp Val Val Ala Gly
            260                 265                 270

Glu Ala Ala Gly Leu Ser Cys Arg Val Lys His Ser Ser Leu Glu Gly
        275                 280                 285

Gln Asp Ile Val Leu Tyr Trp Thr Gly Gly Gly Gly Leu Asn Asp Ile
    290                 295                 300

Phe Glu Ala Gln Lys Ile Glu Trp His Glu Ser Gly His His His His
```

His His

<210> SEQ ID NO 23
<211> LENGTH: 38
<212> TYPE: DNA
<213> ORGANISM: Artificial Sequence
<220> FEATURE:
<223> OTHER INFORMATION: F(ab)-B2M sense construct

<400> SEQUENCE: 23
aattgcggcc gcaaaccatg ggatggagct gtatcatc                              38

<210> SEQ ID NO 24
<211> LENGTH: 45
<212> TYPE: DNA
<213> ORGANISM: Artificial Sequence
<220> FEATURE:
<223> OTHER INFORMATION: F9ab)-B2M antisense construct

<400> SEQUENCE: 24
cggggtacct gacccaccgc ctcctttctt gtccaccttg gtgtt                      45

<210> SEQ ID NO 25
<211> LENGTH: 37
<212> TYPE: DNA
<213> ORGANISM: Artificial Sequence
<220> FEATURE:
<223> OTHER INFORMATION: F(ab')2-B2M sense construct

<400> SEQUENCE: 25
attgcggccg caaaccatgg gatggagctg tatcatc                               37

<210> SEQ ID NO 26
<211> LENGTH: 45
<212> TYPE: DNA
<213> ORGANISM: Artificial Sequence
<220> FEATURE:
<223> OTHER INFORMATION: F(ab')2-B2M antisense construct

<400> SEQUENCE: 26
cggggtacct gacccaccgc ctcctgggca cggtgggcat gtgtg                      45

<210> SEQ ID NO 27
<211> LENGTH: 38
<212> TYPE: DNA
<213> ORGANISM: Artificial Sequence
<220> FEATURE:
<223> OTHER INFORMATION: IgG1-B2M sense construct

<400> SEQUENCE: 27
aattgcggcc gcaaaccatg ggatggagct gtatcatc                              38

<210> SEQ ID NO 28
<211> LENGTH: 45
<212> TYPE: DNA
<213> ORGANISM: Artificial Sequence
<220> FEATURE:
<223> OTHER INFORMATION: IgG1-B2M antisense construct

<400> SEQUENCE: 28
cggggtacct gacccaccgc ctcctttacc cggagacagg gagag                      45

<210> SEQ ID NO 29
<211> LENGTH: 39

```
<212> TYPE: DNA
<213> ORGANISM: Artificial Sequence
<220> FEATURE:
<223> OTHER INFORMATION: artificial sense primer to construct
      beta2-microglobulin

<400> SEQUENCE: 29
cggggtaccg gaggcggtgg gtcaatccag cgtactcca                         39

<210> SEQ ID NO 30
<211> LENGTH: 26
<212> TYPE: DNA
<213> ORGANISM: Artificial Sequence
<220> FEATURE:
<223> OTHER INFORMATION: artificial antisense primer to construct
      beta2-microglobulin

<400> SEQUENCE: 30
cgaccggtca tgtctcgatc ccactt                                      26

<210> SEQ ID NO 31
<211> LENGTH: 736
<212> TYPE: DNA
<213> ORGANISM: Artificial Sequence
<220> FEATURE:
<223> OTHER INFORMATION: Nucleotide sequence of the chimeric
      F(ab)-beta2-microglobulin

<400> SEQUENCE: 31
gcggccgcaa accatgggat ggagctgtat catcctcttc ttggtagcaa cagctacagg    60
cgcgcatatg gtcaccgtct cctcagcctc caccaagggc ccatcggtct tccccctggc   120
accctcctcc aagagcacct ctgggggcac agcggccctg ggctgcctgg tcaaggacta   180
cttccccgaa ccggtgacgg tgtcgtggaa ctcaggcgcc ctgaccagcg gcgtgcacac   240
cttcccggct gtcctacagt cctcaggact ctactccctc agcagcgtcg tgaccgtgcc   300
ctccagcagc ttgggcaccc agacctacat ctgcaacgtg aatcacaagc ccagcaacac   360
caaggtggac aagaaaggag cggtgggtc aggtaccgga ggcggtgggt caatccagcg   420
tactccaaag attcaggttt actcacgtca tccagcagag aatggaaagt caaatttcct   480
gaattgctat gtgtctgggt ttcatccatc cgacattgaa gttgacttac tgaagaatgg   540
agagagaatt gaaaaagtgg agcattcaga cttgtctttc agcaaggact ggtctttcta   600
tctcttgtac tacactgaat tcaccccac tgaaaaagat gagtatgcct gccgtgtgaa   660
ccatgtgact ttgtcacagc ccaagatagt taagtgggat cgagacatga ccggtcatca   720
tcaccatcac cattga                                                 736

<210> SEQ ID NO 32
<211> LENGTH: 240
<212> TYPE: PRT
<213> ORGANISM: Artificial Sequence
<220> FEATURE:
<223> OTHER INFORMATION: Polypeptide sequence of the chimeric
      F(ab)-beta2-microglobulin

<400> SEQUENCE: 32

Met Gly Trp Ser Cys Ile Ile Leu Phe Leu Val Ala Thr Ala Thr Gly
1               5                   10                  15

Ala His Met Val Thr Val Ser Ser Ala Ser Thr Lys Gly Pro Ser Val
                20                  25                  30

Phe Pro Leu Ala Pro Ser Ser Lys Ser Thr Ser Gly Gly Thr Ala Ala
            35                  40                  45
```

Leu Gly Cys Leu Val Lys Asp Tyr Phe Pro Glu Pro Val Thr Val Ser
    50                  55                  60

Trp Asn Ser Gly Ala Leu Thr Ser Gly Val His Thr Phe Pro Ala Val
65                  70                  75                  80

Leu Gln Ser Ser Gly Leu Tyr Ser Leu Ser Ser Val Val Thr Val Pro
                85                  90                  95

Ser Ser Ser Leu Gly Thr Gln Thr Tyr Ile Cys Asn Val Asn His Lys
            100                 105                 110

Pro Ser Asn Thr Lys Val Asp Lys Lys Gly Gly Gly Ser Gly Thr
        115                 120                 125

Gly Gly Gly Gly Ser Ile Gln Arg Thr Pro Lys Ile Gln Val Tyr Ser
130                 135                 140

Arg His Pro Ala Glu Asn Gly Lys Ser Asn Phe Leu Asn Cys Tyr Val
145                 150                 155                 160

Ser Gly Phe His Pro Ser Asp Ile Glu Val Asp Leu Leu Lys Asn Gly
                165                 170                 175

Glu Arg Ile Glu Lys Val Glu His Ser Asp Leu Val Phe Ser Lys Asp
            180                 185                 190

Trp Ser Phe Tyr Leu Leu Tyr Tyr Thr Glu Phe Thr Pro Thr Glu Lys
        195                 200                 205

Asp Glu Tyr Ala Cys Arg Val Asn His Val Thr Leu Ser Gln Pro Lys
210                 215                 220

Ile Val Lys Trp Asp Arg Asp Met Thr Gly His His His His His
225                 230                 235                 240

<210> SEQ ID NO 33
<211> LENGTH: 783
<212> TYPE: DNA
<213> ORGANISM: Artificial Sequence
<220> FEATURE:
<223> OTHER INFORMATION: Nucleotide sequence of the chimeric
      F(ab')2-beta2-microglobulin

<400> SEQUENCE: 33
gcggccgcaa accatgggat ggagctgtat catcctcttc ttggtagcaa cagctacagg      60
cgcgcatatg gtcaccgtct cctcagcctc caccaagggc ccatcggtct tccccctggc    120
accctcctcc aagagcacct ctgggggcac agcggccctg ggctgcctgg tcaaggacta    180
cttccccgaa ccggtgacgg tgtcgtggaa ctcaggcgcc ctgaccagcg gcgtgcacac    240
cttcccggct gtcctacagt cctcaggact ctactccctc agcagcgtcg tgaccgtgcc    300
ctccagcagc ttgggcaccc agacctacat ctgcaacgtg aatcacaagc ccagcaacac    360
caaggtggac aagaaagttg agcccaaatc ttgtgacaaa actcacacat gcccaccgtg    420
cccaggaggc ggtgggtcag gtaccggagg cggtgggtca atccagcgta ctccaaagat    480
tcaggtttac tcacgtcatc cagcagaaaa tggaaagtca aatttcctga attgctatgt    540
gtctgggttt catccatccg acattgaagt tgacttactg aagaatggag agagaattga    600
aaaagtggag cattcagact tgtctttcag caaggactgg tctttctatc tcttgtacta    660
cactgaattc accccactg aaaagatgag tatgcctgcc gtgtgaacca tgtgactttg    720
tcacagccca agatagttaa gtgggatcga gacatgaccg gtcatcatca ccatcaccat    780
tga                                                                   783

<210> SEQ ID NO 34
<211> LENGTH: 256

```
<212> TYPE: PRT
<213> ORGANISM: Artificial Sequence
<220> FEATURE:
<223> OTHER INFORMATION: Nucleotide sequence of the chimeric
      F(ab')2-beta2-microglobulin

<400> SEQUENCE: 34

Met Gly Trp Ser Cys Ile Ile Leu Phe Leu Val Ala Thr Ala Thr Gly
1               5                   10                  15

Ala His Met Val Thr Val Ser Ser Ala Ser Thr Lys Gly Pro Ser Val
            20                  25                  30

Phe Pro Leu Ala Pro Ser Ser Lys Ser Thr Ser Gly Gly Thr Ala Ala
        35                  40                  45

Leu Gly Cys Leu Val Lys Asp Tyr Phe Pro Glu Pro Val Thr Val Ser
    50                  55                  60

Trp Asn Ser Gly Ala Leu Thr Ser Gly Val His Thr Phe Pro Ala Val
65                  70                  75                  80

Leu Gln Ser Ser Gly Leu Tyr Ser Leu Ser Ser Val Val Thr Val Pro
                85                  90                  95

Ser Ser Ser Leu Gly Thr Gln Thr Tyr Ile Cys Asn Val Asn His Lys
            100                 105                 110

Pro Ser Asn Thr Lys Val Asp Lys Lys Val Glu Pro Lys Ser Cys Asp
        115                 120                 125

Lys Thr His Thr Cys Pro Pro Cys Pro Gly Gly Gly Gly Ser Gly Thr
    130                 135                 140

Gly Gly Gly Gly Ser Ile Gln Arg Thr Pro Lys Ile Gln Val Tyr Ser
145                 150                 155                 160

Arg His Pro Ala Glu Asn Gly Lys Ser Asn Phe Leu Asn Cys Tyr Val
                165                 170                 175

Ser Gly Phe His Pro Ser Asp Ile Glu Val Asp Leu Leu Lys Asn Gly
            180                 185                 190

Glu Arg Ile Glu Lys Val Glu His Ser Asp Leu Val Phe Ser Lys Asp
        195                 200                 205

Trp Ser Phe Tyr Leu Leu Tyr Tyr Thr Glu Phe Thr Pro Thr Glu Lys
    210                 215                 220

Asp Glu Tyr Ala Cys Arg Val Asn His Val Thr Leu Ser Gln Pro Lys
225                 230                 235                 240

Ile Val Lys Trp Asp Arg Asp Met Thr Gly His His His His His
                245                 250                 255

<210> SEQ ID NO 35
<211> LENGTH: 1435
<212> TYPE: DNA
<213> ORGANISM: Artificial Sequence
<220> FEATURE:
<223> OTHER INFORMATION: Nucleotide sequence of the chimeric full
      IgG1-beta2 microglobulin

<400> SEQUENCE: 35
gcggccgcaa accatgggat ggagctgtat catcctcttc ttggtagcaa cagctacagg      60
cgcgcatatg gtcaccgtct cctcagcctc caccaagggc ccatcggtct tccccctggc    120
accctcctcc aagagcacct ctgggggcac agcggccctg ggctgcctgg tcaaggacta    180
cttccccgaa ccggtgacgg tgtcgtggaa ctcaggcgcc ctgaccagcg gcgtgcacac    240
cttcccggct gtcctacagt cctcaggact ctactccctc agcagcgtcg tgaccgtgcc    300
ctccagcagc ttgggcaccc agacctacat ctgcaacgtg aatcacaagc ccagcaacac    360
```

```
caaggtggac aagaaagttg agcccaaatc ttgtgacaaa actcacacat gcccaccgtg    420
cccagcacct gaactcctgg ggggaccgtc agtcttcctc ttccccccaa aacccaagga    480
caccctcatg atctcccgga cccctgaggt cacatgcgtg gtggtggacg tgagccacga    540
agaccctgag gtcaagttca actggtacgt ggacggcgtg gaggtgcata atgccaagac    600
aaagccgcgg gaggagcagt acaacagcac gtaccgtgtg gtcagcgtcc tcaccgtcct    660
gcaccaggac tggctgaatg gcaaggagta caagtgcaag gtctccaaca aagccctccc    720
agcccccatc gagaaaacca tctccaaagc caaagggcag cccgagaac cacaggtgta    780 caccctgccc ccatcccggg atgagctgac caagaaccag gtcagcctga cctgcctggt    840
caaaggcttc tatcccagcg acatcgccgt ggagtgggag agcaatgggc agccggagaa    900
caactacaag accacgcctc ccgtgctgga ctccgacggc tccttcttcc tctacagcaa    960
gctcaccgtg gacaagagca ggtggcagca ggggaacgtc ttctcatgct ccgtgatgca    1020
tgaggctctg cacaaccact acacgcagaa gagcctctcc ctgtctccgg gtaaaggagg    1080
cggtgggtca ggtaccggag gcggtgggtc aatccagcgt actccaaaga ttcaggttta    1140
ctcacgtcat ccagcagaga atggaaagtc aaatttcctg aattgctatg tgtctgggtt    1200
tcatccatcc gacattgaag ttgacttact gaagaatgga gagagaattg aaaaagtgga    1260
gcattcagac ttgtctttca gcaaggactg gtctttctat ctcttgtact acactgaatt    1320 caccccccact gaaaaagatg agtatgcctg ccgtgtgaac catgtgactt tgtcacagcc    1380
caagatagtt aagtgggatc gagacatgac cggtcatcat caccatcacc attga        1435

<210> SEQ ID NO 36
<211> LENGTH: 473
<212> TYPE: PRT
<213> ORGANISM: Artificial Sequence
<220> FEATURE:
<223> OTHER INFORMATION: Nucleotide sequence of the chimeric full
      IgG1-beta2 microglobulin

<400> SEQUENCE: 36

Met Gly Trp Ser Cys Ile Ile Leu Phe Leu Val Ala Thr Ala Thr Gly
1               5                   10                  15

Ala His Met Val Thr Val Ser Ser Ala Ser Thr Lys Gly Pro Ser Val
                20                  25                  30

Phe Pro Leu Ala Pro Ser Ser Lys Ser Thr Ser Gly Gly Thr Ala Ala
            35                  40                  45

Leu Gly Cys Leu Val Lys Asp Tyr Phe Pro Glu Pro Val Thr Val Ser
        50                  55                  60

Trp Asn Ser Gly Ala Leu Thr Ser Gly Val His Thr Phe Pro Ala Val
65                  70                  75                  80

Leu Gln Ser Ser Gly Leu Tyr Ser Leu Ser Ser Val Val Thr Val Pro
                85                  90                  95

Ser Ser Ser Leu Gly Thr Gln Thr Tyr Ile Cys Asn Val Asn His Lys
            100                 105                 110

Pro Ser Asn Thr Lys Val Asp Lys Lys Val Glu Pro Lys Ser Cys Asp
        115                 120                 125

Lys Thr His Thr Cys Pro Pro Cys Pro Ala Pro Glu Leu Leu Gly Gly
    130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
                165                 170                 175
```

-continued

```
Asp Pro Glu Val Lys Phe Asn Trp Tyr Val Asp Gly Val Glu Val His
            180                 185                 190

Asn Ala Lys Thr Lys Pro Arg Glu Glu Gln Tyr Asn Ser Thr Tyr Arg
        195                 200                 205

Val Val Ser Val Leu Thr Val Leu His Gln Asp Trp Leu Asn Gly Lys
    210                 215                 220

Glu Tyr Lys Cys Lys Val Ser Asn Lys Ala Leu Pro Ala Pro Ile Glu
225                 230                 235                 240

Lys Thr Ile Ser Lys Ala Lys Gly Gln Pro Arg Glu Pro Gln Val Tyr
                245                 250                 255

Thr Leu Pro Pro Ser Arg Asp Glu Leu Thr Lys Asn Gln Val Ser Leu
            260                 265                 270

Thr Cys Leu Val Lys Gly Phe Tyr Pro Ser Asp Ile Ala Val Glu Trp
        275                 280                 285

Glu Ser Asn Gly Gln Pro Glu Asn Asn Tyr Lys Thr Thr Pro Pro Val
    290                 295                 300

Leu Asp Ser Asp Gly Ser Phe Phe Leu Tyr Ser Lys Leu Thr Val Asp
305                 310                 315                 320

Lys Ser Arg Trp Gln Gln Gly Asn Val Phe Ser Cys Ser Val Met His
                325                 330                 335

Glu Ala Leu His Asn His Tyr Thr Gln Lys Ser Leu Ser Leu Ser Pro
            340                 345                 350

Gly Lys Gly Gly Gly Ser Gly Thr Gly Gly Gly Ser Ile Gln
        355                 360                 365

Arg Thr Pro Lys Ile Gln Val Tyr Ser Arg His Pro Ala Glu Asn Gly
    370                 375                 380

Lys Ser Asn Phe Leu Asn Cys Tyr Val Ser Gly Phe His Pro Ser Asp
385                 390                 395                 400

Ile Glu Val Asp Leu Leu Lys Asn Gly Glu Arg Ile Glu Lys Val Glu
                405                 410                 415

His Ser Asp Leu Val Phe Ser Lys Asp Trp Ser Phe Tyr Leu Leu Tyr
            420                 425                 430

Tyr Thr Glu Phe Thr Pro Thr Glu Lys Asp Glu Tyr Ala Cys Arg Val
        435                 440                 445

Asn His Val Thr Leu Ser Gln Pro Lys Ile Val Lys Trp Asp Arg Asp
    450                 455                 460

Met Thr Gly His His His His His His
465                 470

<210> SEQ ID NO 37
<211> LENGTH: 34
<212> TYPE: DNA
<213> ORGANISM: Artificial Sequence
<220> FEATURE:
<223> OTHER INFORMATION: Primer E1 Sense

<400> SEQUENCE: 37
cacggtaccg atatggggtg cctgctgttt ctgc                              34

<210> SEQ ID NO 38
<211> LENGTH: 30
<212> TYPE: DNA
<213> ORGANISM: Artificial Sequence
<220> FEATURE:
<223> OTHER INFORMATION: Primer E1 antisense

<400> SEQUENCE: 38
```

```
cagaccggtc cagtagagga cgatgtcctg                                      30
```

<210> SEQ ID NO 39
<211> LENGTH: 921
<212> TYPE: DNA
<213> ORGANISM: Artificial Sequence
<220> FEATURE:
<223> OTHER INFORMATION: Construct of extracellular domain of CD1d

<400> SEQUENCE: 39

```
ggtaccgata tggggtgcct gctgtttctg ctgctctggg cgctcctcca ggcttgggga    60
agcgctgaag tcccgcaaag cttttccccc ctccgctgcc tccagatctc gtccttcgcc   120
aatagcagct ggacgcgcac cgacggcttg gcgtggctgg gggagctgca gacgcacagc   180
tggagcaacg actcggacac cgtccgctct ctgaagcctt ggtcccaggg cacgttcagc   240
gaccagcagt gggagacgct gcagcatata tttcgggttt atcgaagcag cttcaccagg   300
gacgtgaagg aattcgccaa aatgctacgc ttatcctatc ccttggagct ccaggtgtcc   360
gctggctgtg aggtgcaccc tgggaacgcc tcaaataact tcttccatgt agcatttcaa   420
ggaaaagata tcctgagttt ccaaggaact tcttgggagc caacccaaga ggccccactt   480
tgggtaaact tggccattca agtgctcaac caggacaagt ggacgaggga aacagtgcag   540
tggctcctta atggcacctg cccccaattt gtcagtggcc tccttgagtc agggaagtcg   600
gaactgaaga agcaagtgaa gcccaaggcc tggctgtccc gtggcccag tcctggccct   660
ggccgtctgc tgctggtgtg ccatgtctca ggattctacc caaagcctgt atgggtgaag   720
tggatgcggg gtgagcagga gcagcagggc actcagccag ggacatcct gcccaatgct   780
gacgagacat ggtatctccg agcaaccctg gatgtggtgg ctggggaggc agctggcctg   840
tcctgtcggg tgaagcacag cagtctagag gccaggaca tcgtcctcta ctggaccggt   900
catcatcacc atcaccattg a                                            921
```

<210> SEQ ID NO 40
<211> LENGTH: 303
<212> TYPE: PRT
<213> ORGANISM: Artificial Sequence
<220> FEATURE:
<223> OTHER INFORMATION: Construct of extracellular domain of CD1d

<400> SEQUENCE: 40

```
Met Gly Cys Leu Leu Phe Leu Leu Leu Trp Ala Leu Leu Gln Ala Trp
1               5                   10                  15

Gly Ser Ala Glu Val Pro Gln Arg Leu Phe Pro Leu Arg Cys Leu Gln
            20                  25                  30

Ile Ser Ser Phe Ala Asn Ser Ser Trp Thr Arg Thr Asp Gly Leu Ala
        35                  40                  45

Trp Leu Gly Glu Leu Gln Thr His Ser Trp Ser Asn Asp Ser Asp Thr
    50                  55                  60

Val Arg Ser Leu Lys Pro Trp Ser Gln Gly Thr Phe Ser Asp Gln Gln
65                  70                  75                  80

Trp Glu Thr Leu Gln His Ile Phe Arg Val Tyr Arg Ser Ser Phe Thr
                85                  90                  95

Arg Asp Val Lys Glu Phe Ala Lys Met Leu Arg Leu Ser Tyr Pro Leu
            100                 105                 110

Glu Leu Gln Val Ser Ala Gly Cys Glu Val His Pro Gly Asn Ala Ser
        115                 120                 125
```

Asn Asn Phe Phe His Val Ala Phe Gln Gly Lys Asp Ile Leu Ser Phe
130                 135                 140

Gln Gly Thr Ser Trp Glu Pro Thr Gln Glu Ala Pro Leu Trp Val Asn
145                 150                 155                 160

Leu Ala Ile Gln Val Leu Asn Gln Asp Lys Trp Thr Arg Glu Thr Val
            165                 170                 175

Gln Trp Leu Leu Asn Gly Thr Cys Pro Gln Phe Val Ser Gly Leu Leu
            180                 185                 190

Glu Ser Gly Lys Ser Glu Leu Lys Lys Gln Val Lys Pro Lys Ala Trp
            195                 200                 205

Leu Ser Arg Gly Pro Ser Pro Gly Pro Arg Leu Leu Leu Val Cys
210                 215                 220

His Val Ser Gly Phe Tyr Pro Lys Pro Val Trp Val Lys Trp Met Arg
225                 230                 235                 240

Gly Glu Gln Glu Gln Gln Gly Thr Gln Pro Gly Asp Ile Leu Pro Asn
                245                 250                 255

Ala Asp Glu Thr Trp Tyr Leu Arg Ala Thr Leu Asp Val Val Ala Gly
            260                 265                 270

Glu Ala Ala Gly Leu Ser Cys Arg Val Lys His Ser Ser Leu Glu Gly
            275                 280                 285

Gln Asp Ile Val Leu Tyr Trp Thr Gly His His His His His
            290                 295                 300

<210> SEQ ID NO 41
<211> LENGTH: 38
<212> TYPE: DNA
<213> ORGANISM: Artificial Sequence
<220> FEATURE:
<223> OTHER INFORMATION: F(ab)-CD1d sense fragment

<400> SEQUENCE: 41
aattgcggcc gcaaaccatg ggatggagct gtatcatc       38

<210> SEQ ID NO 42
<211> LENGTH: 45
<212> TYPE: DNA
<213> ORGANISM: Artificial Sequence
<220> FEATURE:
<223> OTHER INFORMATION: F(ab)-CD1d antisense fragment

<400> SEQUENCE: 42
cggggtacct gacccaccgc ctcctttctt gtccaccttg gtgtt       45

<210> SEQ ID NO 43
<211> LENGTH: 38
<212> TYPE: DNA
<213> ORGANISM: Artificial Sequence
<220> FEATURE:
<223> OTHER INFORMATION: F(ab')2-CD1d sense fragment

<400> SEQUENCE: 43
aattgcggcc gcaaaccatg ggatggagct gtatcatc       38

<210> SEQ ID NO 44
<211> LENGTH: 45
<212> TYPE: DNA
<213> ORGANISM: Artificial Sequence
<220> FEATURE:
<223> OTHER INFORMATION: F(ab')2-CD1d antisense fragment

<400> SEQUENCE: 44

```
cggggtacct gacccaccgc ctcctgggca cggtgggcat gtgtg              45
```

<210> SEQ ID NO 45
<211> LENGTH: 38
<212> TYPE: DNA
<213> ORGANISM: Artificial Sequence
<220> FEATURE:
<223> OTHER INFORMATION: IgG1-CD1d sense fragment

<400> SEQUENCE: 45

```
aattgcggcc gcaaaccatg ggatggagct gtatcatc                     38
```

<210> SEQ ID NO 46
<211> LENGTH: 45
<212> TYPE: DNA
<213> ORGANISM: Artificial Sequence
<220> FEATURE:
<223> OTHER INFORMATION: IgG1-CD1d antisense fragment

<400> SEQUENCE: 46

```
cggggtacct gacccaccgc ctcctttacc cggagacagg gagag              45
```

<210> SEQ ID NO 47
<211> LENGTH: 42
<212> TYPE: DNA
<213> ORGANISM: Artificial Sequence
<220> FEATURE:
<223> OTHER INFORMATION: Artificial sense primer to construct
      extracellular CD1d

<400> SEQUENCE: 47

```
cggggtaccg gaggcggtgg gtcagtcccg caaaggcttt tc                 42
```

<210> SEQ ID NO 48
<211> LENGTH: 29
<212> TYPE: DNA
<213> ORGANISM: Artificial Sequence
<220> FEATURE:
<223> OTHER INFORMATION: Artificial antisense primer to construct
      extracellular CD1d

<400> SEQUENCE: 48

```
cgaccggtcc agtagaggac gatgtcctg                               29
```

<210> SEQ ID NO 49
<211> LENGTH: 1264
<212> TYPE: DNA
<213> ORGANISM: Artificial Sequence
<220> FEATURE:
<223> OTHER INFORMATION: Nucleotide sequence of the chimeric F(ab)-CD1d
      product

<400> SEQUENCE: 49

```
gcggccgcaa accatgggat ggagctgtat catcctcttc ttggtagcaa cagctacagg   60
cgcgcatatg gtcaccgtct cctcagcctc caccaagggc ccatcggtct tccccctggc  120
accctcctcc aagagcacct ctgggggcac agcggccctg ggctgcctgg tcaaggacta  180
cttccccgaa ccggtgacgg tgtcgtggaa ctcaggcgcc ctgaccagcg gcgtgcacac  240
cttcccggct gtcctacagt cctcaggact ctactccctc agcagcgtcg tgaccgtgcc  300
ctccagcagc ttgggcaccc agacctacat ctgcaacgtg aatcacaagc ccagcaacac  360
caaggtggac aagaaaggag gcggtgggtc aggtaccgga ggcggtgggt cagtcccgca  420
aaggcttttc ccctccgct gcctccagat ctcgtccttc gccaatagca gctggacgcg  480
```

```
caccgacggc ttggcgtggc tgggggagct gcagacgcac agctggagca acgactcgga    540
caccgtccgc tctctgaagc cttggtccca gggcacgttc agcgaccagc agtgggagac    600
gctgcagcat atatttcggg tttatcgaag cagcttcacc agggacgtga aggaattcgc    660
caaaatgcta cgcttatcct atcccttgga gctccaggtg tccgctggct gtgaggtgca    720
ccctgggaac gcctcaaata acttcttcca tgtagcattt caaggaaaag atatcctgag    780
tttccaagga acttcttggg agccaaccca agaggcccca ctttgggtaa acttggccat    840
tcaagtgctc aaccaggaca agtggacgag ggaaacagtg cagtggctcc ttaatggcac    900
ctgcccccaa tttgtcagtg gcctccttga gtcaggaaag tcggaactga agaagcaagt    960
gaagcccaag gcctggctgt cccgtggccc cagtcctggc cctggccgtc tgctgctggt   1020
gtgccatgtc tcaggattct acccaaagcc tgtatgggtg aagtggatgc ggggtgagca   1080
ggagcagcag ggcactcagc cagggacatc cctgcccaat gctgacgaga catggtatct   1140
ccgagcaacc ctggatgtgg tggctgggga ggcagctggc ctgtcctgtc gggtgaagca   1200
cagcagtcta gagggccagg acatcgtcct ctactggacc ggtcatcatc accatcacca   1260
ttga                                                                1264
```

<210> SEQ ID NO 50
<211> LENGTH: 416
<212> TYPE: PRT
<213> ORGANISM: Artificial Sequence
<220> FEATURE:
<223> OTHER INFORMATION: Polypeptide sequence of the chimeric F(ab)-CD1d
      product <400> SEQUENCE: 50

```
Met Gly Trp Ser Cys Ile Ile Leu Phe Leu Val Ala Thr Ala Thr Gly
1               5                   10                  15

Ala His Met Val Thr Val Ser Ser Ala Ser Thr Lys Gly Pro Ser Val
                20                  25                  30

Phe Pro Leu Ala Pro Ser Ser Lys Ser Thr Ser Gly Gly Thr Ala Ala
            35                  40                  45

Leu Gly Cys Leu Val Lys Asp Tyr Phe Pro Glu Pro Val Thr Val Ser
        50                  55                  60

Trp Asn Ser Gly Ala Leu Thr Ser Gly Val His Thr Phe Pro Ala Val
65                  70                  75                  80

Leu Gln Ser Ser Gly Leu Tyr Ser Leu Ser Ser Val Val Thr Val Pro
                85                  90                  95

Ser Ser Ser Leu Gly Thr Gln Thr Tyr Ile Cys Asn Val Asn His Lys
            100                 105                 110

Pro Ser Asn Thr Lys Val Asp Lys Lys Gly Gly Gly Ser Gly Thr
        115                 120                 125

Gly Gly Gly Gly Ser Val Pro Gln Arg Leu Phe Pro Leu Arg Cys Leu
    130                 135                 140

Gln Ile Ser Ser Phe Ala Asn Ser Ser Trp Thr Arg Thr Asp Gly Leu
145                 150                 155                 160

Ala Trp Leu Gly Glu Leu Gln Thr His Ser Trp Ser Asn Asp Ser Asp
                165                 170                 175

Thr Val Arg Ser Leu Lys Pro Trp Ser Gln Gly Thr Phe Ser Asp Gln
            180                 185                 190

Gln Trp Glu Thr Leu Gln His Ile Phe Arg Val Tyr Arg Ser Ser Phe
        195                 200                 205

Thr Arg Asp Val Lys Glu Phe Ala Lys Met Leu Arg Leu Ser Tyr Pro
```

```
                 210                 215                 220
Leu Glu Leu Gln Val Ser Ala Gly Cys Glu Val His Pro Gly Asn Ala
225                 230                 235                 240

Ser Asn Asn Phe Phe His Val Ala Phe Gln Gly Lys Asp Ile Leu Ser
                245                 250                 255

Phe Gln Gly Thr Ser Trp Glu Pro Thr Gln Glu Ala Pro Leu Trp Val
            260                 265                 270

Asn Leu Ala Ile Gln Val Leu Asn Gln Asp Lys Trp Thr Arg Glu Thr
        275                 280                 285

Val Gln Trp Leu Leu Asn Gly Thr Cys Pro Gln Phe Val Ser Gly Leu
    290                 295                 300

Leu Glu Ser Gly Lys Ser Glu Leu Lys Lys Gln Val Lys Pro Lys Ala
305                 310                 315                 320

Trp Leu Ser Arg Gly Pro Ser Pro Gly Pro Gly Arg Leu Leu Leu Val
                325                 330                 335

Cys His Val Ser Gly Phe Tyr Pro Lys Pro Val Trp Val Lys Trp Met
            340                 345                 350

Arg Gly Glu Gln Glu Gln Gln Gly Thr Gln Pro Gly Asp Ile Leu Pro
        355                 360                 365

Asn Ala Asp Glu Thr Trp Tyr Leu Arg Ala Thr Leu Asp Val Val Ala
    370                 375                 380

Gly Glu Ala Ala Gly Leu Ser Cys Arg Val Lys His Ser Ser Leu Glu
385                 390                 395                 400

Gly Gln Asp Ile Val Leu Tyr Trp Thr Gly His His His His His His
                405                 410                 415

<210> SEQ ID NO 51
<211> LENGTH: 1312
<212> TYPE: DNA
<213> ORGANISM: Artificial Sequence
<220> FEATURE:
<223> OTHER INFORMATION: Nucleotide sequence of the chimeric
      F(ab')2-CD1d product

<400> SEQUENCE: 51
gcggccgcaa accatgggat ggagctgtat catcctcttc ttggtagcaa cagctacagg    60
cgcgcatatg gtcaccgtct cctcagcctc caccaagggc ccatcggtct tccccctggc   120
accctcctcc aagagcacct ctgggggcac agcggccctg ggctgcctgg tcaaggacta   180
cttccccgaa ccggtgacgg tgtcgtggaa ctcaggcgcc ctgaccagcg gcgtgcacac   240
cttcccggct gtcctacagt cctcaggact ctactccctc agcagcgtcg tgaccgtgcc   300
ctccagcagc ttgggcaccc agacctacat ctgcaacgtg aatcacaagc ccagcaacac   360
caaggtggac aagaaagttg agcccaaatc ttgtgacaaa actcacacat gcccaccgtg   420
cccaggaggc ggtgggtcag gtaccggagg cggtgggtca gtcccgcaaa ggcttttccc   480
cctccgctgc ctccagatct cgtccttcgc aatagcagct ggacgcgcca ccgacggctt   540
ggcgtggctg ggggagctgc agacgcacag ctggagcaac gactcggaca ccgtccgctc   600
tctgaagcct tggtcccagg gcacgttcag cgaccagcag tgggagacgc tgcagcatat   660
atttcgggtt tatcgaagca gcttcaccag ggacgtgaag gaattcgcca aaatgctacg   720
cttatcctat ccccttggag ccaggtgtc cgctggctgt gaggtgcacc ctgggaacgc   780
ctcaaataac ttcttccatg tagcatttca aggaaaagat atcctgagtt tccaaggaac   840
ttcttgggag ccaacccaag aggccccact ttgggtaaac ttggccattc aagtgctcaa   900
```

```
ccaggacaag tggacgaggg aaacagtgca gtggctcctt aatggcacct gcccccaatt    960
tgtcagtggc ctccttgagt cagggaagtc ggaactgaag aagcaagtga agcccaaggc   1020
ctggctgtcc cgtggcccca gtcctggccc tggccgtctg ctgctggtgt gccatgtctc   1080
aggattctac ccaaagcctg tatgggtgaa gtggatgcgg ggtgagcagg agcagcaggg   1140
cactcagcca ggggacatcc tgcccaatgc tgacgagaca tggtatctcc gagcaaccct   1200
ggatgtggtg gctggggagg cagctggcct gtcctgtcgg gtgaagcaca gcagtctaga   1260
gggccaggac atcgtcctct actggaccgg tcatcatcac catcaccatt ga            1312
```

<210> SEQ ID NO 52
<211> LENGTH: 432
<212> TYPE: PRT
<213> ORGANISM: Artificial Sequence
<220> FEATURE:
<223> OTHER INFORMATION: Polypeptide sequence of the chimeric
      F(ab')2-CD1d product

<400> SEQUENCE: 52

```
Met Gly Trp Ser Cys Ile Ile Leu Phe Leu Val Ala Thr Ala Thr Gly
1               5                   10                  15

Ala His Met Val Thr Val Ser Ser Ala Ser Thr Lys Gly Pro Ser Val
            20                  25                  30

Phe Pro Leu Ala Pro Ser Ser Lys Ser Thr Ser Gly Gly Thr Ala Ala
        35                  40                  45

Leu Gly Cys Leu Val Lys Asp Tyr Phe Pro Glu Pro Val Thr Val Ser
    50                  55                  60

Trp Asn Ser Gly Ala Leu Thr Ser Gly Val His Thr Phe Pro Ala Val
65                  70                  75                  80

Leu Gln Ser Ser Gly Leu Tyr Ser Leu Ser Ser Val Val Thr Val Pro
                85                  90                  95

Ser Ser Ser Leu Gly Thr Gln Thr Tyr Ile Cys Asn Val Asn His Lys
            100                 105                 110

Pro Ser Asn Thr Lys Val Asp Lys Lys Val Glu Pro Lys Ser Cys Asp
        115                 120                 125

Lys Thr His Thr Cys Pro Pro Cys Pro Gly Gly Gly Gly Ser Gly Thr
    130                 135                 140

Gly Gly Gly Gly Ser Val Pro Gln Arg Leu Phe Pro Leu Arg Cys Leu
145                 150                 155                 160

Gln Ile Ser Ser Phe Ala Asn Ser Ser Trp Thr Arg Thr Asp Gly Leu
                165                 170                 175

Ala Trp Leu Gly Glu Leu Gln Thr His Ser Trp Ser Asn Asp Ser Asp
            180                 185                 190

Thr Val Arg Ser Leu Lys Pro Trp Ser Gln Gly Thr Phe Ser Asp Gln
        195                 200                 205

Gln Trp Glu Thr Leu Gln His Ile Phe Arg Val Tyr Arg Ser Ser Phe
    210                 215                 220

Thr Arg Asp Val Lys Glu Phe Ala Lys Met Leu Arg Leu Ser Tyr Pro
225                 230                 235                 240

Leu Glu Leu Gln Val Ser Ala Gly Cys Glu Val His Pro Gly Asn Ala
                245                 250                 255

Ser Asn Asn Phe Phe His Val Ala Phe Gln Gly Lys Asp Ile Leu Ser
            260                 265                 270

Phe Gln Gly Thr Ser Trp Glu Pro Thr Gln Glu Ala Pro Leu Trp Val
        275                 280                 285
```

```
Asn Leu Ala Ile Gln Val Leu Asn Gln Asp Lys Trp Thr Arg Glu Thr
    290                 295                 300
Val Gln Trp Leu Leu Asn Gly Thr Cys Pro Gln Phe Val Ser Gly Leu
305                 310                 315                 320
Leu Glu Ser Gly Lys Ser Glu Leu Lys Lys Gln Val Lys Pro Lys Ala
                325                 330                 335
Trp Leu Ser Arg Gly Pro Ser Pro Gly Pro Gly Arg Leu Leu Leu Val
                340                 345                 350
Cys His Val Ser Gly Phe Tyr Pro Lys Pro Val Trp Val Lys Trp Met
                355                 360                 365
Arg Gly Glu Gln Glu Gln Gln Gly Thr Gln Pro Gly Asp Ile Leu Pro
    370                 375                 380
Asn Ala Asp Glu Thr Trp Tyr Leu Arg Ala Thr Leu Asp Val Val Ala
385                 390                 395                 400
Gly Glu Ala Ala Gly Leu Ser Cys Arg Val Lys His Ser Ser Leu Glu
                405                 410                 415
Gly Gln Asp Ile Val Leu Tyr Trp Thr Gly His His His His His
                420                 425                 430
```

<210> SEQ ID NO 53
<211> LENGTH: 1963
<212> TYPE: DNA
<213> ORGANISM: Artificial Sequence
<220> FEATURE:
<223> OTHER INFORMATION: Nucleotide sequence of the chimeric IgG1-CD1d
      product

<400> SEQUENCE: 53

```
gcggccgcaa accatgggat ggagctgtat catcctcttc ttggtagcaa cagctacagg      60
cgcgcatatg gtcaccgtct cctcagcctc caccaagggc ccatcggtct tccccctggc     120
accctcctcc aagagcacct ctgggggcac agcggccctg ggctgcctgg tcaaggacta     180
cttccccgaa ccggtgacgg tgtcgtggaa ctcaggcgcc ctgaccagcg gcgtgcacac     240
cttcccggct gtcctacagt cctcaggact ctactccctc agcagcgtcg tgaccgtgcc     300
ctccagcagc ttgggcaccc agacctacat ctgcaacgtg aatcacaagc ccagcaacac     360
caaggtggac aagaaagttg agcccaaatc ttgtgacaaa actcacacat gcccaccgtg     420
cccagcacct gaactcctgg ggggaccgtc agtcttcctc ttccccccaa aacccaagga     480
caccctcatg atctcccgga cccctgaggt cacatgcgtg gtggtggacg tgagccacga     540
agaccctgag gtcaagttca actggtacgt ggacggcgtg gaggtgcata atgccaagac     600
aaagccgcgg gaggagcagt acaacagcac gtaccgtgtg gtcagcgtcc tcaccgtcct     660
gcaccaggac tggctgaatg gcaaggagta caagtgcaag gtctccaaca aagccctccc     720
agcccccatc gagaaaacca tctccaaagc caaagggcag ccccgagaac cacaggtgta     780
caccctgccc ccatcccggg atgagctgac caagaaccag gtcagcctga cctgcctggt     840
caaaggcttc tatcccagcg acatcgccgt ggagtgggag agcaatgggc agccggagaa     900
caactacaag accacgcctc ccgtgctgga ctccgacggc tccttcttcc tctacagcaa     960
gctcaccgtg gacaagagca ggtggcagca ggggaacgtc ttctcatgct ccgtgatgca    1020
tgaggctctg cacaaccact acacgcagaa gagcctctcc ctgtctccgg gtaaaggagg    1080
cggtgggtca ggtaccggag gcggtgggtc agtcccgcaa aggctttttcc ccctccgctg   1140
cctccagatc tcgtccttcg ccaatagcag ctggacgcgc accgacggct tggcgtggct   1200
gggggagctg cagacgcaca gctggagcaa cgactcggac accgtccgct ctctgaagcc   1260
```

-continued

```
ttggtcccag ggcacgttca gcgaccagca gtgggagacg ctgcagcata tatttcgggt    1320
ttatcgaagc agcttcacca gggacgtgaa ggaattcgcc aaaatgctac gcttatccta    1380
tcccttggag ctccaggtgt ccgctggctg tgaggtgcac cctgggaacg cctcaaataa    1440
cttcttccat gtagcatttc aaggaaaaga tatcctgagt tccaaggaa cttcttggga     1500
gccaacccaa gaggccccac tttgggtaaa cttggccatt caagtgctca accaggacaa    1560
gtggacgagg gaaacagtgc agtggctcct taatggcacc tgcccccaat ttgtcagtgg    1620
cctccttgag tcagggaagt cggaactgaa gaagcaagtg aagcccaagg cctggctgtc    1680
ccgtggcccc agtcctggcc ctggccgtct gctgctggtg tgccatgtct caggattcta    1740
cccaaagcct gtatgggtga agtggatgcg gggtgagcag gagcagcagg cactcagcc    1800
agggacatc ctgcccaatg ctgacgagac atggtatctc cgagcaaccc tggatgtggt     1860
ggctggggag gcagctggcc tgtcctgtcg ggtgaagcac agcagtctag agggccagga    1920
catcgtcctc tactggaccg gtcatcatca ccatcaccat tga                      1963
```

<210> SEQ ID NO 54
<211> LENGTH: 649
<212> TYPE: PRT
<213> ORGANISM: Artificial Sequence
<220> FEATURE:
<223> OTHER INFORMATION: Polypeptide sequence of the IgG1CD1d product

<400> SEQUENCE: 54

```
Met Gly Trp Ser Cys Ile Ile Leu Phe Leu Val Ala Thr Ala Thr Gly
1               5                   10                  15

Ala His Met Val Thr Val Ser Ser Ala Ser Thr Lys Gly Pro Ser Val
            20                  25                  30

Phe Pro Leu Ala Pro Ser Ser Lys Ser Thr Ser Gly Gly Thr Ala Ala
        35                  40                  45

Leu Gly Cys Leu Val Lys Asp Tyr Phe Pro Glu Pro Val Thr Val Ser
    50                  55                  60

Trp Asn Ser Gly Ala Leu Thr Ser Gly Val His Thr Phe Pro Ala Val
65                  70                  75                  80

Leu Gln Ser Ser Gly Leu Tyr Ser Leu Ser Ser Val Val Thr Val Pro
                85                  90                  95

Ser Ser Ser Leu Gly Thr Gln Thr Tyr Ile Cys Asn Val Asn His Lys
            100                 105                 110

Pro Ser Asn Thr Lys Val Asp Lys Lys Val Glu Pro Lys Ser Cys Asp
        115                 120                 125

Lys Thr His Thr Cys Pro Pro Cys Pro Ala Pro Glu Leu Leu Gly Gly
    130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
                165                 170                 175

Asp Pro Glu Val Lys Phe Asn Trp Tyr Val Asp Gly Val Glu Val His
            180                 185                 190

Asn Ala Lys Thr Lys Pro Arg Glu Glu Gln Tyr Asn Ser Thr Tyr Arg
        195                 200                 205

Val Val Ser Val Leu Thr Val Leu His Gln Asp Trp Leu Asn Gly Lys
    210                 215                 220

Glu Tyr Lys Cys Lys Val Ser Asn Lys Ala Leu Pro Ala Pro Ile Glu
225                 230                 235                 240
```

```
Lys Thr Ile Ser Lys Ala Lys Gly Gln Pro Arg Glu Pro Gln Val Tyr
                245                 250                 255

Thr Leu Pro Pro Ser Arg Asp Glu Leu Thr Lys Asn Gln Val Ser Leu
        260                 265                 270

Thr Cys Leu Val Lys Gly Phe Tyr Pro Ser Asp Ile Ala Val Glu Trp
        275                 280                 285

Glu Ser Asn Gly Gln Pro Glu Asn Asn Tyr Lys Thr Thr Pro Pro Val
        290                 295                 300

Leu Asp Ser Asp Gly Ser Phe Phe Leu Tyr Ser Lys Leu Thr Val Asp
305                 310                 315                 320

Lys Ser Arg Trp Gln Gln Gly Asn Val Phe Ser Cys Ser Val Met His
                325                 330                 335

Glu Ala Leu His Asn His Tyr Thr Gln Lys Ser Leu Ser Leu Ser Pro
                340                 345                 350

Gly Lys Gly Gly Gly Gly Ser Gly Thr Gly Gly Gly Ser Val Pro
                355                 360                 365

Gln Arg Leu Phe Pro Leu Arg Cys Leu Gln Ile Ser Ser Phe Ala Asn
        370                 375                 380

Ser Ser Trp Thr Arg Thr Asp Gly Leu Ala Trp Leu Gly Glu Leu Gln
385                 390                 395                 400

Thr His Ser Trp Ser Asn Asp Ser Asp Thr Val Arg Ser Leu Lys Pro
                405                 410                 415

Trp Ser Gln Gly Thr Phe Ser Asp Gln Gln Trp Glu Thr Leu Gln His
                420                 425                 430

Ile Phe Arg Val Tyr Arg Ser Ser Phe Thr Arg Asp Val Lys Glu Phe
                435                 440                 445

Ala Lys Met Leu Arg Leu Ser Tyr Pro Leu Glu Leu Gln Val Ser Ala
450                 455                 460

Gly Cys Glu Val His Pro Gly Asn Ala Ser Asn Asn Phe Phe His Val
465                 470                 475                 480

Ala Phe Gln Gly Lys Asp Ile Leu Ser Phe Gln Gly Thr Ser Trp Glu
                485                 490                 495

Pro Thr Gln Glu Ala Pro Leu Trp Val Asn Leu Ala Ile Gln Val Leu
                500                 505                 510

Asn Gln Asp Lys Trp Thr Arg Glu Thr Val Gln Trp Leu Leu Asn Gly
                515                 520                 525

Thr Cys Pro Gln Phe Val Ser Gly Leu Leu Glu Ser Gly Lys Ser Glu
        530                 535                 540

Leu Lys Lys Gln Val Lys Pro Lys Ala Trp Leu Ser Arg Gly Pro Ser
545                 550                 555                 560

Pro Gly Pro Gly Arg Leu Leu Leu Val Cys His Val Ser Gly Phe Tyr
                565                 570                 575

Pro Lys Pro Val Trp Val Lys Trp Met Arg Gly Glu Gln Glu Gln Gln
                580                 585                 590

Gly Thr Gln Pro Gly Asp Ile Leu Pro Asn Ala Asp Glu Thr Trp Tyr
                595                 600                 605

Leu Arg Ala Thr Leu Asp Val Val Ala Gly Glu Ala Ala Gly Leu Ser
        610                 615                 620

Cys Arg Val Lys His Ser Ser Leu Glu Gly Gln Asp Ile Val Leu Tyr
625                 630                 635                 640

Trp Thr Gly His His His His His
                645
```